US009526915B2

(12) United States Patent
Kovach

(10) Patent No.: US 9,526,915 B2
(45) Date of Patent: Dec. 27, 2016

(54) METHODS FOR REGULATING CELL MITOSIS BY INHIBITING SERINE/THREONINE PHOSPHATASE

(71) Applicant: John S. Kovach, East Setauket, NY (US)

(72) Inventor: John S. Kovach, East Setauket, NY (US)

( * ) Notice: Subject to any disclaimer, the term of this patent is extended or adjusted under 35 U.S.C. 154(b) by 43 days.

(21) Appl. No.: 13/870,763

(22) Filed: Apr. 25, 2013

(65) Prior Publication Data

US 2013/0280210 A1 Oct. 24, 2013

Related U.S. Application Data

(63) Continuation of application No. 13/378,623, filed as application No. PCT/US2010/000279 on Feb. 1, 2010, now abandoned, which is a continuation-in-part of application No. PCT/US2009/004108, filed on Jul. 16, 2009.

(60) Provisional application No. 61/269,101, filed on Jun. 18, 2009, provisional application No. 61/137,715, filed on Aug. 1, 2008.

(51) Int. Cl.
| | |
|---|---|
| *A61K 31/496* | (2006.01) |
| *A61N 5/10* | (2006.01) |
| *A61K 31/44* | (2006.01) |
| *A61K 31/337* | (2006.01) |
| *A61K 38/20* | (2006.01) |
| *A61K 38/21* | (2006.01) |
| *A61K 38/50* | (2006.01) |
| *A61K 39/395* | (2006.01) |
| *A61K 45/06* | (2006.01) |
| *C07D 493/08* | (2006.01) |

(52) U.S. Cl.
CPC ............. *A61N 5/10* (2013.01); *A61K 31/337* (2013.01); *A61K 31/44* (2013.01); *A61K 31/496* (2013.01); *A61K 38/20* (2013.01); *A61K 38/212* (2013.01); *A61K 38/50* (2013.01); *A61K 39/39558* (2013.01); *A61K 45/06* (2013.01); *C07D 493/08* (2013.01)

(58) Field of Classification Search
None
See application file for complete search history.

(56) References Cited

U.S. PATENT DOCUMENTS

| | | | |
|---|---|---|---|
| 2,957,906 A | 10/1960 | Erickson et al. | |
| 3,980,674 A | 9/1976 | Kubela et al. | |
| 4,143,054 A | 3/1979 | Sprague | |
| 4,218,478 A | 8/1980 | Omura et al. | |
| 4,298,752 A | 11/1981 | Dauben et al. | |
| 4,463,015 A | 7/1984 | Haslanger et al. | |
| 4,524,151 A | 6/1985 | Das et al. | |
| 4,614,825 A | 9/1986 | Snitman et al. | |
| 4,654,355 A | 3/1987 | Nakane et al. | |
| 4,690,918 A | 9/1987 | Beppu et al. | |
| 4,816,579 A | 3/1989 | Thottathil et al. | |
| 4,851,423 A | 7/1989 | Girijavallabhan et al. | |
| 4,851,553 A | 7/1989 | Thottathil | |
| 5,266,710 A | 11/1993 | Patel et al. | |
| 5,326,898 A | 7/1994 | Chandraratna | |
| 5,925,651 A | 7/1999 | Hutchinson | |
| 5,968,965 A | 10/1999 | Dinsmore et al. | |
| 6,222,055 B1 | 4/2001 | Wolter et al. | |
| 6,696,483 B2 | 2/2004 | Singh | |
| 6,706,762 B1 | 3/2004 | Evans et al. | |
| 6,777,217 B1 | 8/2004 | Schreiber et al. | |
| 6,949,624 B1 | 9/2005 | Liu et al. | |
| 7,067,551 B2 | 6/2006 | Remiszewski et al. | |
| 7,154,002 B1 | 12/2006 | Bressi et al. | |
| 7,998,957 B2 | 8/2011 | Kovach et al. | |
| 8,058,268 B2 | 11/2011 | Kovach | |
| 8,143,445 B2 | 3/2012 | Kovach et al. | |
| 8,227,473 B2 | 7/2012 | Kovach et al. | |
| 8,329,719 B2 | 12/2012 | Kovach | |
| 8,426,444 B2 | 4/2013 | Kovach et al. | |
| 8,455,688 B2 | 6/2013 | Kovach et al. | |
| 8,541,458 B2 | 9/2013 | Kovach et al. | |
| 8,822,461 B2 | 9/2014 | Kovach et al. | |
| 9,079,917 B2 | 7/2015 | Kovach et al. | |
| 2002/0147345 A1 | 10/2002 | El Tayer et al. | |
| 2002/0177692 A1 | 11/2002 | Bartel | |
| 2003/0162186 A1 | 8/2003 | Bejanin et al. | |
| 2004/0010045 A1 | 1/2004 | Yi | |
| 2004/0053996 A1 | 3/2004 | Gesing et al. | |

(Continued)

FOREIGN PATENT DOCUMENTS

| | | |
|---|---|---|
| DE | 196 00 707 A1 | 7/1997 |
| EP | 1443967 | 1/2007 |

(Continued)

OTHER PUBLICATIONS

Hong et al. Biochem. Biophys. Res. Comm. 276, pp. 278-285 (2000).*
Kim et al. (Int. J. Radiation Oncology Biol. Phys. 59(4), 1174-80 (2004).*
Koukourakis et al. Int. J. Radiation Oncology Biol. Phys., 2004, vol. 59, No. 4, pp. 1174-1180 (Abstract attached).*
Acharya et al. (2005) "Rational development of histone deacetylase inhibitors as anticancer agents: a review", Mol. Pharmacol., 68, pp. 917-932.
Bertini, I. (2009) "Structural Basis of Serine/Threonine Phosphatase Inhibition by the Archetypal Small Molecules Cantharidin and Norcantharldin", J. Med. Chem. 52, p. 4838-4843.

(Continued)

*Primary Examiner* — James D Anderson
(74) *Attorney, Agent, or Firm* — John P. White; Gary J. Gershik; Cooper & Dunham LLP

(57) ABSTRACT

Disclosed herein are methods of inhibiting proliferation of a cancer cell or inducing apoptosis of a cancer cell, which does not overexpress N—CoR. Also disclosed herein are methods of inhibiting proliferation or inducing apoptosis of a cancer cell that overexpresses TCTP and methods for determining whether a compound is effective in inducing cell death.

25 Claims, 29 Drawing Sheets

(56) References Cited

U.S. PATENT DOCUMENTS

| | | |
|---|---|---|
| 2004/0087531 A1* | 5/2004 | Telerman et al. .............. 514/44 |
| 2004/0106141 A1 | 6/2004 | Mischel et al. |
| 2004/0122101 A1 | 6/2004 | Miller et al. |
| 2004/0161475 A1 | 8/2004 | Ellison et al. |
| 2004/0197888 A1 | 10/2004 | Armour et al. |
| 2004/0253637 A1 | 12/2004 | Buechler et al. |
| 2005/0054626 A1 | 3/2005 | Carter et al. |
| 2005/0119229 A1 | 6/2005 | Ammermann et al. |
| 2005/0203082 A1 | 9/2005 | Hsu et al. |
| 2005/0272644 A1 | 12/2005 | Chung et al. |
| 2005/0282893 A1 | 12/2005 | Au et al. |
| 2006/0030616 A1 | 2/2006 | McCluskey et al. |
| 2006/0134682 A1 | 6/2006 | Roberts et al. |
| 2007/0135365 A1 | 6/2007 | Tanizawa et al. |
| 2007/0135433 A1 | 6/2007 | Dean et al. |
| 2007/0155751 A1 | 7/2007 | Paruch et al. |
| 2007/0197550 A1 | 8/2007 | Georgopapadakou et al. |
| 2007/0208166 A1 | 9/2007 | Baly et al. |
| 2007/0213330 A1 | 9/2007 | Delorme et al. |
| 2008/0132503 A1 | 6/2008 | Moradei et al. |
| 2008/0214569 A1 | 9/2008 | Zhuang et al. |
| 2009/0012066 A1 | 1/2009 | Izumo et al. |
| 2009/0018142 A9 | 1/2009 | Zhuang et al. |
| 2009/0035292 A1* | 2/2009 | Kovach et al. .............. 424/94.6 |
| 2009/0036309 A1 | 2/2009 | Kovach et al. |
| 2009/0143445 A1 | 6/2009 | Kovach et al. |
| 2010/0029484 A1 | 2/2010 | Kovach et al. |
| 2010/0029640 A1 | 2/2010 | Kovach et al. |
| 2010/0029683 A1* | 2/2010 | Kovach et al. .......... 514/254.11 |
| 2011/0287537 A1 | 11/2011 | Kovach |
| 2012/0135522 A1 | 5/2012 | Kovach et al. |

FOREIGN PATENT DOCUMENTS

| | | |
|---|---|---|
| FR | 2 872 704 | 1/2006 |
| JP | 50-69091 | 10/1973 |
| JP | 51-88631 | 1/1975 |
| JP | 51-98755 | 1/1975 |
| JP | 51 032733 A | 3/1976 |
| JP | 2-256650 | 12/1989 |
| JP | 10-504305 | 2/1996 |
| JP | 2002-520415 | 1/2000 |
| JP | 2001-329061 | 6/2000 |
| JP | 2004-531500 | 10/2002 |
| JP | 2006-519609 | 9/2004 |
| JP | 2005-507852 | 3/2005 |
| JP | 2007-511528 | 5/2007 |
| JP | 2007-514665 | 6/2007 |
| RU | 201598 C1 | 7/1994 |
| SU | 1553533 A1 | 3/1990 |
| WO | WO 91/18891 | 12/1991 |
| WO | WO 00/04023 | 1/2000 |
| WO | WO 02/09680 | 2/2002 |
| WO | WO 02/42310 | 5/2002 |
| WO | WO 02/076989 | 10/2002 |
| WO | WO 03/092616 | 11/2003 |
| WO | WO 2004/080416 | 9/2004 |
| WO | WO 2005/018673 | 3/2005 |
| WO | WO 2005/049084 | 6/2005 |
| WO | WO 2005/054257 | 6/2005 |
| WO | WO 2005/058280 | 6/2005 |
| WO | WO 2005/074941 | 8/2005 |
| WO | WO 2006/023603 | 3/2006 |
| WO | WO 2006/129105 | 12/2006 |
| WO | WO 2007/014029 | 2/2007 |
| WO | WO 2007/021682 | 2/2007 |
| WO | WO 2007/092414 | 8/2007 |
| WO | WO 2007/092414 A2 * | 8/2007 |
| WO | WO 2007/118137 | 10/2007 |
| WO | 2008/030617 | 3/2008 |
| WO | WO 2008/028965 | 3/2008 |
| WO | WO 2008/058342 | 3/2008 |
| WO | WO 2008/097561 A1 * | 8/2008 |
| WO | WO 2009/020565 | 2/2009 |
| WO | WO 2009/045440 | 4/2009 |
| WO | WO 2010/014141 | 2/2010 |
| WO | WO 2010/014220 | 2/2010 |
| WO | WO 2010/014254 | 2/2010 |
| WO | WO 2010/147612 | 12/2010 |
| WO | WO 2012/162535 | 11/2012 |
| WO | WO 2014/005080 | 1/2014 |
| WO | WO 2014/005084 | 1/2014 |
| WO | WO 2014/137741 | 9/2014 |
| WO | WO 2014/149494 | 9/2014 |
| WO | WO 2014/168941 | 10/2014 |
| WO | WO 2015/073802 A1 | 5/2015 |
| WO | WO 2015/196073 A1 | 12/2015 |
| WO | WO 2016/014783 A1 | 1/2016 |
| WO | WO 2016/040877 A1 | 3/2016 |
| WO | WO 2016/061193 A1 | 4/2016 |

OTHER PUBLICATIONS

Andrabi, S. et al. (2007) "B. Protein Phosphatase 2A regulates life and death decisions via Akt in a context-dependent manner" Proc. Natl. Acad. Sci USA 104:19011-19016.

Avila et al. "Tau phosphorylation, aggregation, and cell toxicity." J. Biomedicine and Biotechnology, Hinwadi Publishing Corporation, vol. 2006, pp. 1-5.

Ayaydin, F. et al. (2000) "Inhibition of serine/threonine specific protein phosphatases causes premature activation of cdc2MsF kinase at G2/M transition and early mitotic microtubule organization in alfalfa." The Plant Journal, 23:85-96.

Baki, L. et al. (2004) The EMBO Journal 23:2586-2596.

Baskin, T. and Wilson, J. (1997) "Inhibitors of protein kinases and phosphatases alter root morphology and disorganize cortical microtubules." Plant Physiol. 113:493-502.

Bastien et al. (2004) "Nuclear retinoid receptors and the transcription of retinoid-target genes." Gen vol. 328, pp. 1-16.

Berthold, F., et al. (2005) "Myeloablative megatherapy with autologous stem-cell rescue versus oral maintenance chemotherapy as consolidation treatment in patients with high-risk neuroblastoma: a randomised controlled trial." Lancet Oncol., 6:649-658.

Hill, T. et al (2007) "Heterocyclic Substituted Cantharidin and Norcantharidin Analogues-Synthesis, Protein Phosphatase Inhibition and Anti-Cancer Activity." Bioorg. Med. Chem. let. 17, p. 3392-3397.

Blaheta, A. et al. (2002). "Valproate and Valproate-Analogues: potent Tools to Fight Against Cancer," Current Medicinal Chemistry, vol. 9, pp. 1317-1344.

Bommer, U.A. and Thiele, B.J. (2004) "The translationally controlled tumor protein TCTP" International Journal of Biochemistry & Cell Biology 36:379-385.

Boness, K. et al. (2006) "Cantharidin-induced mitotic arrest is associated with the formation of aberrant mitotic spindles and laggin chromosomes resulting, in part, from the suppression of PP2Ax" Mol. Cancer Ther. 5:2727-2736.

Brazil, D.P. et al. (2004) "Advances in protein kinase B signalling: AKTion on multiple fronts" Trends in Biochemical Sciences 29:233-242.

Camphausen et al. (2005) "Influence of in vivo growth on human glioma cell line gene expression: Convergent profiles under orthotopic conditions." Proc. Natl. Acad. Sci. USA, vol. 102, No. 23, pp. 8287-8292.

Casteda, M. et al. (2004) "Cell death by mitotic catastrophe: a molecular definition" Oncogene 23:825-2837.

Chen, S. et al. (2007) "Mcl-1 Down-regulation potentiates ABT-737 Lethality by Cooperatively Inducing Bak Activation and Bax Translocation" American Association for Cancer Research 6:782-791.

Chen, S.H. et al. (2007) "A knockout mouse approach reveals that TCTP functions as an essential factor for cell proliferation and survival in a tissue or cell type specific manner" Molecular Biology of the Cell 18:2525-2532.

Crafts, A.S., (1953) Rev. Plant. Physiol., 4:253-282.

Craig, R.W. (2002) "MCL1 provides a window on the role of the BCL2 family in cell proliferation, differentiation and tumorigenesis" Leukemia 16:444-454.

D'Adda di Fagagna (2008) "Living on a break: cellular senescence as a DNA damage response" Nature Reviews Cancer 8:512-522.

(56) References Cited

OTHER PUBLICATIONS

Drewinko et al. (1967), "Combination chemotherapy in vitro with adriamycin. Observations of additive, antagonistic, and synergistic effects when used in two-drug combinations on cultured human lymphoma cells," Cancer Biochem. Biophys., vol. 1, pp. 187-195.
Erdodi et al. (1995), "Endothal thioanhydride inhibits proteins phosphatases-1 and -2A inhibition, and anticancer activity," Am. J. Physol. (Cell Physiol.) vol. 38, pp. C1176-C1184.
Essers, M. et al., (2001) "Synthesis of the first fluorinated cantharidin analogues." Tetrahedron Lett., 42, 5429-5433.
Fabel et al. 2001, Long-term stablization in patients with malignant glioma after treatment with liposomal doxorubicin. Cancer, vol. 92, No. 7, pp. 1936-1942.
Fanghanel, F. et al. (1994) Synthesis, 10:1067-1071.
Forester, C.M. et al. (2007) "Control of mitotic exit by PP2A regulation of Cdc25C and Cdk1" Proc. Natl. Acad. Sci. 112:1257-1271.
Furumai et al. (2001) "Potent histone deacetylase inhibitors built from trichostatin A and cyclic tetrapeptide antibiotics including trapoxin" Proc. Natl. Acad. Sci. USA, 98(1), pp. 87-92.
Gachet, Y. et al. (1999) "The growth-related, translationally controlled protein P23 has properties of a tubulin binding protein and associates transiently with micro tubules during the cell cycle" Journal of Cell Science 112:1257-1271.
Garcia-Echeverria, C. and Sellers, W.A. (2008) Drug discovery approaches targeting the P13K/Akt pathway in cancer Oncogene 27:5511-5526.
Giannini, R. and Cavallini, A. (2005), "Expression analysis of a subset of coregulators and three nuclear receptors in colorectal carcinoma." Anticancer Research, vol. 36, No. 6B, pp. 4287-4292.
Gottlicher, M et al. (2001), "Valproic acid defines a novel class of HDAC inhibitors inducing differentiation of transformed cells," EMBO Journal, vol. 20, No. 24, pp. 6969-6978.
Graziano, M.J. and Casida, J.E. (1987) Toxicol Lett., 37:143-148.
Gumireddy, K., et al. (2003) "All-trans-Retinoic Acid-induced Apoptosis in Human Medulloblastoma: Activation of Caspase-3/ Poly(ADPribose) Polymerase 1 Pathway." Clinical Cancer Research, 9:4052-4059.
Havrilesky, LJ et al. (2001), "Relationship between expression of coactivators and corepressors of hormone receptors and resistance of ovarian cancers to growth regulation by steroid hormones," J. Soc. Gynecol. Investig., vol. 8, pp. 104-113.
Hermanson et al. (2002) "N-CoR controls differentiation of neural stem cells itno astrocytes," Nature, vol. 419 pp. 934-939.
Hirose, Y. et al. (2005) "Akt activation suppresses Chk2-mediated, methylating agent-induced G2 and protects from temozolomide-induced mitotic catastrophe and cellular senescence" Cancer Res. 65:4861-4869.
Honkanan, R.E. et al., (1993) "Cantharidin, another natural toxin that inhibits the activity of serinelthreonine protein phosphatases types 1 and 2A." FEBS Lett., 330, 283-286.
Hughes et al. (1988) "Ciliary neurotrophic factor induces type-2 astrocyte differentiation in culture." Nature, vol. 335, pp. 70-73.
Ianzini, F. and Mackey, MA. (1998) "Delayed DNA damage associated with mitotic catastrophe following X-irradiation of HeLa S3 cells" Mutagenesis 13:337-344.
Janssens, V. and Goris, J. (2001) "Protein phosphatases 2A: a highly regulated family of serine/threonin phosphatases implicated in cell growth and signaling" Biochemistry 353:417-439.
Johnson, T.M. et al. (2008) "Plk1 activation of Ste20-like Kinase (Slk) phosphorylation and polo-box phosphopeptide binding assayed with the substrate translationally controlled tumor protein (TCTP)" Biochemisty 47:3688-3696.
Joshi, S., et al. (2006) "Retinoic acid receptors and tissue-transglutaminase mediate short-term effect of retinoic acid on migration and invasion of neuroblastoma SH-SY5Y cells." Oncogene, 25:240-274.
Kamitami et al. (2002) "Histone acetylation may suppress human glioma cell proliferation when p21WAF/Cip1 and gelsolin are induced." Neuro-Oncology, Apr. 2002, pp. 95-101.

Kawamura, N. et al. (1990) "Endothall Thioerthydride: Structural Aspects of Unusually High Mouse toxicity and Specific Binding Site in Liver." Chem. Res. Toxicol., vol. 3, pp. 318-324.
Kayser, M.M. et al. (1982) Can. J. Chem. 60:1199-1208.
Kayser, M.M. et al. (1989) Can. J. Chem, 67:1401-1410.
Kelly et al. (2005) "Drug insight: histone deacetylase inhibitors-development of the new targeted anticancer agent suberoylanilide hydroxamic acid." Nature Clinical Practice Oncology, vol. 2, No. 3, pp. 150-157.
King, F.D. (1994), Med. Chem. Principle & Practive, Chapter 14, p. 206-209.
Kovach, JS, et al. (1985) "Enhancement of the antiproliferative activity of human interferon by polyamine depletion." Cancer Treat. Rep., vol. 69, pp. 97-103.
Langley et al. (2008) Pulse inhibition of histone deacetylases induces complete resistance to oxidative death in cortical neurons without toxicity and reveals a role for cytoplasmic p21waf1/cip1 in cell cycle-independent neuroprotection J. Neurosci., 28(1), pp. 163-176.
Lei, M. and Erickson, A.K. (2008) "Plk1 depletion in nontransformed diploid cells activates the DNA-damage checkpoint" Oncogene 27:3935-3943.
Li, X-N., et al. (2005) "Valproic acid induces growth arrest, apoptosis, and senescence in medulloblastomas by increasing histone hyperacetylation and regulating expression of p21Cip1, CDK4, and CMYC." Mol Cancer Ther., 4 (12):1912-1922.
Li, Y.M. et al. (1992) "Cantharidin-binding protein: Identification as protein phosphatase 2A." Proc . Natl. Acad. Sci. USA, 89, 11867-11870.
Li, Y.M. et al. (1993) Biochem. Pharmacol. 46:1435-1443.
Lim, K.H. et al. (2008) "Tumor maintenance is mediated by eNOS" Nature 452:646-9.
Liu, H. et al. (2005) "Stabilization and enhancement of the antiapoptic activity of Mcl-1 by TCTP" Molecular and Cellular Biology 25:3117-3126.
Liu, X. et al . (2006) "Normal cells, but not cancer cells, survive severe P1k1 depletion" Mol. & Cell. Biol. 26:2093-2108.
Lopez-Pajares, V. et al. (2008) "Phosphorylation of MDMX mediated by Akt leads to stabilization and induces 14-3-3 binding" J. Biol. Chem. 283:13707-13713.
Lu, J. et al. (2008) "LB-1 an inhibitor of serine-threonine protein phosphatase PP2A, suppresses the growth of glioblastoma cells in vitro and in vivo" 99h AACR annual meeting, Abstract #5693.
Lu, Shui-Yu et al. (1993) "Aqueous ring-opening metathesis polymerization and copolymerization of 2, 3-dicarboxylic acid anhydride, 2, 3-bis(methoxymethyl) and 2, 3-dicarboxylic acid monomethyl ester derivatives of 7-oxanorbornene" European Polymer Journal 29(2-3) 269-79.
Lu, Shui-Yu et al. (1994) "Aqueous ring-opening metathesis polymerization of 7-oxanobornene derivatives with oxygen-containing functionalities" Macromolecular Chemistry and Physics 195(4) 1273-88.
Manka, Jason T. et al. (2000) "Retro Diels-Alder Reactions of 5, 6-Disubstituted-7-oxabicyclo[2.2.1]hept-2-enes: Experimental and Density Functional Theory Studies" Journal of Organic Chemisty 65(17) 5202-5206.
Mardor et al. (2001) "Monitoring Response to Convection-enhanced Taxol delivery in brain tumor patients using diffusion-weighted magnetic resonance imaging" Cancer Res., 61, pp. 4971-4973.
Matsuzawa, M. et al. (1987), "Endothal and Cantharidin Analogues: Relation of Structure to Herbicidal Activity and Mammalian Toxicity," J. Agric. Food Chem., 35 (5), pp. 823-829.
Matthay, KK., et al. (1999) "Treatment of High-Risk Neuroblastoma With Intensive Chemotherapy, Radiotherapy, Autologous Bone Marrow Transplantation, and 13-Cis-Retinoic Acid." N. Engl. J Med.,341:1165-1173.
McCluskey et al. (1996) "Inhibition of Protein Phosphatase 2A by Cantharidin Analogues" Bioorg. Med. Chem. Lett., 6(9), pp. 1025-1028.
McCluskey et al. (2000) "Anhydride modified cantharidin analogues. Is ring opening important in the inhibition of protein phosphatase 2A?" Eur. J. Med. Chem., 35, pp. 957-964.

(56) References Cited

OTHER PUBLICATIONS

McCluskey et al. (2000) "Anhydride Modified Cantharidin Analogues: Synthesis, Inhibition of Protein Phosphatases 1 and 2A and Anticancer Activity" Bioorg. Med. Chem. Lett., 10, pp. 1687-1690.
Momparlet, RL. (1980), "In vitro systems for evaluation of combination chemotherapy," Pharmacol. Ther., vol. 8, pp. 21-35.
Morse, D.L. et al. (2005) "Docetaxel induces cell death through mitotic catastrophe in human breast cancer cells" Mol. Cancer Ther. 4:1495-1504.
Myers, E. et al. (2005) "Associations and Interactions Between Ets-1 and Ets-2 and Coregulatory Proteins, SRC-1, AIB1 and NCoR in Breast Cancer," Clin. Cancer Res., vol. 11, pp. 2111-2122.
Neviani, P. et al. (2007) "FTY720, a new alternative for treating blast crisis chronic myelogenous leukemia and Philadephia chromosome-positive acute lymphocytic leukemia" The Journal of Clinical Investigation 117:2408-2421.
Ngan, C.Y. et al. (2007) "Oxaliplatin induces mitotic catastrophe and apoptosis in esophageal cancer cells" Cancer Sci. 99:129-139.
Olivier, M. et al. (2008) "Recent advances in p53 research: an interdisciplinary perspective" Cancer Gene Therapy pp. 1-12.
Olmos, D. et al. (2008) "Targeting polo-like kinase: learning too little too late?" J. Clin. Oncology 27:5497-5499.
Park, DM. et al. (2007) N-CoR pathway targeting induces glioblastoma derived cancer stem cell differentiation, Cell Cycle, vol. 6, issue 4, pp. 467-470.
Peng, F. et al. (2002), "Induction of apoptosis by norcantharidin in human colorectal cell lines: involvement of the CD95 receptor/ligand," J. Cancer Res. Clin. Oncol., vol. 128, pp. 223-230.
Perrotti, D. and Neviani, P. (2008) "Protein phophatases 2A (PP2A), a drugable tumor suppressor in Ph1(+) leukemias" Cancer Metastasis, Rev. DOI 10.1007/S10555-008-9119.
Prados, M.D. et al. (2008) "Phase II study of Erlotinib plus temozomide during and after radation therapy in patients with newly diagnoses glioblastoma multiforme or gliosarcoma" J. Clin. Oncology pp. 1-6.
Price et al. (2007) "Histone deacetylase inhibitors: an analysis of recent patenting activity" Expert Opin. Ther. Patents, 17(7), pp. 745-765.
Ramezanian, M. et al., (1989) "A new super-electrophile: alpha-(phenylsulfonyl)maleic anhydride." J. Org. Chem., 54, 2852-2854.
Richon et al. (1998) "A class of hybrid polar inducers of transformed cell differentiation inhibits histone deacetylases" Proc. Natl. Acad. Sci. USA, 95(6), pp. 3003-3007.
Rinkenberger, J. et al. (1999) "Mcl-1 deficiency results in peri-implantation embryonic lethality" Genes and Development 14:23-27.
Rubie, H. et al. (2006) "Phase II study of temozolomide in ralapsed or refractory high-risk neuroblastoma: a joint Societe Francaise des Cancers de l'Enfant and United Kingdom Children Cancer Study Group-New Agents Group Study" J. Clin. Oncol. 24:5259-5264.
Registry (STN) Online, Nov. 16, 1984, CAS registered No. 57958-23-3 (Search Date Jan. 16, 2013).
CAS Registry No. 61531-23-5, Nov. 16, 1984 (discussed in the Dec. 6, 2012 Australian Office Action issued in connection with Australian Patent Application No. 2008214299).
Sahin et al. "Retinoic Acid Isomers Protect Hippocampal Neurons From Amyloid-beta Induced Neurodegeneration." Neurotoxicity Res., 2005, vol. 7(3), pp. 243-250.
Sakoff et al. (2002) "Anticancer activity and protein phosphatase 1 and 2A inhibition of a new generation of cantharidin analogues" Invest. New Drugs, 20, pp. 1-11.
Sakoff, JA. (2004) "Protein Phosphatase Inhibition: Structure Based Design, Towards New Therapeutic Agents," Current Pharmaceutical Design, vol. 10, pp. 1139-1159.
Sanderson, L et al. (2004), "Plasma Pharmacokinetics and Metabolism of the Histone Deacetylase Inhibitor Trichostatin A after Intraperitoneal Administration to Mice," Drug Metabolism and Disposition, vol. 32, No. 10, pp. 1132-1138.
Shimi, IR et al. (1982) European Journal of Cancer and Clinical Oncology 18:785-793.
Short, S.C. et al. (2007) "DNA repair after irradiation in glioma cells and normal human astrocytes" Neuro-Oncology 9:404-411.
Singh et al. (2003), "Identification of a cancer stem cell in human brain tumors," Cancer Research, vol. 63, pp. 5821-5828.
Singh et al. (2004), "Identification of human brain tumour initiating cells," Nature, vol. 432, pp. 396-401.
Smith, W. L., et al. (2002) "Histone deacetylase inhibitors enhance Candida albicans sensitivity to azoles and related antifungals: correlation with reduction in CDR and ERG upregulatian", Antimicrob. Agents Chemother., 46(11), pp. 3532-3539.
Song et al. (2002) "Synthesis and Biological Properties of Amino Acid Amide Ligand-Based Pyridinioalkanoyl Thioesters as Anti-HIV Agents" Bioorganic and Medicinal Chem., 10(5), pp. 1263-1273.
Strebhardt, K. and Ullrich, A. (2006) "Targeting polo-like kinase 1 for cancer therapy" Nature Reviews 6:321-330.
Stupp et al. (2005) "Radiotherapy plus Concomitant and Adjuvant Temozolomide for Glioblastoma." N. Engl. J. Med., vol. 352, pp. 987-996.
Susini, L. et al. (2008) "TCTP protects from apoptotic cell death by antagonizing bax function" Cell Death and Differentiation Cell Death and Differentiation, pp. 1-10.
Tanaka et al. (1962) Chem. Pharm. Bull. 10:556-62.
Toma et al. (2005) "Retinoids and human breast cancer: in vivo effects of an antagonist for RAR-α." Cancer Lett., 219, pp. 27-31.
Touma et al. (2005) "Retinoic acid and the histone deacetylase inhibitor Trichostatin A inhibit the proliferation of human renal cell carcinoma in a xenograph tumor model." Clin. Cancer Res., 11(9), pp. 3558-2566.
Trost L. (1977) J. Am. Chem. Soc. 99:7079.
Tuynder, M. et al. (2002) "Biological models and genes of tumor reversion: cellular reprogramming through tpt1/TCTP and SIAH-1" PNAS 9914697-14981.
Tuynder, M. et al. (2004) "Translationally controlled tumor protein is a target of tumor reversion" PNAS 101:15364-15369.
Uchida et al. (2000) "Direct isolation of human central nervous system stem cells." Proc. Natl. Acad. Sci. USA, vol. 97, pp. 14720-14725.
Valeriote, F. (1975), "Synergistic interaction of anticancer agents: A cellular perspective," Cancer Chemother. Rep., vol. 59, pp. 895-900.
Vazquez, A. et al. (2008) "The genetics of the p53 pathway, apoptosis and cancer therapy" Nature Rev. Cancer 7:979-987.
Wang, GS (1983), "Hydrolysis and demethylation of cantharidin on the relief of its urinary irritation," Chin. Pharmac. Bull., Col. 18, pp. 18-19, with English language title available from the journal and English language summary prepared at the applicants' attorneys' office.
Wang, GS (1989), "Medical uses of mylabris in ancient China and recent studies," J. Ethnopharmacol., vol. 26, pp. 147-162.
Wang, GS et al. (1986), "Results of clinical trials in 244 cases of primary hepatoma and with norcantharidin," Chinese. Pharm. Bull., vol. 21, pp. 90-93, with English translation of abstract prepared at the applicants' attorneys' office.
Wang, GS et al. (1987), "Effect of norcantharidin on the number of white blood cells," Chinese Pharm. Bull., vol. 22, pp. 517-519, with English translation of abstract prepared at the applicants' attorneys' office.
Warr, M. and Shore, G.C. (2008) "Unique Biology of Mcl-1: Therapeutic opportunities in cancer" Current Molecular Medicine 8:138-147.
Warrell, Jr. et al. (1998) "Therapeutic Targeting of Transcription in Acute Promyelocytic Leukemia by Use of an Inhibitor of Histone Deacetylase" J. Natl. Cancer Inst., 90, pp. 1621-1625.
Waters, CE et al. (2004), "Analysis of co-factor 10 function in glucocorticoid-resistant small cell carcinoma line," J. Endocrinol., vol. 183, pp. 375-383.
Weinmann et al. (2005) "Histone deacetylase inhibitors: a survey of recent patents." Expert Opin. Ther. Patents, 15(12), pp. 1677-1690.
Westermarck, J. et al. (2008) "Multiple pathways regulated by the tumor suppressor PP2A in transformation" Trends in Molecular Medicine, Trends in Molecular Medicine, 14, pp. 152-160.
Yur'ev et al. Chemical Abstracts vol. 56, No. 73368.

(56) References Cited

OTHER PUBLICATIONS

Stewart et al. (2007). Synthesis and biological evaluation of norcantharidin analogues: towards PP1 selectivity, *Bioorganic & Medicinal Chemistry*, 15, 7301-7310.
Yan et al. (1997). Inhibition of protein phosphatase activity induces p53-dependent apoptosis in the absence of p53 transactivation. *The Journal of Biological Chemistry*, 272 (24), 15220-15226.
Cho et al. (Jan. 2007). Crystal structure of a protein phosphatase 2A heterotrimeric holoenzyme. *Nature*, 445, 53-57.
Hart et al. (2004). Modified norcantharidins : synthesis, protein phosphatases 1 and 2A inhibition, and anticancer activity. *Bioorganic & Medicinal Chemistry Letters*, 14, 1969-1973.
Dreesen et al. (2007). Signaling pathways in cancer and embryonic stem cells. *Stem Cell Rev*, 3(1), 7-17.
Sridharan et al. (Apr. 2008). Illuminating the black box of reprogramming. *Cell Stem Cell*, 2(4), 295-297.
Hill et al. (2007) "Heterocyclic substituted cantharidin and norcantharidin analogues—synthesis, protein phosphatase (1 and 2A) inhibition, and anti-cancer activity" Bioorg. Med. Chem. Lett., 17, pp. 3392-3393.
Yang, Y. et al. (2005) "An N-terminal region of translationally controlled tumor protein is required for its antiapoptic activity" Oncogene 24:4778-4788.
Yarm, F.R. (2002) "Plk phosphorylation regulates the microtubule-stabilizing protein TCTP" Molecular and Cellular Biology 22:6209-6621.
Yuir'ev et al. Chemical Abstracts vol. 56, No. 73368 (1961).
Non-final Office Action issued Oct. 26, 2010 in connection with U.S. Appl. No. 12/069,147.
Non-final Office Action issued Jan. 4, 2011 in connection with U.S. Appl. No. 12/069,147.
Non final Office action issued Aug. 20, 2012 in connection with U.S. Appl. No. 13/174,249.
Notice of Allowance issued Dec. 28, 2012 in connection with U.S. Appl. No. 13/174,249.
Notification of Transmittal of the International Search Report and the Written Opinion of the International Searching Authority, or the Declaration in connection with PCT/US08/01549, issued May 16, 2008.
International Search Report in connection with PCT/US08/01549, issued May 16, 2008.
Written Opinion in connection with PCT/US08/01549, issued May 16, 2008.
Notification Concerning Transmittal of International Preliminary Report on Patentability in connection with PCT/US2008/001549, issued Aug. 11, 2009.
International Preliminary Report on Patentability in connection with PCT/US2008/001549, issued Aug. 11, 2009.
Supplemental European Search Report issued Mar. 9, 2011 in connection with European Patent Application No. 08725214.4, filed Sep. 2, 2009.
Communication pursuant to Rules 70(2) and 70a(2) EPC issued Mar. 28, 2011 in connection with European Patent Application No. 08725214.4, filed Sep. 2, 2009.
Communication pursuant to Art. 94(3)EPC issued Dec. 12, 2012 in connection with European Patent Application No. 08725214.4, filed Sep. 2, 2009.
Eurasian Official Action issued Jun. 22, 2011 in connection with Eurasian Patent Application No. 200970737 with English translation.
Eurasian Official Action issued Nov. 19, 2009 in connection with Eurasian Patent Application No. 200970737.
Eurasian Official Action issued May 24, 2012 in connection with Eurasian Patent Application No. 200970737 with English translation.
Eurasian Official Action issued Feb. 15, 2013 in connection with Eurasian Patent Application No. 200970737 with English translation.
Mexican Office Action issued Mar. 23, 2012 in connection with Mexican Patent Application No. MX/a/2009/008347 including English language summary provided by Mexican agent.
Mexican Office Action issued Jun. 4, 2012 in connection with Mexican Patent Application No. MX/a/2009/008347 including English language summary provided by Mexican agent.
Mexican Office Action issued Aug. 15, 2012 in connection with Mexican Patent Application No. MX/a/2009/008347 including English language summary provided by Mexican agent.
Mexican Office Action issued Jan. 24, 2013 in connection with Mexican Patent Application No. MX/a/2009/008347 including English language summary provided by Mexican agent.
Chinese Office Action issued May 21, 2012 in connection with Chinese Patent Application No. 200880004292.9 including English language summary provided by Chinese agent.
Chinese Office Action issued Jan. 14, 2013 in connection with Chinese Patent Application No. 200880004292.9, including English language translation provided by Chinese Agent.
Japanese Office Action issued Jan. 22, 2013 in connection with Japanese Patent Application No. 2009-549092.
Australian Office Action issued Dec. 6, 2012 in connection with Australian Patent Application No. 2008214299.
Non-final Office Action issued Feb. 16, 2011 in connection with U.S. Appl. No. 12/221,360.
Non-final Office Action issued May 26, 2011 in connection with U.S. Appl. No. 12/221,360.
Final Office Action issued Nov. 2, 2011 in connection with U.S. Appl. No. 12/221,360.
Advisory Action issued Jan. 13, 2012 in connection with U.S. Appl. No. 12/221,360.
Notification of Transmittal of the International Search Report and the Written Opinion of the International Searching Authority, or the Declaration in connection with PCT/US08/09330, issued Nov. 4, 2008.
International Search Report in connection with PCT/US08/09330, issued Nov. 4, 2008.
Written Opinion in connection with PCT/US08/09330, issued Nov. 4, 2008.
Supplemental European Search Report in connection with EP 08794986.3, issued Dec. 15, 2010.
Oct. 4, 2011 Communication issued in connection with European Patent Application No. 08794986.3.
Nov. 9, 2012 Patent Examination Report issued in connection with Australian Patent Application No. 2008284364.
Non-final Office Action issued Sep. 30, 2010 in connection with U.S. Appl. No. 12/460,407.
Non-final Office Action issued Feb. 16, 2011 in connection with U.S. Appl. No. 12/460,407.
Notification of Transmittal of the International Search Report and the Written Opinion of the International Search Authority, or the Declaration, in connection with PCT/US09/04108, issued Sep. 15, 2009.
International Search Report in connection with PCT/US09/04108, issued Sep. 15, 2009.
Written Opinion in connection with PCT/US09/04108, issued Sep. 15, 2009.
Notification of Transmittal of the International Preliminary report on patentability, in connection with PCT/US09/04108, issued Feb. 10, 2011.
Non-final Office Action issued Aug. 3, 2011 in connection with U.S. Appl. No. 12/460,404.
Final Office Action issued Dec. 15, 2011 in connection with U.S. Appl. No. 12/460,404.
Advisory Action issued Feb. 22, 2012 in connection with U.S. Appl. No. 12/460,404.
Restriction Requirement issued May 18, 2011 in connection with U.S. Appl. No. 12/460,404.
Notice of Allowance issued Mar. 19, 2012 in connection with U.S. Appl. No. 12/460,404.
Restriction Requirement issued Sep. 28, 2012 in connection with U.S. Appl. No. 13/493,816.
Non Final Office Action issued Nov. 20, 2012 in connection with U.S. Appl. No. 13/493,816.

(56) References Cited

OTHER PUBLICATIONS

Final Office Action issued Mar. 20, 2013 in connection with U.S. Appl. No. 13/493,816.
Notification of Transmittal of the International Search Report and the Written Opinion of the International Search Authority, or the Declaration, in connection with PCT/US09/04430, issued Jan. 12, 2010.
International Search Report in connection with PCT/US09/04430, issued Jan. 12, 2010.
Written Opinion in connection with PCT/US09/04430, issued Jan. 12, 2010.
Notification of Transmittal of the International Preliminary report on patentability, in connection with PCT/US09/04430, issued Feb. 10, 2011.
International Preliminary Report on Patentability in connection with PCT/US09/04430, issued Feb. 1, 2011.
Patent Search Report Issued Oct. 25, 2011 in connection with Eurasian Patent Application No. 201170288, filed Jul. 30, 2009.
Eurasian Official Action issued Nov. 19, 2012 in connection with Eurasian Patent Application No. 201170288, filed Jul. 30, 2009 with English translation.
Supplemental European Search Report and European Search Opinion issued Apr. 2, 2012 in connection with European Patent Application No. 09803283.2, filed Jan. 24, 2011.
Communication pursuant to Art. 94(3)EPC issued Jan. 30, 2013 in connection with European Patent Application No. 09803283.2, filed Jan. 24, 2011.
Mexican Office Action issued Jul. 19, 2012 in connection with Mexican Patent Application No. MX/a/2011/001007, filed Jan. 26, 2011 including English language summary provided by Mexican agent.
Mexican Office Action issued Sep. 25, 2012 in connection with Mexican Patent Application No. MX/a/2011/001007, filed Jan. 26, 2011 including English language summary provided by Mexican agent.
Mexican Office Action issued Mar. 25, 2013 in connection with Mexican Patent Application No. MX/a/2011/001007, filed Jan. 26, 2011 including English language summary provided by Mexican agent.
Notification Concerning Transmittal of International Preliminary Report on Patentability in connection with PCT/US2010/0002795, issued Jan. 5, 2012.
International Search Report, mailed May 3, 2010 in connection with PCT International Application No. PCT/US2010/000279, filed Feb. 1, 2010.
Written Opinion of the International Searching Authority, mailed May 3, 2010 in connection with PCT International Application No. PCT/US2010/000279, filed Feb. 1, 2010.
Notice of Allowance mailed Apr. 6, 2011 in connection with U.S. Appl. No. 12/069,147.
Non final Office action issued Sep. 16, 2013 in connection with U.S. Appl. No. 13/866,854.
Final Office action issued Jan. 16, 2014 by the U.S. Patent Office in connection with U.S. Appl. No. 13/866,854.
Notice of Allowance issued Apr. 2, 2014 by the U.S. Patent Office in connection with U.S. Appl. No. 13/866,854.
Eurasian Official Action issued Sep. 19, 2013 in connection with Eurasian Patent Application No. 200970737 (including English language summary provided by Eurasian agent).
Decision of Rejection issued Aug. 22, 2013 by the Chinese Patent Office in connection with Chinese Patent Application No. 200880004292.9 (including English language summary provided by Chinese agent).
Japanese Office Action issued Sep. 10, 2013 in connection with Japanese Patent Application No. 2009-549092 (including English language summary provided by Japanese agent).
Office Action Issued Dec. 20, 2013 by the Canadian Patent Office in connection with Canadian Patent Application No. 2,67,422.
Jul. 4, 2013 Communication Pursuant to Article 94(3)EPC issued by the European Patent Office in connection with European Patent Application No. 08794986.3.
Nov. 9, 2012 Examination Report issued in connection with Australian Patent Application No. 2008284364.
Notice of Allowance mailed May 23, 2013 in connection with U.S. Appl. No. 13/493,816.
First Examiner's Report issued Sep. 27, 2013 by the Australian Patent Office in connection with Australian Patent Application No. 2009277031, filed Jan. 11, 2011.
First Official Action issued Jul. 1, 2013 in connection with Chinese Patent Application No. 200980130568.2 (including English language summary provided by Chinese agent).
Second Official Action issued Mar. 20, 2014 in connection with Chinese Patent Application No. 200980130568.2 (including English language summary provided by Chinese agent).
Eurasian Official Action issued Jun. 7, 2013 in connection with Eurasian Patent Application No. 201170288, filed Jul. 30, 2009 (including English language summary provided by Eurasian agent).
Eurasian Official Action issuedCed. 23, 2013 in connection with Eurasian Patent Application No. 201170288 (including English language summary provided by Eurasian agent).
Communication pursuant to Art. 94(3)EPC issued Jul. 16, 2013 in connection with European Patent Application No. 09803283.2, filed Jan. 24, 2011.
Communication pursuant to Art. 94(3)EPC issued Mar. 4, 2014 in connection with European Patent Application No. 09803283.2.
Office Action issued Dec. 17, 2013 by the Japanese Patent Office in connection with Japanese Patent Application No. 2011-521128 (including English language summary provided by Japanese agent).
Eurasian Official Action issued Apr. 8, 2014 in connection with Eurasian Patent Application No. 200970737 including English translation.
Reexamination Decision issued Mar. 26, 2014 by the Chinese Patent Office in connection with Chinese Patent Application No. 200880004292.9.
Chinese Office Action issued Jul. 8, 2014 in connection with Chinese Patent Application No. 200880004292.9, including English language translation provided by Chinese Agent.
Eurasian Official Action issued Jun. 27, 2014 in connection with Eurasian Patent Application No. 201170288 (including English language summary of Official Action provided by Eurasian agent).
Mexican Office Action issued May 14, 2014 in connection with Mexican Patent Application No. MX/a/2011/001007, including English language summary provided by Mexican agent.
Decision of Rejection issued May 27, 2014 by the Japanese Patent Office in connection with Japanese Patent Application No. 2011-521128 (Including English Language Translation Provided by Japanese Agent).
May 15, 2013 Office Action issued in connection with U.S. Appl. No. 13/378,623.
Office Action issued Aug. 20, 2013 in connection with U.S. Appl. No. 13/378,623.
Amendment in Response to Aug. 20, 2013 Office Action filed Nov. 20, 2013 with the U.S. Patent and Trademark Office in connection with U.S. Appl. No. 13/378,623.
Final Office Action issued Jan. 27, 2014 in connection with U.S. Appl. No. 13/378,623.
Amendment in Response to Jan. 27, 2014 Final Office Action filed Apr. 10, 2014 with the U.S. Patent and Trademark Office in connection with U.S. Appl. No. 13/378,623.
Advisory Action issued Apr. 16, 2014 in connection with U.S. Appl. No. 13/378,623.
Amendment as a Submission Accompanying a Request for Continued Examination Under 37 C.F.R. §1.114 in Response to Jan. 27, 2014 Final Office Action and Apr. 16, 2014 Advisory Action filed Apr. 28, 2014 with the U.S. Patent and Trademark Office in connection with U.S. Appl. No. 13/378,623.
Communication pursuant to Art. 94(3)EPC issued Oct. 8, 2014 in connection with European Patent Application No. 08725214.4, filed Sep. 2, 2009.

(56) References Cited

OTHER PUBLICATIONS

Japanese Office Action issued Apr. 15, 2014 in connection with Japanese Patent Application No. 2009-549092 (Including English Language Translation).
Japanese Office Action issued Aug. 26, 2014 in connection with Japanese Patent Application No. 2009-599092 (Including English Language Translation).
Office Action Issued Jul. 30, 2014 by the Canadian Patent Office in connection with Canadian Patent Application No. 2,67,422.
Third Official Action (including English translation thereof) issued Sep. 28, 2014 in connection with Chinese Patent Application No. 200980130568.2.
International Search Report issued Aug. 25, 2014 in connection with PCT International Application No. PCT/US14/33317.
Notice of Allowance issued Mar. 4, 2015 by the U.S. Patent Office in connection with U.S. Appl. No. 14/328,384.
Communication pursuant to Art. 94(3)EPC issued Jan. 15, 2016 in connection with European Patent Application No. 08725214.4, filed Sep. 2, 2009.
Eurasian Official Action issued Nov. 25, 2014 in connection with Eurasian Patent Application No. 200970737 including English language summary provided by Eurasian agent.
Chinese Office Action issued Jan. 20, 2015 in connection with Chinese Patent Application No. 200880004292.9, including English language summary provided by Chinese Agent.
Chinese Office Action issued Apr. 30, 2015 in connection with Chinese Patent Application No. 200880004292.9, including English language summary provided by Chinese Agent.
Chinese Office Action issued May 25, 2015 in connection with Chinese Patent Application No. 201310655668.5, including English language summary provided by Chinese agent.
Chinese Office Action issued Jan. 22, 2016 in connection with Chinese Patent Application No. 201310655668.5, including English language summary provided by Chinese Agent.
Office Action issued Apr. 10, 2015 by the Canadian Patent Office in connection with Canadian Patent Application No. 2,676,422.
Office Action issued Dec. 18, 2015 by the Canadian Patent Office in connection with Canadian Patent Application No. 2,676,422.
Decision of Rejection issued Apr. 17, 2015 in connection with Chinese Patent Application No. 200980130568.2.
Notification of Reexamination issued Feb. 14, 2016 in connection with Chinese Patent Application No. 200980130568.2 (including English summary thereof provided by Chinese agent).
Mexican Office Action issued Nov. 22, 2013 in connection with Mexican Patent Application No. MX/a/2011/001007, filed Jan. 26, 2011.
Chang, Q., et al. (2007) "All-trans-retinoic acid induces cell growth arrest in a human medulloblastoma cell line" J. Neurooncol, 84:263-267.

* cited by examiner

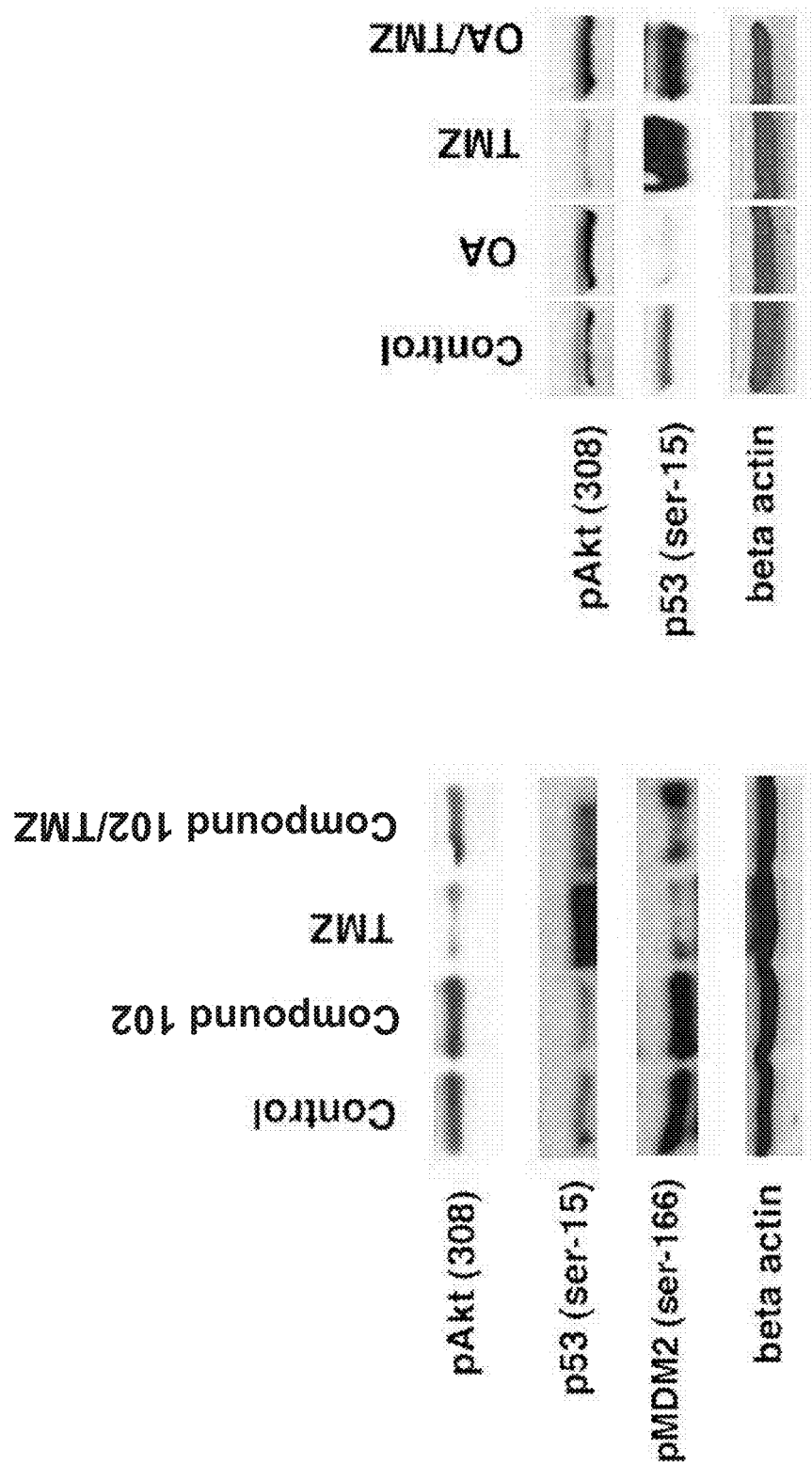

G1: 68.91
S: 9.69
G2/M: 20.8

Control

G1: 59.47
S: 12.61
G2/M: 27.28

Compound 102
5.0 uM

G1: 61.83
S: 17.60
G2/M: 18.67

TMZ 25 uM

G1: 54.67
S: 18.54
G2/M: 28.30

Compound 102/TMZ

G1: 54.94
S: 38.43
G2/M: 1.00

Dox 2.0 uM

G1: 53.42
S: 19.67
G2/M: 25.89

Compound 102/Dox

Control

G1: 72.41
S: 10.76
G2/M: 15.64

**Compound 102
5 uM**

G1: 71.41
S: 5.87
G2/M: 21.01

TMZ 25 uM

G1: 51.41
S: 36.58
G2/M: 10.30

Compound 102/TMZ

G1: 57.05
S: 12.42
G2/M: 28.43

Dox 2.0 uM

G1: 60.91
S: 21.95
G2/M: 16.82

Compound 102/Dox

G1: 61.54
S: 14.89
G2/M: 25.11

METHODS FOR REGULATING CELL MITOSIS BY INHIBITING SERINE/THREONINE PHOSPHATASE

This application is a continuation of U.S. Ser. No. 13/378,623, which is a §371 national stage of PCT International Application No. PCT/US2010/000279, filed Feb. 1, 2010, which claims benefit of U.S. Provisional Application No. 61/269,101, filed Jun. 18, 2009, and which is a continuation-in-part of PCT International Application No. PCT/US2009/004108, filed Jul. 16, 2009, which claims benefit of each of U.S. Provisional Application No. 61/269,101, filed Jun. 18, 2009 and 61/137,715, filed Aug. 1, 2008, the contents of each of which in its entirety is hereby incorporated by reference.

Parts of this invention were created in collaboration with the National Institutes of Health. The Government of the United States has certain rights in the invention.

Throughout this application, certain publications are referenced. Full citations for these publications may be found immediately preceding the claims. The disclosures of these publications in their entireties are hereby incorporated by reference into this application in order to describe more fully the state-of-the art to which this invention relates.

BACKGROUND OF THE INVENTION

Most current strategies for pharmacologic treatment of cancers are based on developing drugs or biologicals, primarily antibodies and anti-sense RNAs that specifically inhibit the activity of an enzyme in a signaling pathway or a gene encoding an enzyme upon which the cancer cell is dependent for growth and survival (Shoshan and Linder 2008). Dependence of a particular type of cancer on excessive activity of a specific signaling pathway has been termed "oncogene addiction" (Lim et al 2008). Interference with the function or abundance of an addicting oncogene may inhibit growth and, in some cases, result in the death of cancer cells that are dependent upon the pathway. Inhibition of a single oncogene, however, is usually insufficient for complete inhibition of a cancer and inhibition is overcome by mutation leading to drug resistance. Older approaches to cancer treatment have involved primarily the use of non-specific agents alone and in combinations of drugs with non-overlapping toxicities to normal tissues that damage DNA or interfere with cell metabolic pathways including modulation of microtubule stability.

A variety of mechanisms maintain the integrity of the genome of normal cells in the face of stress. DNA-damage response mechanisms, however, may also protect cancer cells from killing by chemotherapy and radiation, allowing cancers to recur despite aggressive treatment. Cell responses to DNA-damage are mediated in part by polo-like kinase 1 (Plk-1) (Strebhardt and Ullrich, 2006), Akt-1 (protein kinase B) (Brazil et al, 2004) and p53 (Vogelstein et al 2000; Vazquez et al 2008), pathways, which lead to cell cycle arrest, senescence, or apoptosis. Because many cancers over-express Plk-1 (Lei and Erikson, 2008; Olmos et al, 2008; Liu et al, 2006) and Akt-1 (Garcia-Echeverria and Sellers, 2008; Hirose et al 2005) or have acquired p53 (Vazquez et al, 2008) genetic defects, inhibition of Plk-1 (Strebhardt and Ullrich, 2006; Olmos et al, 2008; Liu et al, 2006) and Akt-1 (Garcia-Echeverria and Sellers, 2008; Hirose et al, 2005) and the restoration of p53 function (Vazquez et al, 2008) are being widely investigated as cancer treatments.

Translationally controlled tumor protein (TCTP) is one of the most highly conserved and most abundant proteins in eukaryotic cells (Bommer and Thiele, 2004). TCTP is associated with many cellular functions and is essential for fetal development (Bommer and Thiele, 2004; Chen et al, 2007B). TCTP is also essential to cancer cell growth but is not critical to the survival of normal adult (untransformed) cells (Chen et al, 2007). Disclosed herein is that targeting of TCTP with a pharmacologic intervention may be an effective means for disrupting cancer cell division and therefore for treating cancers in general.

SUMMARY OF THE INVENTION

The invention provides a method of inhibiting proliferation of a cancer cell or inducing apoptosis of a cancer cell, which cancer cell does not overexpress N—CoR, comprising administering to the subject a compound, wherein the compound has the structure

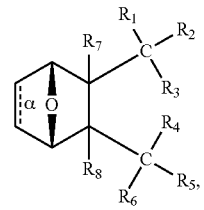

wherein bond α is present or absent; $R_1$ and $R_2$ is each independently H, $O^-$ or $OR_9$, where $R_9$ is H, alkyl, alkenyl, alkynyl or aryl, or $R_1$ and $R_2$ together are =O; $R_3$ and $R_4$ are each different, and each is OH, $O^-$, $OR_9$, SH, $S^-$, $SR_9$,

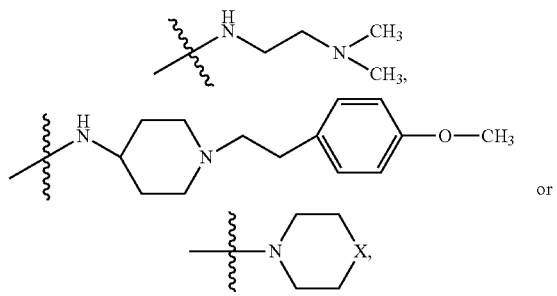

or where X is O, S, $NR_{10}$, or $N^+R_{10}R_{10}$, where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

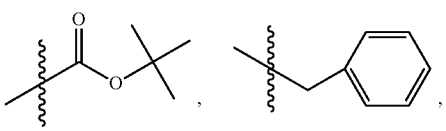

—$CH_2CN$, —$CH_2CO_2R_{11}$, —$CH_2COR_{11}$, —$NHR_{11}$ or —$NH^+(R_{11})_2$, where each $R_{11}$ is independently alkyl, alkenyl or alkynyl, each of which is substituted or unsubstituted, or H; $R_5$ and $R_6$ is each independently H, OH, or $R_5$ and $R_6$ taken together are =O; and $R_7$ and $R_8$ is each independently H, F, Cl, Br, $SO_2Ph$, $CO_2CH_3$, or $SR_{12}$, where $R_{12}$ is H, aryl or a substituted or unsubstituted alkyl, alkenyl or alkynyl, or a salt, enantiomer or zwitterion of the compound, in an amount effective to inhibit the proliferation or to induce apoptosis of the cancer cell.

The invention provides a method of inhibiting proliferation or inducing apoptosis of a cancer cell which overexpresses TCTP comprising administering to the subject a compound, wherein the compound had the structure

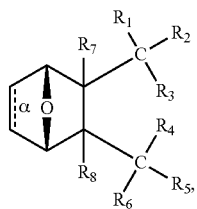

wherein bond α is present or absent; $R_1$ and $R_2$ is each independently H, O⁻ or $OR_9$, where $R_9$ is H, alkyl, alkenyl, alkynyl or aryl, or $R_1$ and $R_2$ together are =O; $R_3$ and $R_4$ are each different, and each is OH, O⁻, $OR_9$, SH, S⁻, $SR_9$,

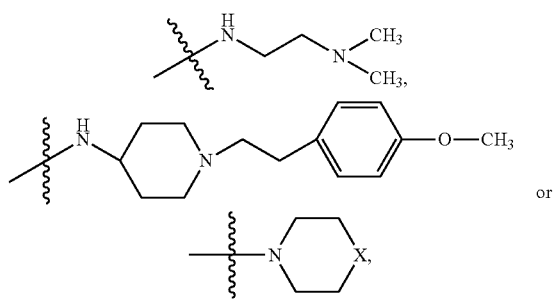

where X is O, S, $NR_{10}$, or $N^+R_{10}R_{10}$, where each $R_{10}$ is independently H, $C_2$-$C_{12}$ alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

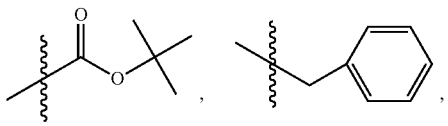

—$CH_2CN$, —$CH_2CO_2R_{11}$, —$CH_2COR_{11}$, —$NHR_{11}$ or —$NH^+(R_{11})_2$, where each $R_{11}$ is independently alkyl, alkenyl or alkynyl, each of which is substituted or unsubstituted, or H; $R_5$ and $R_6$ is each independently H, OH, or $R_5$ and $R_6$ taken together are =O; and $R_7$ and $R_8$ is each independently H, F, Cl, Br, $SO_2Ph$, $CO_2CH_3$, or $SR_{12}$, where $R_{12}$ is H, aryl or a substituted or unsubstituted alkyl, alkenyl or alkynyl, or a salt, enantiomer or zwitterion of the compound, in an amount effective to inhibit the proliferation or to induce apoptosis of the cancer cell.

The invention provides a method of inhibiting proliferation or inducing apoptosis of a cancer cell that overexpresses TCTP by administering to the subject a compound, wherein the compound has the structure

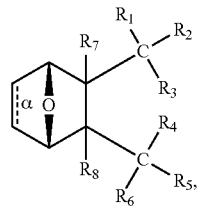

wherein bond α is present or absent; $R_1$ and $R_2$ is each independently H, O⁻ or $OR_9$, where $R_9$ is H, alkyl, alkenyl, alkynyl or aryl, or $R_1$ and $R_2$ together are =O; $R_3$ and $R_4$ are each different, and each is OH, O⁻, $OR_9$, SH, S⁻, $SR_9$,

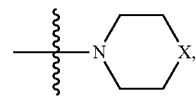

where X is O, S, $NR_{10}$, or $N^+R_{10}R_{10}$, where each $R_{10}$ is independently $C_2$-$C_{12}$ alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O, —$CH_2CN$, —$CH_2CO_2R_{11}$, —$CH_2COR_{11}$, —$NHR_{11}$ or —$NH^+(R_{11})_2$, where each $R_{11}$ is independently alkyl, alkenyl or alkynyl, each of which is substituted or unsubstituted, or H; $R_5$ and $R_6$ is each independently H, OH, or $R_5$ and $R_6$ taken together are =O; and $R_7$ and $R_8$ is each independently H, F, Cl, Br, $SO_2Ph$, $CO_2CH_3$, or $SR_{12}$, where $R_{12}$ is H, aryl or a substituted or unsubstituted alkyl, alkenyl or alkynyl, or a salt, enantiomer or zwitterions of the compound, in an amount effective to inhibit the proliferation or to induce apoptosis of the cancer cell.

This invention provides a method for determining whether a compound is effective in inducing cell death comprising (a) contacting a first cancer cell with the compound; (b) determining the level of expression of TCTP in the first cancer cell; (c) contacting a second cancer cell with a protein phosphatase 2A inhibitor (d) determining the level of expression of TCTP in the second cancer cell; (e) comparing the level of expression of TCTP determined in step (b) with the level determined in step (d), wherein, when the level of expression determined in step (b) is equal to, or lower than, the level of expression determined in step (d) indicates that the compound is effective to induce cell death.

This invention provides a method for determining whether a compound is effective in inducing cell death in a cancer cell comprising (a) contacting a cancer cell with the compound; (b) determining the level of expression of TCTP in the cancer cell; (c) determining the level of expression of TCTP in a non-cancerous cell; (e) comparing the level of expression of TCTP determined in step (b) with the level determined in step (d), wherein, when the level of expression determined in step (b) is lower than, the level of expression determined in step (d) indicates that the compound is effective to induce cell death in the cancer cell.

This invention provides a method for determining whether treatment of a subject with an agent will be successful in treating a subject suffering from cancer comprising (a) obtaining a first sample from the subject prior to treatment; (b) determining the level of expression of TCTP in the sample; (c) administering to the subject the agent; (d) obtaining a second sample from the subject after treatment with the agent; (e) determining the level of expression of TCTP in the second sample obtained; wherein, when the level of expression determined in step (b) is lower than the level of expression determined in step (e) indicates that the treatment of the subject with the agent be successful.

This invention provides a method for predicting whether treatment of a subject with an agent will be successful in treating a subject suffering from cancer comprising (a) obtaining a sample comprising cancer cells from the subject; (b) culturing the cancer cells; (c) determining the level of expression of TCTP in the cancer cells (d) contacting the cancer cells with the agent; (e) determining the level of expression of TCTP in the cancer cells; (f) comparing the level of expression of TCTP determined in step (c) with the level of expression determined in step (e); wherein, when the level of expression determined in step (c) is lower than the level of expression determined in step (e) predicts that treatment of the subject with the agent will be successful in treatment of the cancer.

This invention provides a method for reducing the amount of TCTP in a cell comprising contacting the cell with an effective amount of protein phosphatase inhibitor, thereby reducing the amount of TCTP in the cell.

Cultured DAOY cells were plated in 175 cm$^3$ flasks. When the cells were 80% confluent, the media was replaced with media containing either 0.15 μM Compound 102, 0.25 μM Compound 102, 0.3 μM Compound 102, or an equivalent volume of PBS vehicle. After 1 hour, the cells were washed three times in a 0.9% normal saline solution. T-PER solution was added to the cells, and cells were prepared for protein extraction. Lysates from each treatment group containing 300 μg of protein were applied to a spin column (Catch and Release v2.0 Reversible Immunoprecipitation System, Millipore, Billerica, Mass.) for immunoprecipitation of PP2A/Akt-1 kinase protein complexes using polyclonal anti-rabbit Akt-1 antibody (Cell Signaling Technology, Danvers, Mass.). PP2A activity from the immunoprecipitated complexes was assayed using a Malachite Green Phosphatase Assay specific for serine/threonine phosphatase activity (Ser/Thr Phosphatase Assay Kit 1, Millipore, Billerica, Mass.).

Figure 2:
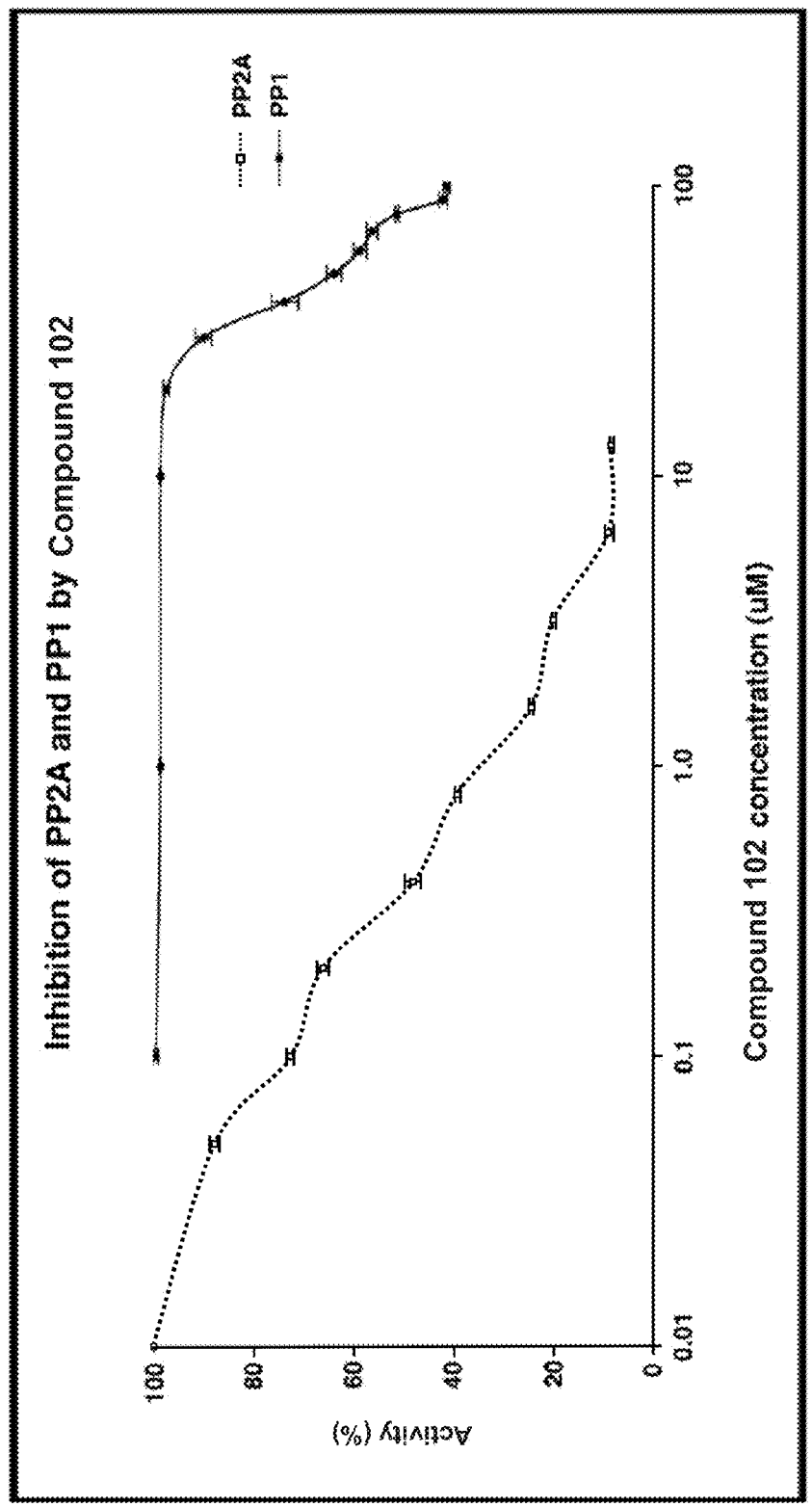

FIG. 2: Inhibition of Serine/Threonine Phosphatase Activity by Compound 102.

Inhibition of PP2A and PP1 activity by compound 102 on purified PP1 and PP2A (mean and s.d.; n=3) (Ser/Thr Phosphatase Assay Kit 1, Millipore, Billerica, Mass.).

Figure 3:
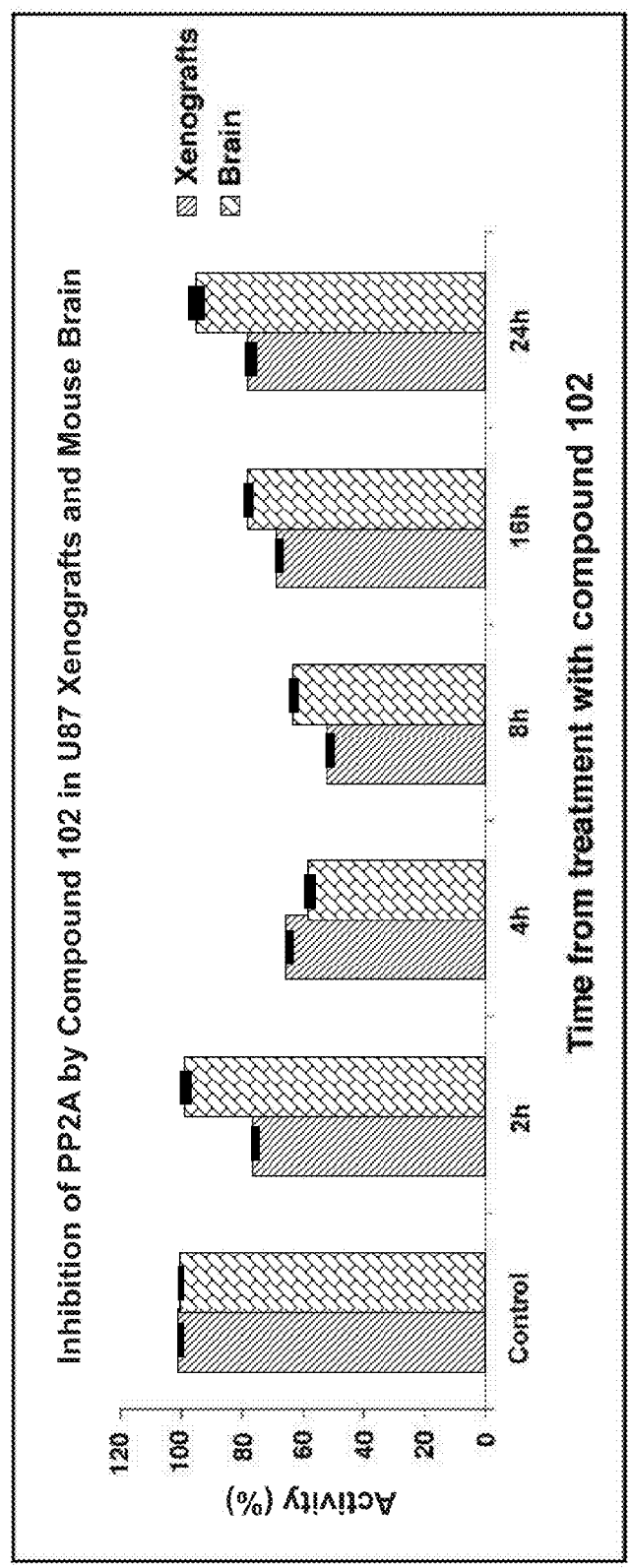

FIG. 3: Inhibition of Proliferation of U87 Cells by Compound 102.

PP2A activity in U87 s.c. xenografts (blue) and in normal brain tissue (yellow) of SCID mice at different times after i.p. injection of 1.5 mg/kg compound 102 (one mouse per point; each lysate was measured in triplicate: mean and s.d.)

Figure 4:
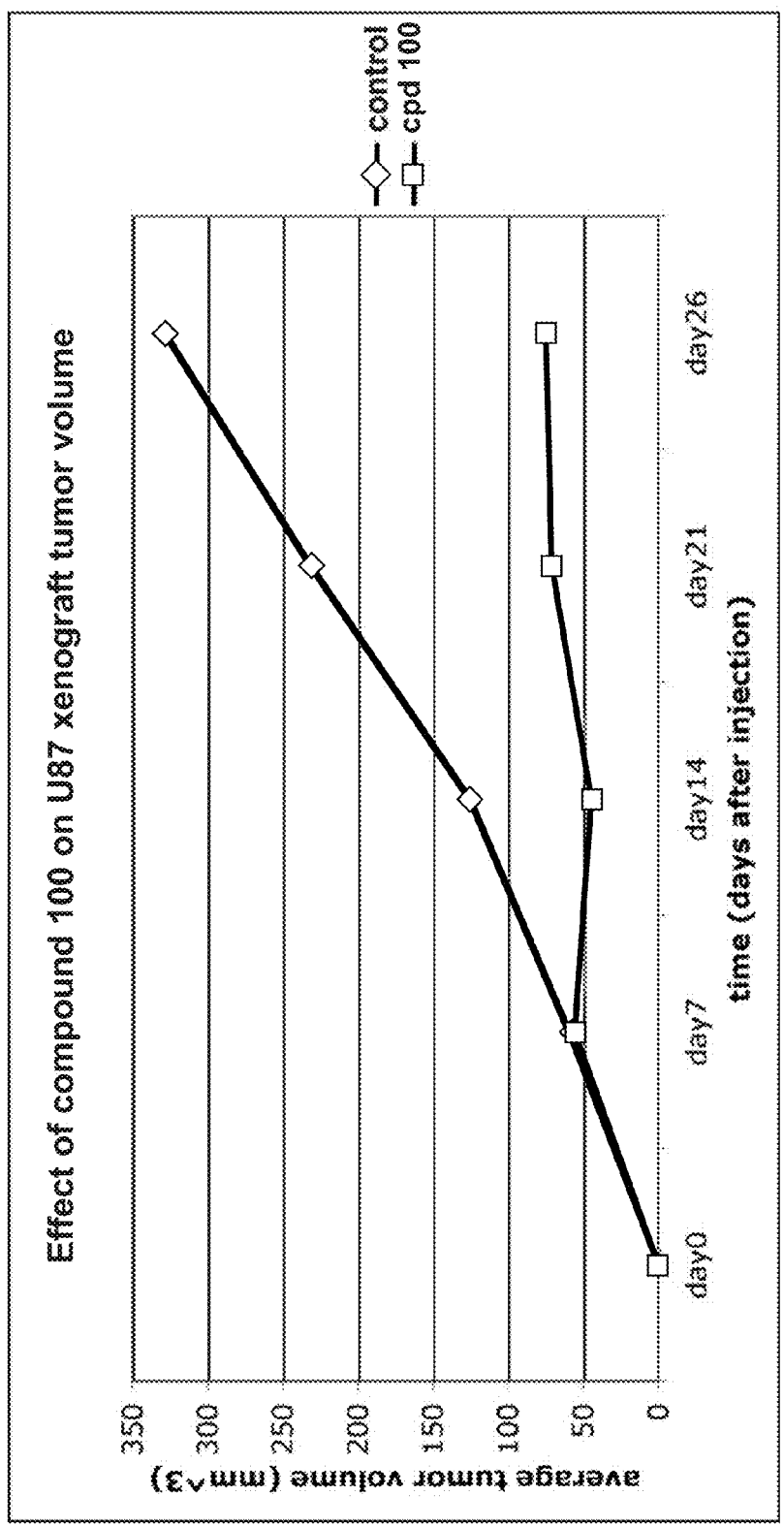

FIG. 4: Inhibition of U87 Glioblastoma Multiforme Cells Grown as Subcutaneous Xenografts in SCID Mice by Compound 100.

SCID mice were implanted with 5×10$^6$ U87 cells subcutaneously. On day 7 treatment was begun on half of the animals. The size of the subcutaneous mass of tumor cells was measured weekly until the animals were sacrificed on day 26.

Figure 5:
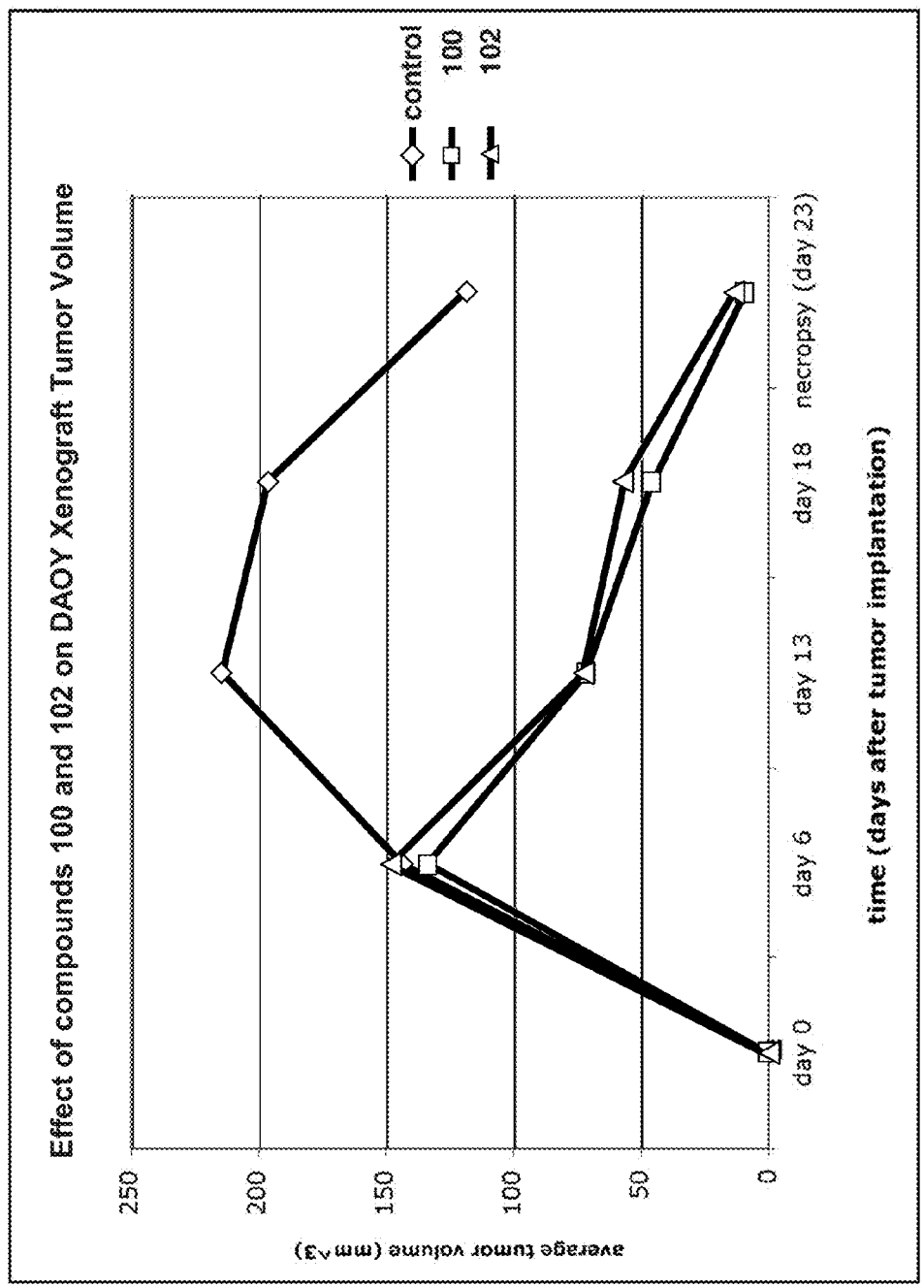

FIG. 5: Inhibition of DAOY Medulloblastoma Cells Grown as Subcutaneous Xenografts in SCID Mice by Compound 100 and Compound 102.

DAOY medulloblastoma cells were implanted subcutaneously into the flanks of SCID mice. On day 6, mice were divided into 3 groups, one group receiving Compound 100, one group receiving Compound 102, and one group receiving vehicle alone. The subcutaneous tumor masses were measured on day 6, day 13, day 18, and on day 23 when all animals were sacrificed. Both compounds led to marked regression of the tumor by day 23. In this model DAOY cells, when untreated, reached their maximum growth about 2 weeks after implantation with slow regression thereafterwards.

Figure 6:
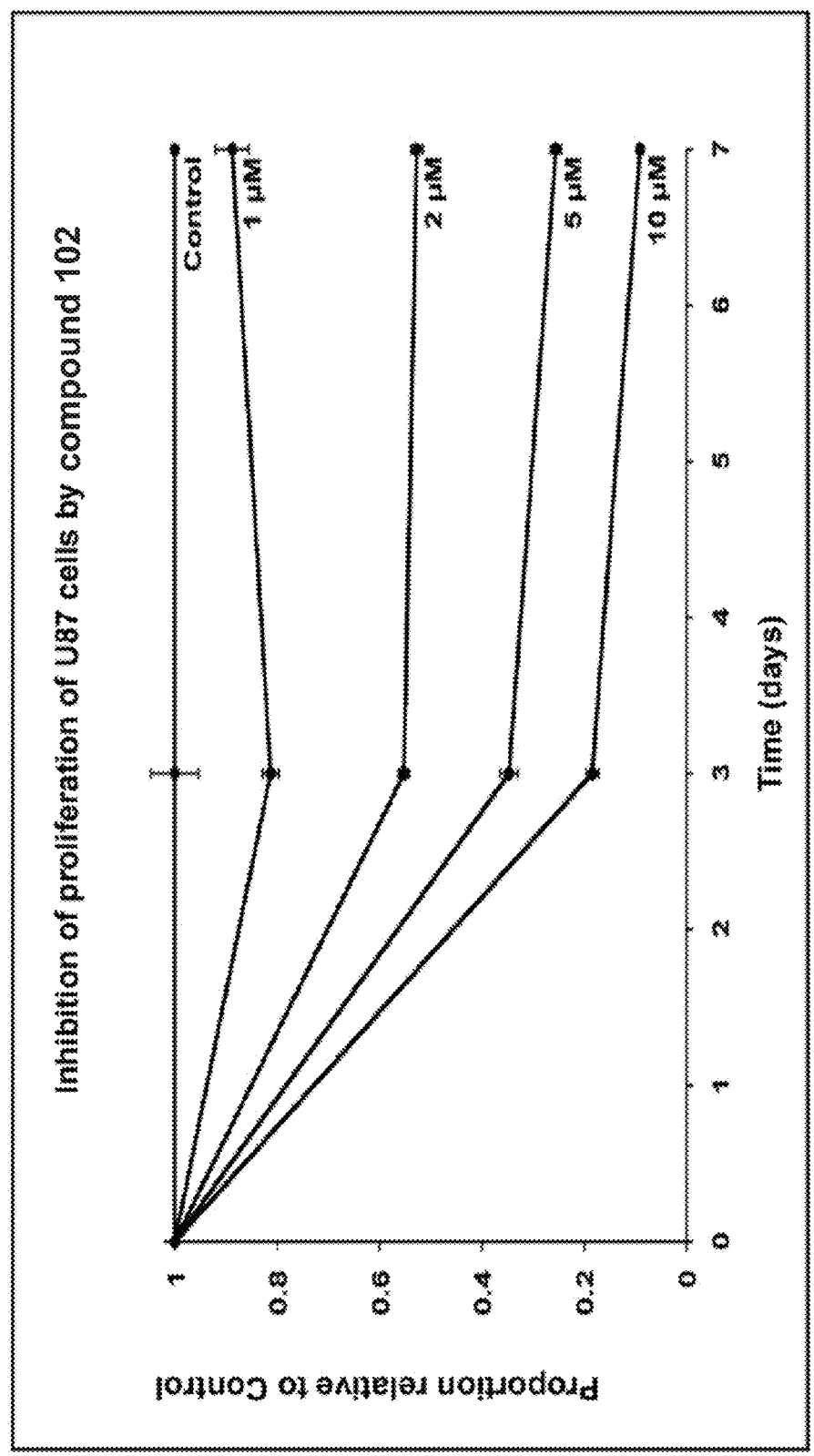

FIG. 6: Effect of Compound 102 on U87 Cells In Vitro at 1 uM; 2 uM; 5 uM; and 10 uM.

Viable cells were counted (mean and s.d.; n=3; Coulter particle counter).

Figure 7:
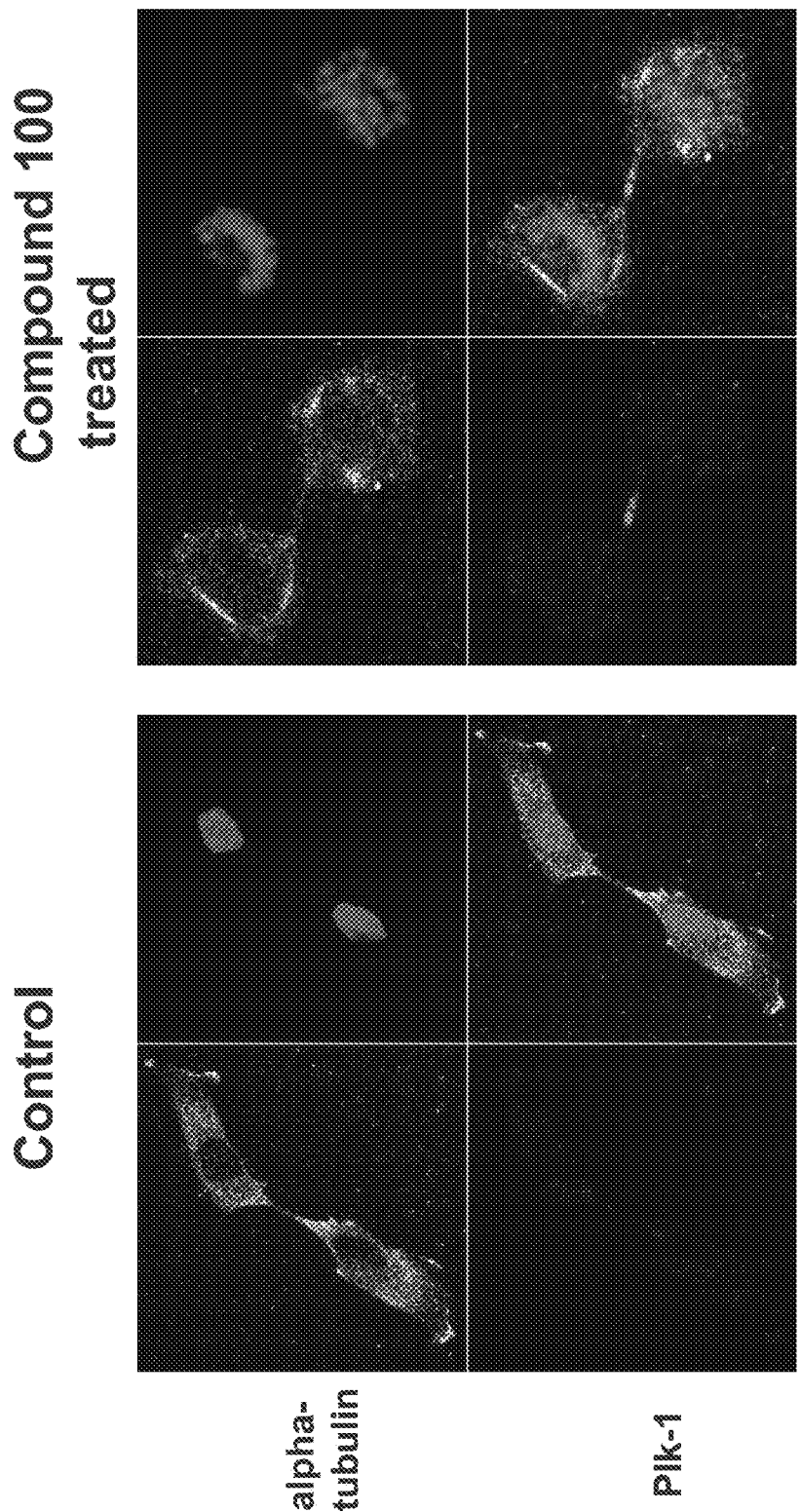

FIG. 7: Activation of Plk-1 and Disruption of Alpha Tubulin in DAOY Medulloblastoma Cells in Culture by Compound 100.

DAOY cells growing in tissue culture were exposed to 5 μM Compound 100 for 4 hours. The cells were rinsed, fixed, and stained for immunofluorescent recognition of alpha-tubulin and Plk-1. Control cells at the left show in the upper left panel diffuse staining for alpha-tubulin distributed throughout the cytoplasm. The upper right panel shows nuclear staining by the DNA binding agent DAPI. The lower left panel shows that control cells have no detectable Plk-1. The lower right panel, stained for Plk-1, alpha-tubulin, and DNA show the almost pure extra nuclear location of homogeneously distributed alpha-tubulin. The right panel consists of 4 elements showing the effects of exposure to Compound 100. In the upper left, staining for alpha-tubulin reveals marked distortion of the homogeneous distribution seen in the control cells, with multiple clumps of alpha-tubulin irregularly distributed in the cytoplasm. The upper right panel shows disordered chromatin undergoing cell division. At the lower left, staining for Plk-1 shows chromatin as two dense masses, which can be seen to be located in the remnant of the remaining bridge between dividing cells.

Figure 8:
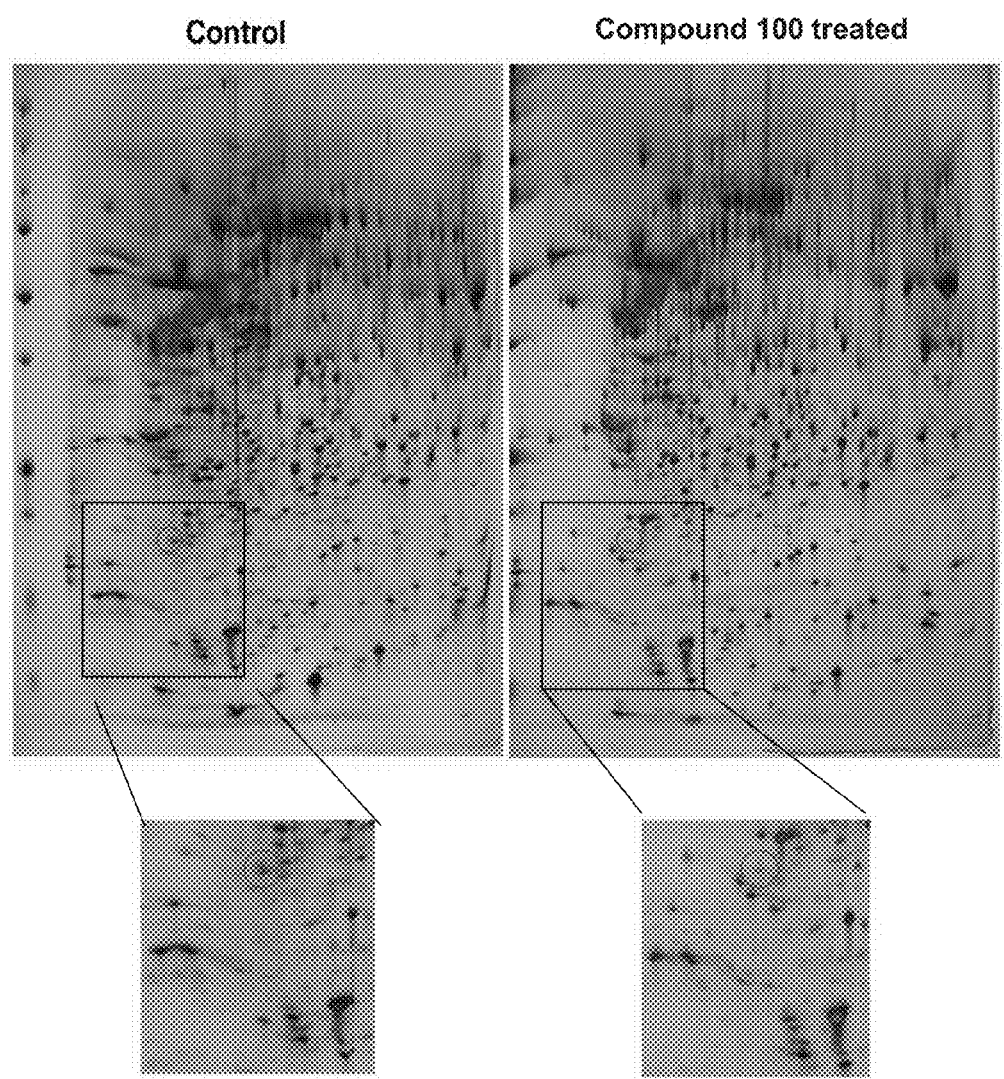

FIG. 8: Reduction in Concentration of TCTP after Treatment with Compound 100 in U87 Glioblastoma Multiformed Cells Grown as Subcutaneous Xenogeafts in SCID Mice, Detected by 2-Dimensional Gel Electrophoretic Analysis.

SCID mice were implanted with 5×10$^6$ U87 cells subcutaneously. On day 26, the mice were given 1.5 mg/kg Compound 100 by IP injection. The animals were sacrificed after 4 hours treatment and the subcutaneous mass of tumor cells were removed for 2-dimensional gel electrophoretic analysis. There was a comparable group mice exposed to vehicle. In the left panel, TCTP subsequently identified by LC-MS-MS is circled and shown in an enlargement of the gel. The lysate from Compound 100 treated cells reveals a diminution in TCTP.

Figure 9:
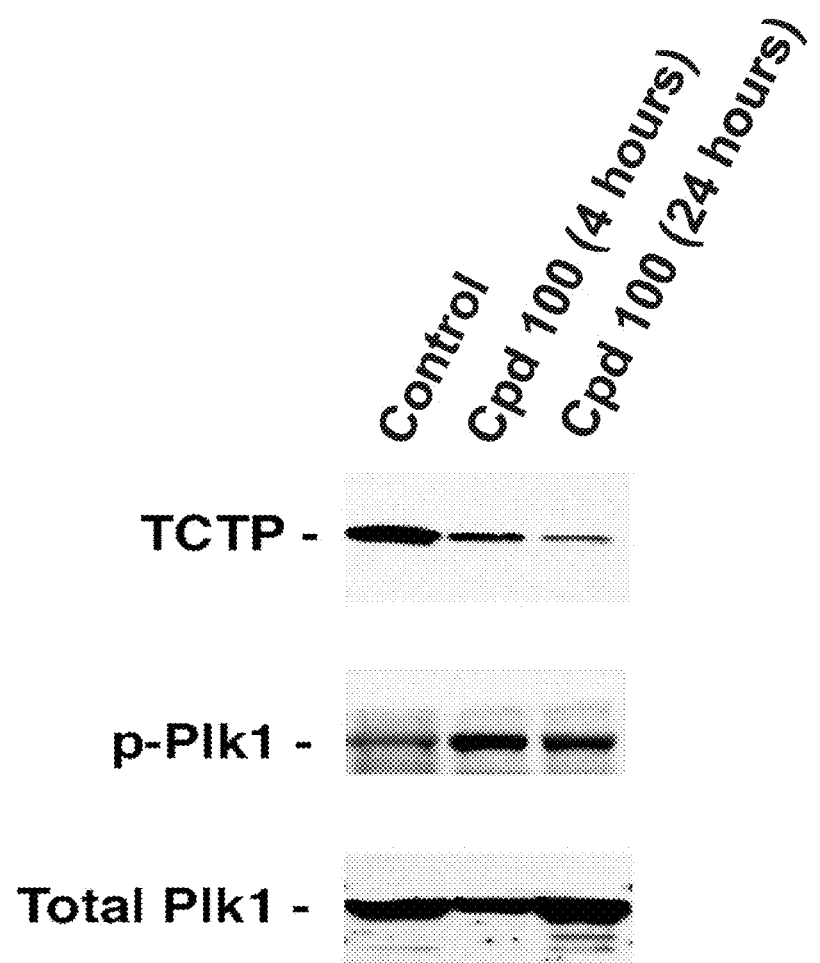

FIG. 9: Reduction in Concentration of TCTP and Activation of Plk-1 after Treatment with Compound 100 in DAOY Medullublastoma Cells in Culture Detected by Western Blot Analysis of Cell Lysates.

DAOY cells in culture were exposed to Compound 100 for 4 hours and for 24 hours, and stained for TCTP, p-Plk and total Plk on western blots. As early as 4 hours, there is a decrease in the TCTP and an increase of Plk-1 phosphorylation and at 24 hours, no TCTP is detectable at loading of comparable concentrations of total cell protein.

Figure 10A:
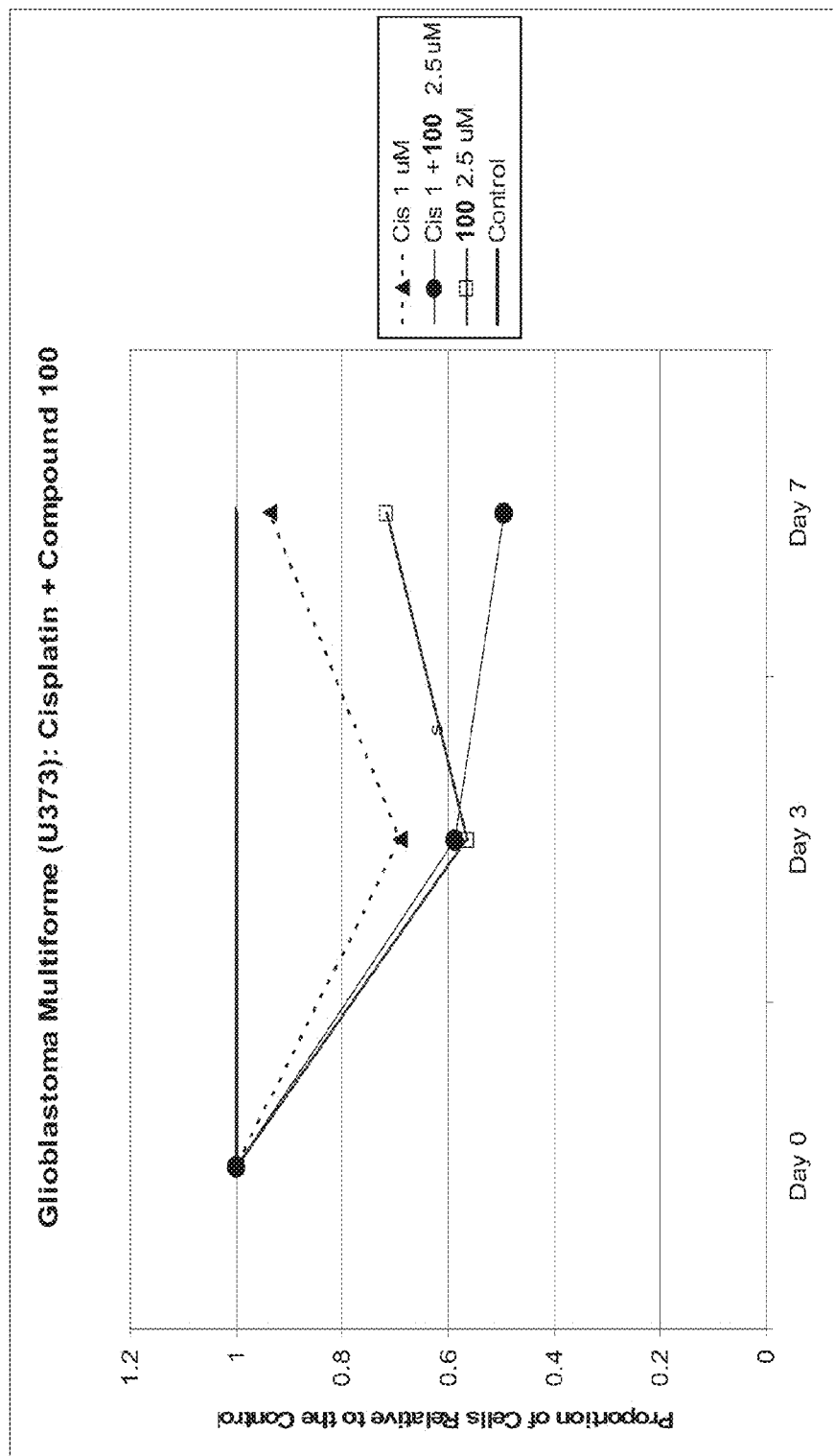
Figure 10B:
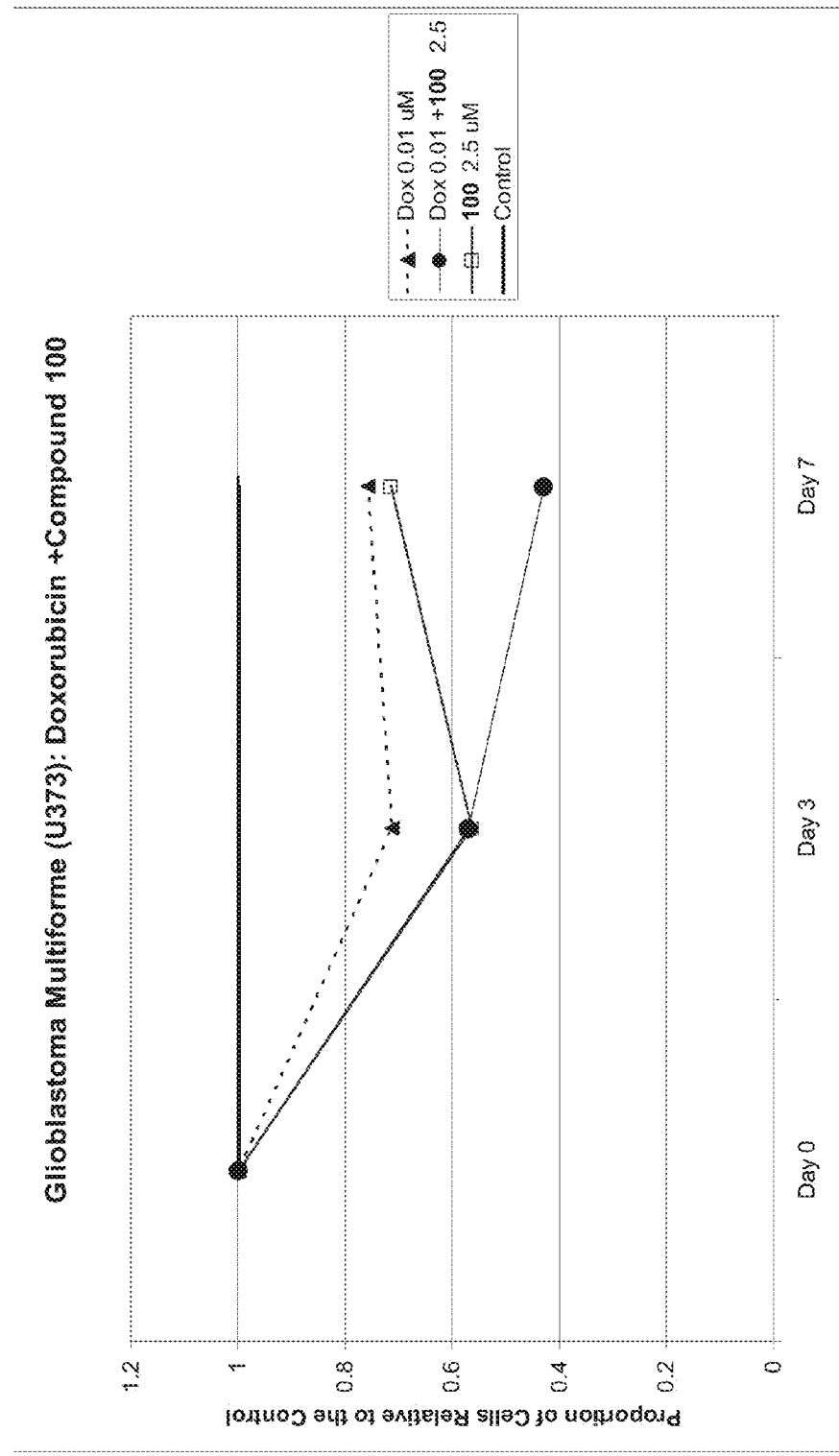
Figure 10C:
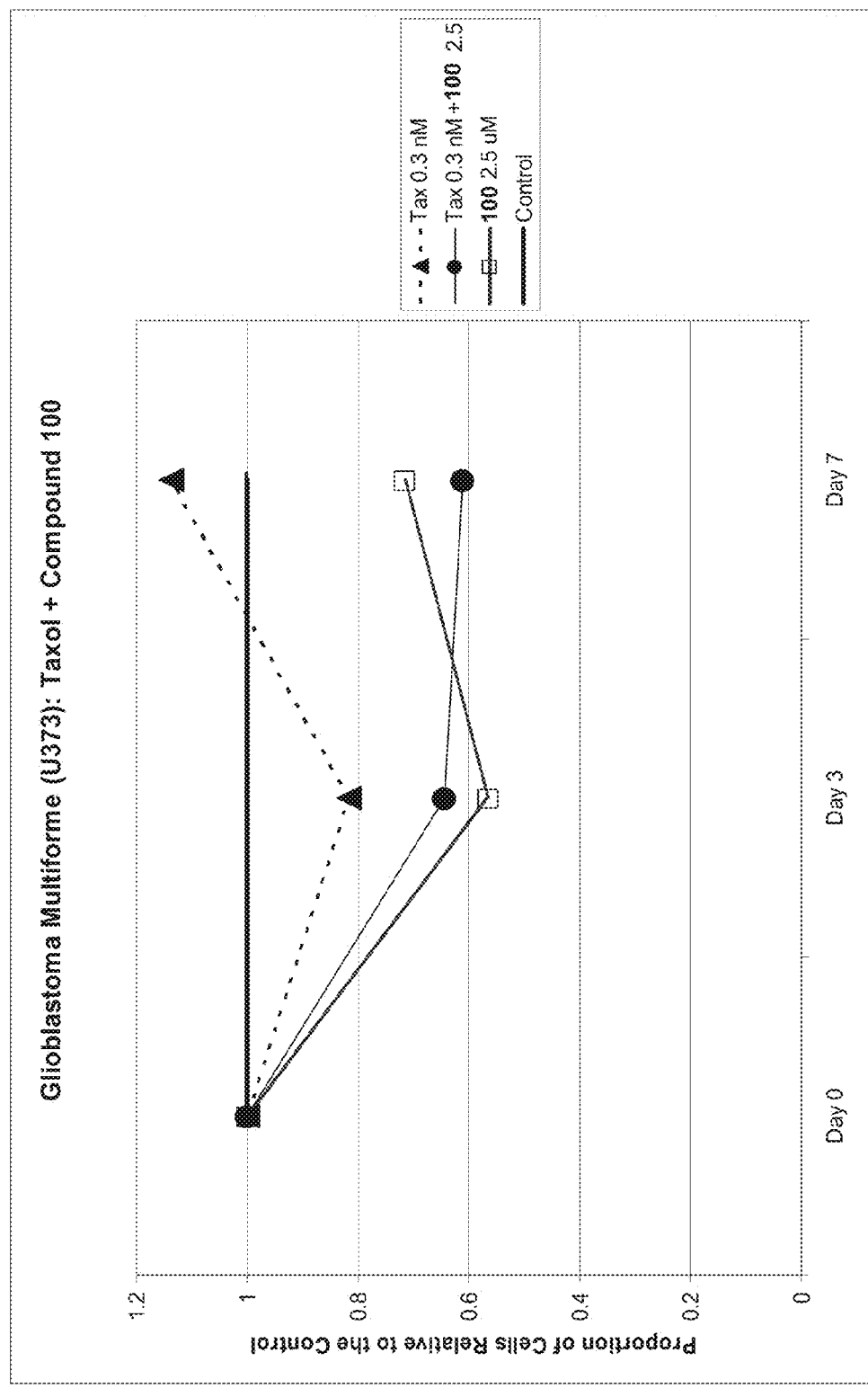

FIG. 10A-C: Compound 100 Enhances the Cytotoxic Activity of Standard Cytotoxic Chemotherapeutic Drugs as Assessed After 7 Days of Growth in Culture.

Exposure to Compound 100 enhances the inhibition of the human glioblastoma cell line, U373, by cisplatin (A), doxorubicin (B), and Taxol (C). Cells were exposed to vehicle alone (control); Compound 100 at 2.5 uM; cisplatin at 0.1 uM; doxorubicin at 0.01 uM; or taxol at 0.3 nM alone or to the combination of Compound 100 plus each of the standard agents at the same concentrations. In each case the addition of Compound 100 enhanced the effect of the cytotoxic agent at 7 days to an extent greater than that expected form the activity of each agent used alone. The expected percent inhibition at 7 days is the product of the inhibition by each agent alone. For cisplatin and Compound 100 expected inhibition at 7 days was 66% (93 5 for cisplatin alone×71% for LB-1 alone) versus the actual extent of inhibition by the combination of 50% (A). For doxorubicin and Compound 100 expected inhibition at 7 days was 53% (75.7 5 for doxorubicin alone×71% for Compound 100 alone) versus the actual extent of inhibition by the combination of 42.3% For Taxol and Compound 100 expected inhibition at 7 days 80% (114% for Taxol alone×71% for Compound 100 alone) versus the actual extent of inhibition by the combination of 61% (C).

FIG. 11A-G: Cellular and Molecular Changes in U87 Cells Induced by Compound 102 at 2.5 uM after 24 Hour Exposure (A-D, F, G) and after 3 Hours (G).

A, Nuclear changes in U87 cells in unsynchronized logarithmic growth (upper panel, green immunofluorescence [IFS] GFP labeled-actin α and lower panel, blue DAPI staining). Numerous irregular nuclei with clumped chromatin in compound 102 treated cells are indicated by arrows. B, Disordered microtubules (green IFS tubulin-α and red IFS pPlk-1-Tre 210) and irregular clumped chromatin (blue DAPI) C, Western blots of U87 lysates: pAkt-1, total Akt-1, and β-actin. D, Western blots of U87 lysates: TCTP, pPlk (Tre-210), total Plk, and β-actin. E, IFS of TCTP in U87 cells, F, Western blots p53 (ser-15), pMDM2 (ser-166), and β-actin and G, IFS of p53 (ser-15).

FIG. 12A-H: Synergistic Anti-Cancer Activity of Compound 102 Combined with TMZ.

$5 \times 10^6$ U87MG cells were inoculated s.c. into each flank of 20 SCID mice. When the xenografts were 0.5+/−0.1 cm (day 0), 5 animals each received i.p. vehicle alone days 1-12 (50% DMSO/H20); compound 102 alone at 1.5 mg/kg days 1-3, 5-7, & 9-11; TMZ alone at 80 mg/kg days 4, 8, 12; or both drugs at the same doses and schedules. If xenografts reached 1800 mm³, animals were sacrificed. A, U87 xenografts in controls grew rapidly requiring sacrifice at 3 weeks; compound 102 treated slowed growth with sacrificed between week 4-5. TMZ treated had complete regression of all xenografts by week 5 but with recurrence requiring sacrifice of all 5 animals week 7-9. compound 102 plus TMZ treated had complete regression of all xenografts by week 5 with recurrence of ½ xenografts in 3 mice at weeks 7, 11, 13 requiring sacrifice at weeks between week 11-15 and the other 2 mice had no recurrence of either xenograft for more than 7 months. Average tumor volume is shown through week 9 the last time point when xenograft volume could be determined in all 10 xenografts in the 2-drug combination group (mean and s.d., n=10 per treatment group). B, Survival curve combining the data from the study shown in FIG. 12A, with a second identical study involving a total of 10 animals with two xenografts each. Disease-free survival was defined as no recurrence of either xenografts. Kaplan-Meier analysis revealed that survival following compound 102 plus TMZ was significantly greater than with compound 102 alone and TMZ alone (logrank, p<0.001, % no xenograft recurrence, n=20). C, Tumor regression of SH-SY5Y xenografts. As in 12A, except that xenografts of SH-SY5Y cells were implanted in one flank only and animals were treated with one additional cycle of drugs, i.e., compound 102 on days 13-15, TMZ, on day 16, and compound 102 plus TMZ on the same schedules. Growth of all xenografts in control animals required sacrifice by week 3; TMZ alone delayed growth but approached the maximum allowable volume by week 7; compound 102 alone was more inhibitory with no growth until week 3 with progression thereafter, reaching about half the size of the TMZ alone treated xenografts by week 7. Compound 102 plus TMZ completely inhibited xenograft growth but with a slight residual tumor mass present at week 7. All xenografts in treatment arms ulcerated by week 7, necessitating sacrifice (mean and s.d., n=5 per treatment group). D, Histologic features (H & E staining) of U87 xenografts_24 hours after i.p. vehicle (upper left), compound 102 at 1.5 mg/kg (upper right), TMZ at 80 mg/kg (lower left), and both drugs (lower right). E, Western blots of U87 cells in culture 24 hours after exposure to compound 102 at 2.5 uM, TMZ at 25 uM or DOX at 2 uM, and compound 102 plus TMZ or DOX. F, Western blots of U373 cells 24 hours after exposure to compound 102 at 2.5 uM, doxorubicin at 2 uM, and both drugs. G, Western blots of U373 cells 24 hours after exposure to TMZ at 25 uM, okadaic acid at 2 nM, and both drugs. H, IFS of p-p53 (red) and nuclear morphology (DAPI, blue) in U373 cells after 24 hour exposure to vehicle (upper left), compound 102 at 2.5 uM (upper right), TMZ at 25 uM (lower left), and both drugs (lower panel).

Figure 13:
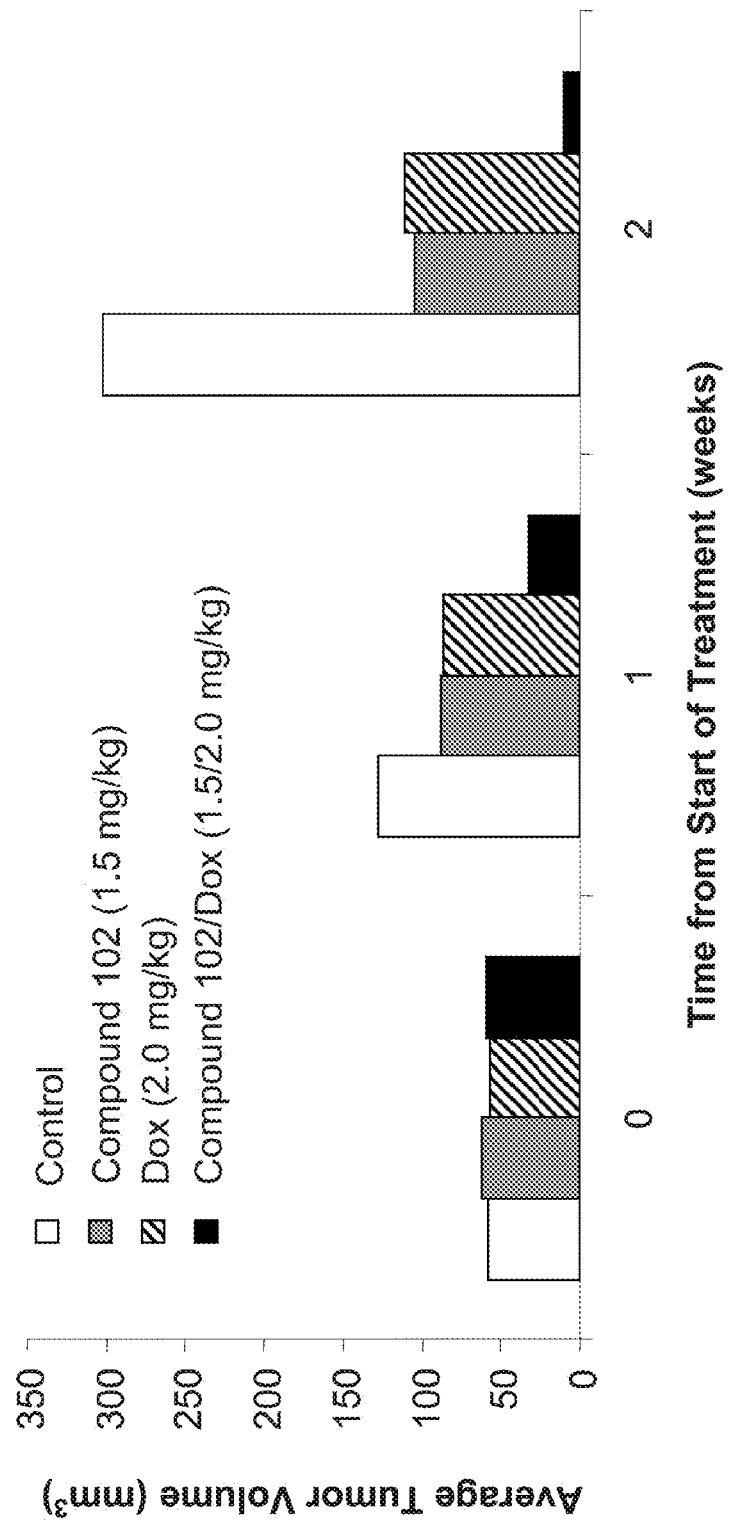

FIG. 13: Compound 102 in Combination with Doxorubicin Causes Regression of Subcutaneous Xenografts.

SCID mice implanted with 5 million U87 cells divided into four groups of 10 were treated starting at time 0 when average tumor volume was approximately 60 cubic millimeters by i.p. injection of vehicle alone (100 uL of 50% DMSO in PBS), compound 102 alone, doxorubicin alone, or compound 102 and doxorubicin at the concentrations shown in the inset. Vehicle was given on days 1, 2, 4, 5, 7, 8; compound 102 on days 1, 4, 7; doxorubicin on days 2, 5, and 8; and, each drug of the combination on the same schedule as when used alone.

Figure 14A:
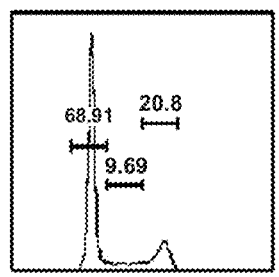
Figure 14A:
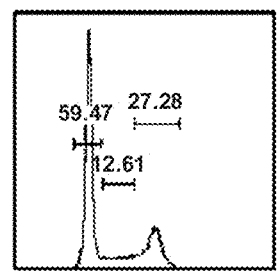
Figure 14A:
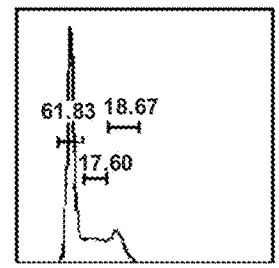
Figure 14A:
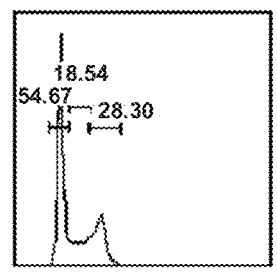
Figure 14A:
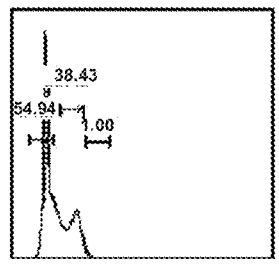
Figure 14A:
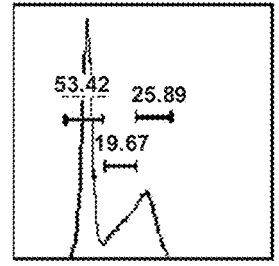
Figure 14B:
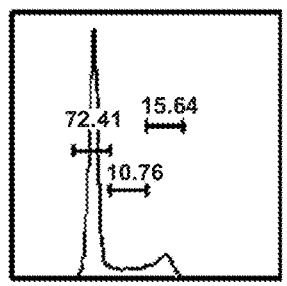
Figure 14B:
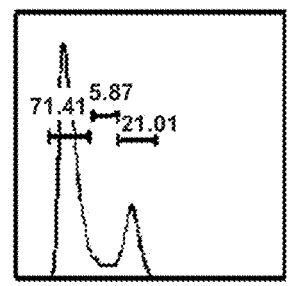
Figure 14B:
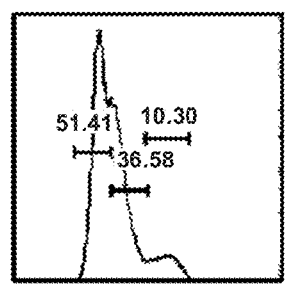
Figure 14B:
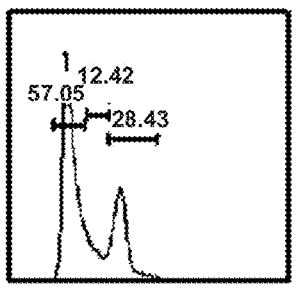
Figure 14B:
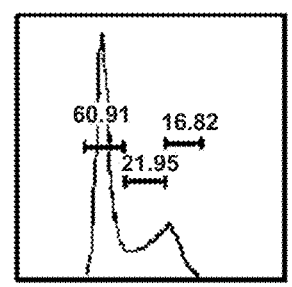
Figure 14B:
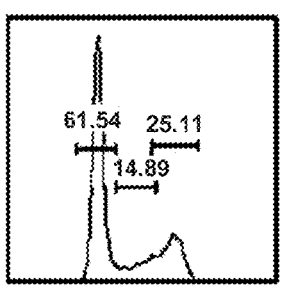
Figure 14C:
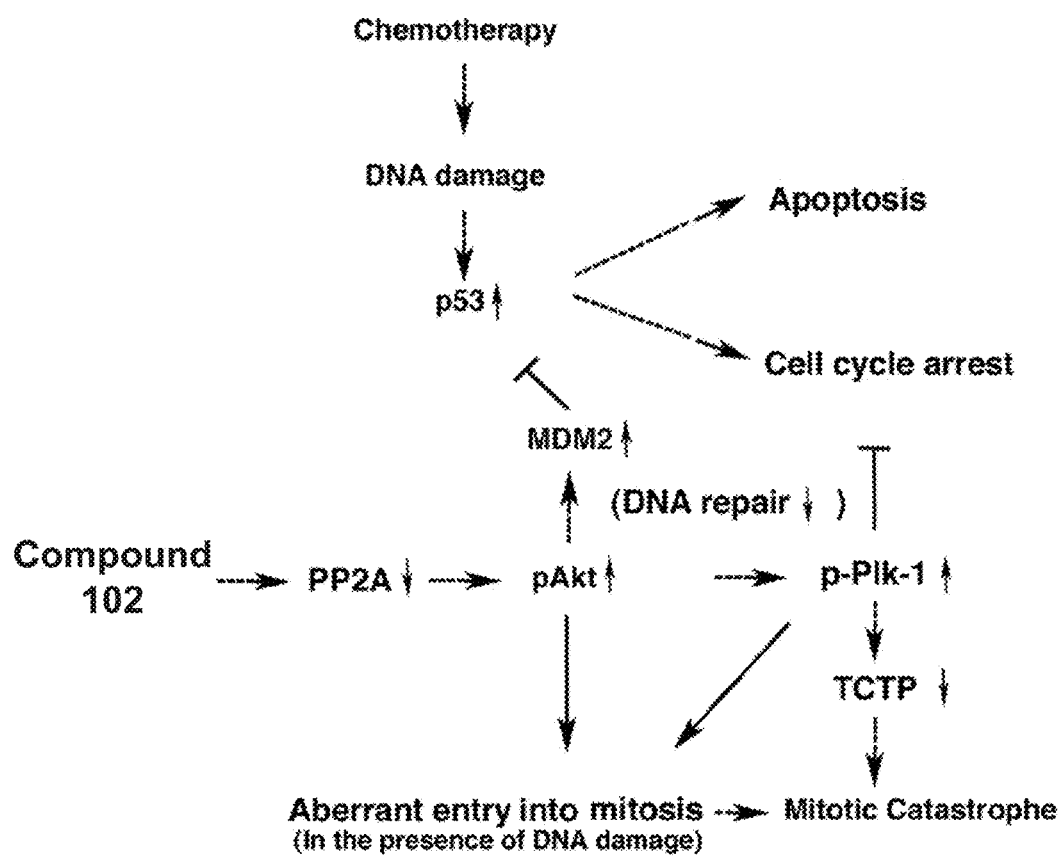

FIG. 14A-C: Cell Cycle Distribution of U87 and U373 Cells Exposed for 48 Hours to Compound 102, TMZ or DOX, and Compound 102 Plus TMZ or DOX and Schema of Mechanisms of Action.

Cells in unsynchronized logarithmic growth were exposed to vehicle or drug and adherent cells and cells in the media were collected. Harvested cells were fixed with 70% cold ethanol for 20 min at −20 degrees, washed with PBS, and stained with 10 ug/ml of PI and 1 ug/ml RNAse in TBS for 30 minutes and analyzed by FACS. A, Flow cytometry profiles of U87 cells after exposures to DMSO only, compound 102 only, 5 uM; TMZ only, 25 uM; compound 102 with TMZ combination, doxorubicin only, 2.0 uM and compound 102 with doxorubicin combination. B, Flow cytometry profiles of U373 cells. Exposures as in A, and C, Schema of proposed mechanisms of compound 102 enhancement of cancer chemotherapy.

DETAILED DESCRIPTION OF THE INVENTION

The invention provides a method of inhibiting proliferation of a cancer cell or inducing apoptosis of a cancer cell, which cancer cell does not overexpress N—CoR, comprising administering to the subject a compound, wherein the compound has the structure

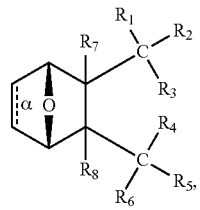

wherein
bond α is present or absent;
$R_1$ and $R_2$ is each independently H, O⁻ or $OR_9$,
where $R_9$ is H, alkyl, alkenyl, alkynyl or aryl,
or $R_1$ and $R_2$ together are =O;
$R_3$ and $R_4$ are each different, and each is OH, O⁻, $OR_4$, SH, S⁻, $SR_9$,

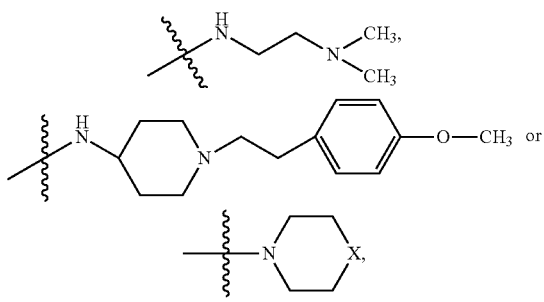

where X is O, S, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

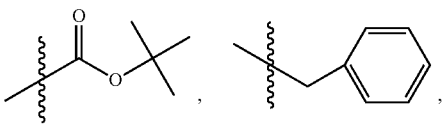

—$CH_2CN$, —$CH_2CO_2R_{11}$, —$CH_2COR_{11}$, —$NHR_{11}$ or —$NH^+(R_{11})_2$,
where each $R_{11}$ is independently alkyl, alkenyl or alkynyl, each of which is substituted or unsubstituted, or H;
$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{12}$,
where $R_{12}$ is H, aryl or a substituted or unsubstituted alkyl, alkenyl or alkynyl,
or a salt, enantiomer or zwitterion of the compound, in an amount effective to inhibit the proliferation or to induce apoptosis of the cancer cell.

In an embodiment of the above method, when X is $N^+R_{10}R_{10}$ and one $R_{10}$ is $CH_3$, then the other $R_{10}$ is alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

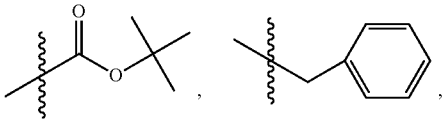

—$CH_2CN$, —$CH_2CO_2R_{11}$, —$CH_2COR_{11}$, —$NHR_{11}$ or —$NH^+(R_{11})_2$,
where each $R_{11}$ is independently alkyl, alkenyl or alkynyl, each of which is substituted or unsubstituted, or H.

This invention provides a method of inhibiting proliferation or inducing apoptosis of a cancer cell which overexpresses TCTP comprising administering to the subject a compound, wherein the compound had the structure

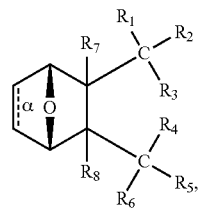

wherein
bond α is present or absent;
$R_1$ and $R_2$ is each independently H, O⁻ or $OR_9$,
where $R_9$ is H, alkyl, alkenyl, alkynyl or aryl,
or $R_1$ and $R_2$ together are =O;
$R_3$ and $R_4$ are each different, and each is OH, O⁻, $OR_9$, SH, S⁻, $SR_9$,

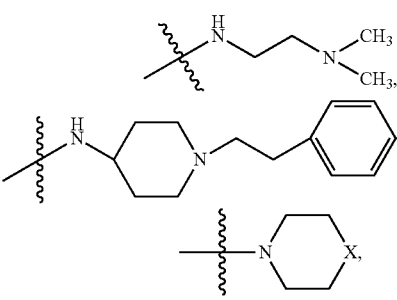

where X is O, S, $NR_{10}$, or $N^+R_{10}R_{10}$,
where each $R_{13}$ is independently H, $C_2$-$C_{12}$ alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

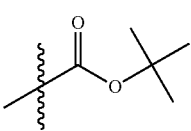 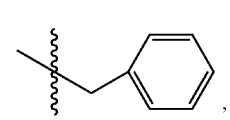

—CH$_2$CN, —CH$_2$CO$_2$R$_{11}$, —CH$_2$COR$_{11}$, —NHR$_{11}$ or —NH$^+$(R$_{11}$)$_2$,
  where each R$_{11}$ is independently alkyl, alkenyl or alkynyl, each of which is substituted or unsubstituted, or H;
R$_5$ and R$_6$ is each independently H, OH, or R$_5$ and R$_6$ taken together are =O; and
R$_7$ and R$_8$ is each independently H, F, Cl, Br, SO$_2$Ph, CO$_2$CH$_3$, or SR$_{12}$,
  where R$_{12}$ is H, aryl or a substituted or unsubstituted alkyl, alkenyl or alkynyl,
or a salt, enantiomer or zwitterion of the compound, in an amount effective to inhibit the proliferation or to induce apoptosis of the cancer cell.

In an embodiment of the above method, the cancer cell does not overexpress N—CoR.

In another embodiment of any of the above methods, the compound has the structure

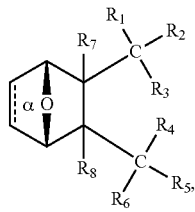

wherein
bond α is present or absent;
R$_1$ and R$_2$ is each independently H, O$^-$ or OR$_9$,
  where R$_9$ is H, alkyl, alkenyl, alkynyl or aryl,
or R$_1$ and R$_2$ together are =O;
R$_3$ and R$_4$ are each different, and each is OH, O$^-$, OR$_9$, SH, S$^-$, SR$_9$,

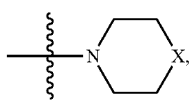

where X is O, S, NR$_{10}$, or N$^+$R$_{10}$R$_{10}$,
  where each R$_{10}$ is independently C$_2$-C$_{12}$ alkyl, substituted C$_2$-C$_{12}$ alkyl, alkenyl, substituted C$_4$-C$_{12}$ alkenyl, alkynyl, substituted alkynyl, aryl, substituted aryl where the substituent is other than chloro when R$_1$ and R$_2$ are =O,
    —CH$_2$CN, —CH$_2$CO$_2$R$_{11}$, —CH$_2$COR$_{11}$, —NHR$_{11}$ or —NH$^+$(R$_{11}$)$_2$,
    where each R$_{11}$ is independently alkyl, alkenyl or alkynyl, each of which is substituted or unsubstituted, or H;
R$_5$ and R$_6$ is each independently H, OH, or R$_5$ and R$_6$ taken together are =O; and
R$_7$ and R$_8$ is each independently H, F, Cl, Br, SO$_2$Ph, CO$_2$CH$_3$, or SR$_{12}$,
  where R$_{12}$ is H, aryl or a substituted or unsubstituted alkyl, alkenyl or alkynyl,
or a salt, enantiomer or zwitterion of the compound.

In an embodiment of any of the above methods the cancer is adrenocortical cancer, bladder cancer, osteosarcoma, cervical cancer, esophageal, gallbladder, head and neck cancer, Hodgkin lymphoma, non-Hodgkin lymphoma, renal cancer, melanoma, pancreatic cancer, rectal cancer, thyroid cancer and throat cancer.

This invention provides a method of inhibiting proliferation or inducing apoptosis of a cancer cell that overexpresses TCTP by administering to the subject a compound, wherein the compound has the structure

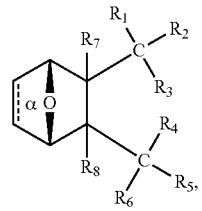

wherein
bond α is present or absent;
R$_1$ and R$_2$ is each independently H, O$^-$ or OR$_9$,
  where R$_9$ is H, alkyl, alkenyl, alkynyl or aryl,
or R$_1$ and R$_2$ together are =O;
R$_3$ and R$_4$ are each different, and each is OH, O$^-$, OR$_9$, SH, S$^-$, SR$_9$,

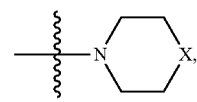

where X is O, S, NR$_{10}$, or N$^+$R$_{10}$R$_{10}$,
  where each R$_{10}$ is independently C$_2$-C$_{12}$ alkyl, substituted C$_2$-C$_{12}$ alkyl, alkenyl, substituted C$_4$-C$_{12}$ alkenyl, alkynyl, substituted alkynyl, aryl, substituted aryl where the substituent is other than chloro when R$_1$ and R$_2$ are =O,
    —CH$_2$CN, —CH$_2$CO$_2$R$_{11}$, —CH$_2$COR$_{11}$, —NHR$_{11}$ or —NH$^+$(R$_{11}$)$_2$,
    where each R$_{11}$ is independently alkyl, alkenyl or alkynyl, each of which is substituted or unsubstituted, or H;
R$_5$ and R$_6$ is each independently H, OH, or R$_5$ and R$_6$ taken together are =O; and
R$_7$ and R$_8$ is each independently H, F, Cl, Br, SO$_2$Ph, CO$_2$CH$_3$, or SR$_{12}$,
  where R$_{12}$ is H, aryl or a substituted or unsubstituted alkyl, alkenyl or alkynyl,
or a salt, enantiomer or zwitterions of the compound, in an amount effective to inhibit the proliferation or to induce apoptosis of the cancer cell.

In an embodiment of any of the above methods, the cancer cell is in a subject. In a further embodiment, the subject is mammal.

In an embodiment of any of the above methods, the cancer cell is a neural cell. In another embodiment, the cancer cell is a lymphoid cell.

Another embodiment of the above methods further comprises administering an anti-cancer agent in an amount effective to inhibit the proliferation or to induce apoptosis of the cancer cell. In a further embodiment, the anticancer agent is chemotherapeutic agent, a DNA intercalating agent, a spindle poison or a DNA damaging agent.

Another embodiment of the above methods further comprises administering a retinoid receptor ligand in an amount such that any of the compounds described above and the retinoid receptor ligand is effective to inhibit the proliferation or to induce apoptosis of the cancer cell.

In the method of the invention, the retinoid receptor ligand may be a retinoid, such as a retinoic acid, e.g. cis retinoic acid or trans retinoic acid. The cis retinoic acid may be 13-cis retinoic acid and the trans retinoic acid may be all-trans retinoic acid. In the preferred embodiment, the retinoic acid is all-trans retinoic acid (ATRA).

Retinoid receptor ligands used in the method of the invention include vitamin A (retinol) and all its natural and synthetic derivatives (retinoids).

Another embodiment of the above method further comprises administering a histone deacetylase ligand in an amount such that the any of the compounds described above and the histone deacetylase ligand is effective to inhibit the proliferation or to induce apoptosis of the cancer cell.

In the method of the invention, the histone deacetylase ligand may be an inhibitor, e.g. the histone deacetylase inhibitor HDAC-3 (histone deacetylase-3). The histone deacetylase ligand may also be selected from the group consisting of 2-amino-8-oxo-9,10-epoxy-decanoyl, 3-(4-aroyl-1H-pyrrol-2-yl)-N-hydroxy-2-propenamide, APHA Compound 8, apicidin, arginine butyrate, butyric acid, depsipeptide, depudecin, HDAC-3, m-carboxycinnamic acid bis-hydroxamide, N-(2-aminophenyl)-4-[N-(pyridin-3-yl-methoxycarbonyl)aminomethyl]benzamide, MS 275, oxamflatin, phenylbutyrate, pyroxamide, scriptaid, sirtinol, sodium butyrate, suberic bishydroxamic acid, suberoylanilide hydroxamic acid, trichostatin A, trapoxin A, trapoxin B and valproic acid. In another embodiment of the invention, the inhibitor is valproic acid.

In one embodiment, the methods described above further comprise administering both a retinoid receptor ligand and a histone deacetylase ligand each in an amount such that the amount of each of the compounds described above, the histone deacetylase ligand and the retinoid receptor ligand is effective to inhibit the proliferation or to induce apoptosis of the cancer cell.

In one embodiment of the methods disclosed herein R3 or R4 is

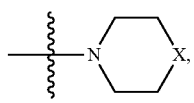

where X is O, S, $NR_{10}$, or $N^+R_{10}R_{10}$.

This invention provides a method for determining whether a compound is effective in inducing cell death comprising (a) contacting a first cancer cell with the compound; (b) determining the level of expression of TCTP in the first cancer cell; (c) contacting a second cancer cell with a protein phosphatase 2A inhibitor; (d) determining the level of expression of TCTP in the second cancer cell; (e) comparing the level of expression of TCTP determined in step (b) with the level determined in step (d), wherein, when the level of expression determined in step (b) is equal to, or lower than, the level of expression determined in step (d) indicates that the compound is effective to induce cell death.

In one embodiment of the above method, the protein phosphatase 2A inhibitor is a compound having the structure:

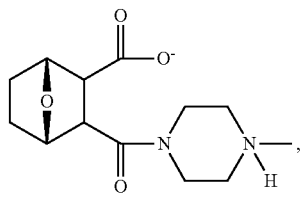
(compound 100)

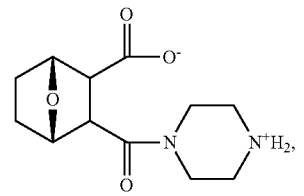
(compound 101)

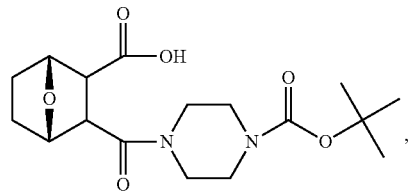
(compound 102)

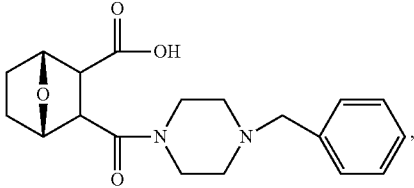
(compound 103)

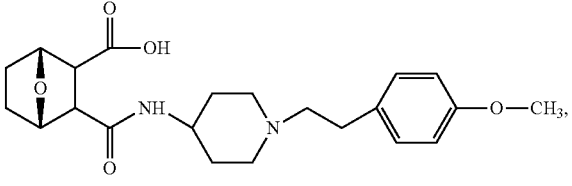
(compound 104)

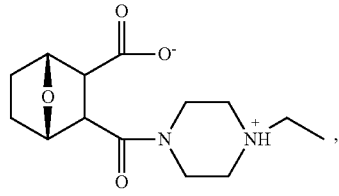
(compound 105)

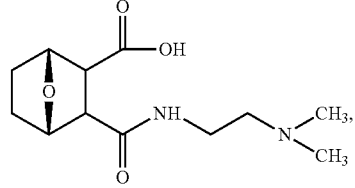
(compound 106)

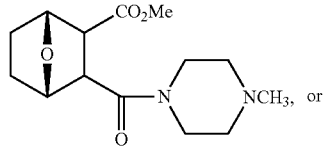
(compound 107)

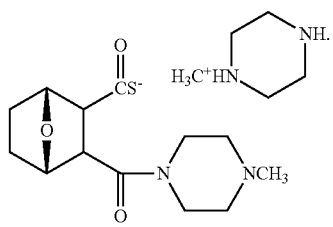
(compound 108)

This invention provides a method for determining whether a compound is effective in inducing cell death in a cancer cell comprising (a) contacting a cancer cell with the compound; (b) determining the level of expression of TCTP in the cancer cell; (c) determining the level of expression of TCTP in a non-cancerous cell; (e) comparing the level of expression of TCTP determined in step (b) with the level determined in step (d), wherein, when the level of expression determined in step (b) is lower than, the level of expression determined in step (d) indicates that the compound is effective to induce cell death in the cancer cell.

This invention provides a method for determining whether treatment of a subject with an agent will be successful in treating a subject suffering from cancer comprising (a) obtaining a first sample from the subject prior to treatment; (b) determining the level of expression of TCTP in the sample; (c) administering to the subject the agent; (d) obtaining a second sample from the subject after treatment with the agent; (e) determining the level of expression of TCTP in the second sample obtained; wherein, when the level of expression determined in step (b) is lower than the level of expression determined in step (e) indicates that the treatment of the subject with the agent be successful.

This invention provides a method for predicting whether treatment of a subject with an agent will be successful in treating a subject suffering from cancer comprising (a) obtaining a sample comprising cancer cells from the subject; (b) culturing the cancer cells; (c) determining the level of expression of TCTP in the cancer cells; (d) contacting the cancer cells with the agent; (e) determining the level of expression of TCTP in the cancer cells; (f) comparing the level of expression of TCTP determined in step (c) with the level of expression determined in step (e); wherein, when the level of expression determined in step (c) is lower than the level of expression determined in step (e) predicts that treatment of the subject with the agent will be successful in treatment of the cancer.

This invention provides a method for reducing the amount of TCTP in a cell comprising contacting the cell with an effective amount of protein phosphatase inhibitor, thereby reducing the amount of TCTP in the cell.

In one embodiment of the above method, the protein phosphatase inhibitor is a protein phosphatase 2A inhibitor. In another embodiment, the protein phosphatase 2A inhibitor is a compound having the structure

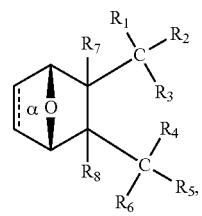

wherein
bond α is present or absent;
$R_1$ and $R_2$ is each independently H, $O^-$ or $OR_9$,
where $R_9$ is H, alkyl, alkenyl, alkynyl or aryl,
or $R_1$ and $R_2$ together are =O;
$R_3$ and $R_4$ are each different, and each is OH, $O^-$, $OR_9$, SH, $S^-$, $SR_9$,

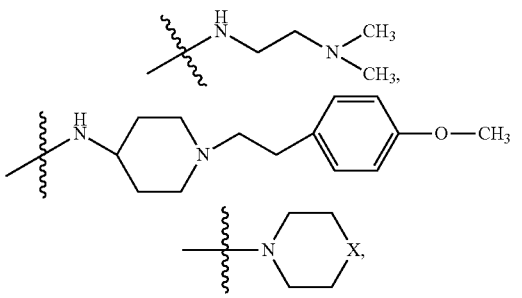

where X is O, S, $NR_{10}$, or $N^+R_{10}R_{10}$,
where each $R_{10}$ is independently H, alkyl, substituted $C_2$-$C_{12}$ alkyl, alkenyl, substituted $C_4$-$C_{12}$ alkenyl, alkynyl, substituted alkynyl, aryl, substituted aryl where the substituent is other than chloro when $R_1$ and $R_2$ are =O,

—$CH_2CN$, —$CH_2CO_2R_{11}$, —$CH_2COR_{11}$, —$NHR_{11}$ or —$NH^+(R_{11})_2$,
where each $R_{11}$ is independently alkyl, alkenyl or alkynyl, each of which is substituted or unsubstituted, or H;
$R_5$ and $R_6$ is each independently H, OH, or $R_5$ and $R_6$ taken together are =O; and
$R_7$ and $R_8$ is each independently H, F, Cl, Br, $SO_2Ph$, $CO_2CH_3$, or $SR_{12}$,
where $R_{12}$ is H, aryl or a substituted or unsubstituted alkyl, alkenyl or alkynyl,
or a salt, enantiomer or zwitterion of the compound.

In another embodiment of the above method, the cell is a cancer cell that does not overexpress N—CoR. In another embodiment, the cancer cell overexpresses TCTP.

DEFINITIONS

Certain embodiments of the disclosed compounds can contain a basic functional group, such as amino or alkylamino, and are thus capable of forming pharmaceutically acceptable salts with pharmaceutically acceptable acids, or contain an acidic functional group and are thus capable of forming pharmaceutically acceptable salts with bases. The instant compounds therefore may be in a salt form. As used herein, a "salt" is a salt of the instant compounds which has been modified by making acid or base salts of the compounds. The salt may be pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. For a description of possible salts, see, e.g., Berge et al. (1977) "Pharmaceutical Salts", *J. Pharm. Sci.* 66:1-19.

As used herein, "therapeutically effective amount" means an amount sufficient to treat a subject afflicted with a disease (e.g. cancer) or to alleviate a symptom or a complication associated with the disease.

As used herein, "treating" means slowing, stopping or reversing the progression of a disease, particularly cancer.

As used herein, "overexpressing TCTP" means that the level of TCTP expressed in cells of the tissued tested are elevated in comparison to the levels of TCTP as measure in normal healthy cells of the same type of tissued under analgous conditions.

As used herein, "cancer cell" is a cell that is characterized by uncontrolled growth and cell division and can include tumor cells. Cancer cells, which can include tumor cells, may or may not overexpress N—CoR.

As used herein, "mitotic catastrophe" refers to a condition of the cell characterized by abnormalities in the process of mitosis that lead to cell death by any of the known cell death pathways including apoptosis, necrosis, senescence, and autophagy.

As used herein, "apoptosis" refers to programmed cell death or any of a series morphological processes leading to controlled cellular self-destruction.

As used herein, "proliferation" refers to a sustained increase in the number of cells.

As used herein, "cell cycle progression" refers to the advancement of a cell through a series of events that take place in the cell leading to its division and replication.

As used herein, "cell cycle arrest" refers to the halting of a series of events that take place in the cell leading to its division and replication, which may be caused by a number of factors, including, but not limited to, DNA damage, X-radiation, ionizing radiation, and chemotherapeutic agents.

As used herein, anti-cancer agent means standard cancer regimens which are currently known in the art. Examples include, but are not limited to, x-radiation, ionizing radiation, DNA damaging agents, DNA intercalating agents, microtubule stabilizing agents, microtubule destabilizing agents, spindle toxins, and chemotherapeutic agents. Further examples include cancer regimens approved by the Food and Drug Administration, which include, but are not limited to, abarelix, aldesleukin, alemtuzumab, alitertinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, celecoxib, cetuximab, chlorambucil, cisplatin, cladribine, clofarabine, clyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, VP-16, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovrin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargrmostim, sorafenib, streptozocin, sunitinib, sunitinib maleate, talc, tamoxifen, temozolomide, teniposide, VM-26, testolactone, thalidomide, thioguanine, G-TG, thiotepa, topotecan, toremifene, tositumomab, trastuzumab, tretinoin ATRA, ruacil mustard, valrunicin, vinblastine, vincristine, vinorelbine, vorinostat, zoledronate, and zoledronic acid.

A complete list of all FDA approved cancer drugs can be found at accessdata.fda.gov/scripts/cder/onctools/druglist.cfm Examples of DNA intercalating agents include, but are not limited to, doxorubicin, daunorubicin, dactinomycin. Examples of Spindle Poisons include, but are note limited to vincristine, vinblastine, taxol. DNA damaging agents include antracyclines, bleomycin, cisplatin, etoposide, temozolomide, and nitrosoureas.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, ..., n–1 or n carbons in a linear or branched arrangement, and specifically includes methyl, ethyl, propyl, butyl, pentyl, hexyl, and so on. An embodiment can be $C_1$-$C_{12}$ alkyl. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2, ..., n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated. An embodiment can be $C_2$-$C_{12}$ alkenyl.

The term "alkynyl" refers to a hydrocarbon radical straight or branched, containing at least 1 carbon to carbon triple bond, and up to the maximum possible number of non-aromatic carbon-carbon triple bonds may be present.

Thus, $C_2$-$C_n$ alkynyl is defined to include groups having 1, 2, ..., n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl.

As used herein, "aryl" is intended to mean any stable monocyclic or bicyclic carbon ring of up to 10 atoms in each ring, wherein at least one ring is aromatic. Examples of such aryl elements include phenyl, naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring. The substituted aryls included in this invention include substitution at any suitable position with amines, substituted amines, alkylamines, hydroxys and alkylhydroxys, wherein the "alkyl" portion of the alkylamines and alkylhydroxys is a $C_2$-$C_n$ alkyl as defined hereinabove. The substituted amines may be substituted with alkyl, alkenyl, alkynl, or aryl groups as hereinabove defined.

The alkyl, alkenyl, alkynyl, and aryl substituents may be unsubstituted or unsubstituted, unless specifically defined otherwise. For example, a ($C_1$-$C_6$) alkyl may be substituted with one or more substituents selected from OH, oxo, halogen, alkoxy, dialkylamino, or heterocyclyl, such as morpholinyl, piperidinyl, and so on.

In the compounds of the present invention, alkyl, alkenyl, and alkynyl groups can be further substituted by replacing one or more hydrogen atoms by non-hydrogen groups described herein to the extent possible. These include, but are not limited to, halo, hydroxy, mercapto, amino, carboxy, cyano and carbamoyl.

The term "substituted" as used herein means that a given structure has a substituent which can be an alkyl, alkenyl, or aryl group as defined above. The term shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

As used herein, "zwitterion" means a compound that is electrically neutral but carries formal positive and negative charges on different atoms. Zwitterions are polar, have high solubility in water and have poor solubility in most organic solvents.

The compounds disclosed herein may also form zwitterions. For example, a compound having the structure

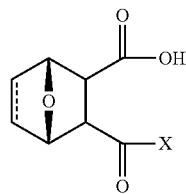

may also for the following zwitterionic structure

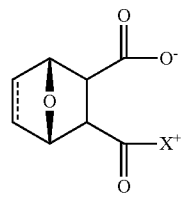

where X is as defined throughout the disclosures herein.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventicularly, intratumorally, into cerebral parenchyma or intraparenchchymally.

The following delivery systems, which employ a number of routinely used pharmaceutical carriers, may be used but are only representative of the many possible systems envisioned for administering compositions in accordance with the invention.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

It is understood that substituents and substitution patterns on the compounds of the instant invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

Compounds 100-108, as described herein, were obtained from Lixte Biotechnology, Inc. 248 Route 25A, No. 2, East Setauket, New York.

The present invention relates generally to compositions and methods of inhibiting tumor genesis, tumor growth, and tumor survival. The compositions comprise small molecule compounds that reduce the amount of translational controlled tumor protein (TCTP) in the cancer cell leading to its death.

Inhibitors of protein phosphatase 2A have been developed that induce cancer cell death by induction of mitotic catastrophe by a mechanism different from those mechanisms that underlie the anti-cancer activity of these common chemotherapeutic agents. Therefore, the compound 100 series of drugs have toxicities different from most if not all commonly used chemotherapeutic agents and thus, are combined with many active anti-cancer therapeutic regimens to enhance therapeutic benefit.

SUMMARY

Compound 100 Preferentially Inhibits Cancer Cells Compared to Normal Cells and May be Combined with Standard Anti-Cancer Chemotherapy and/or Radiotherapy Regimens to Improved Therapeutic Effect Compound 100 and homologs inhibit many human cancer cell types growing in cell culture and growing in vivo as xenografts (PCT application on bicycloheptanes etc). Exposure of cancer cells to Compound 100 is associated with a rapid and marked decrease in translationally controlled tumor protein, TCTP, one of the most highly conserved and most abundant proteins in eukaryotic cells (Bommer and Thiele, 2004). TCTP is essential to cancer cell growth but is not critical to the survival of normal (untransformed) cells (Chen et al, 2007B). Targeting TCTP with Compound 100 (and its homologs) is an effective means for disrupting cancer cell division and therefore for treating cancers in general.

Reduction in TCTP by Compound 100 leads to disordered cell replication and division. The addition of Compound 100 to standard cancer regimens enhances the effectiveness of other cancer treatments that inhibit cell growth and/or division. Compound 100 exerts its anti-cancer activity by a mechanism of action that is not toxic to normal cells, at least in non-embryonic cells. Since reduction of TCTP is not toxic to normal adult cells such as the bone marrow, GI tract, peripheral nerves, or auditory nerves, normal tissue often damaged by most cancer chemotherapeutic agents, compound 100 can be combined with standard anti-cancer regimens to enhance anti-cancer activity while avoiding increased toxicity.

In the instance of compound 100 (and its homologs), the likelihood of a particular cell type being vulnerable to treatment with a drug and the extent of potency of a drug can be simply and rapidly estimated by the extent to which exposure to Compound 100 reduces TCTP. Assays that measure the ability of compounds to decrease the abundance of TCTP in cancer cell lines are useful for the identification of compounds that may be effective anti-cancer drugs.

Assay of TCTP is a Tool for Screening Compounds for Activity Likely to be Useful in Cancer Treatment and for Determining Cell Types Likely to be Inhibited by Compound 100.

Assays that measure the ability of compounds to decrease the abundance of TCTP in cancer cell lines are useful for the identification of compounds that may be effective anti-cancer drugs. In the instance of compound 100 (and its homologs), the likelihood of a particular cell type being vulnerable to treatment with a drug and the extent of potency of a drug can be simply and rapidly estimated by the extent to which exposure to compound 100 reduces TCTP.

INTRODUCTION

We have discovered that inhibition of the serine/threonine protein phosphatase inhibitor PP2A leads to a reduction in the amount of TCTP in multiple human cancer cell lines including lines derived from glioblastoma multiforme, medulloblastoma, neuroblastoma, central nervous system lymphoma, and breast cancer. We synthesized a series of small molecule inhibitors of PP2A with varying degrees of lipophilicity and showed that both the water soluble lead compound compound 100 and the lipid soluble lead compound, compound 102, lead to increased phosphorylation and a decrease in the amount of TCTP in cell lines in vitro and growing as xenografts of human glioblastomas and neuroblastomas.

Because these molecular changes, i.e. increased phosphorylation and reduction of TCTP, are likely not to affect the integrity of normal adult cells, we believe the inhibition of TCTP via small molecule inhibitors of the pathway regulating the integrity of the interaction of TCTP with the anti-apoptic machinery is an effective means of treating cancer. In addition, this pathway is also exploitable for the inhibition of other cancer cell types undergoing excessive replication and white blood cell proliferation in the inflammatory response.

Disclosed herein is a method for the treatment of human and animal cancers based on inducing alterations of multiple components of processes responsible for cell growth and replication with a single pharmacologic intervention. In the adult, most normal cells are not prepared for cell replication and cannot be forced into cell replication by a pharmacologic intervention. Many types of cancers, however, are characterized by a state of activation of multiple enzymes that initiate and carry out cell replication. This abnormal state of heightened activation can be further intensified by inhibition of serine/threonine protein phosphatase 2A (PP2A), causing increased activation of the mitotic process to a level at which chaotic cell division results in cell death. The critical and final step in activation of this pathway by inhibition of PP2A is a reduction in TCTP and concomitant reduction in mcl-1. In the absence of sufficient amounts TCTP, cell death rapidly occurs in transformed cells.

Our claim is for a novel method for the treatment of cancer based on pharmacologic induction of conditions that lead to diminution in the amount of TCTP in the cancer cell. The structural hallmarks of the induction of this process are referred to as mitotic catastrophe (MC). MC refers to a condition of the cell characterized by abnormalities in the process of mitosis that lead to cell death by any of the known cell death pathways including apoptosis, necrosis, senescence, and autophagy (Gullizzi et al 2007). We present an example of pharmacologic induction of MC by pan-modification of the extent of phosphorylation of serine and/or threonine regulatory sites in proteins controlling orderly cell replication and division and, finally cell death by reduction in TCTP. Pan-deregulation of serine/threonine phosphorylation is achieved in one instance by the inhibition of protein phosphatase 2A (PP2A) by a small molecule, Compound 100 and/or several of its homologs.

We further show that the opposite modulations of DNA-damage response pathways result paradoxically in enhancement of the effectiveness of cytotoxic chemotherapy. We demonstrate that a small molecule inhibitor (Compound 102) of protein phosphatase 2A (PP2A) (Westermark and Hahn, 2008) activates Plk-1 and Akt-1 and decreases p53 abundance in tumor cells. Combined with temozolomide (TMZ; a DNA-methylating chemotherapeutic drug), compound 102 causes complete regression of glioblastoma multiforme (GBM) (Prados et al, 2008) xenografts without recurrence in 50% of animals (greater than 28 weeks) and complete inhibition of growth of neuroblastoma (NB) (Rubie et al, 2006) xenografts (for at least 7 weeks). Treatment with either drug alone results in only short-term inhibition/regression, with all xenografts resuming rapid growth. Compound 102-inhibition of PP2A increases entry of cancer cells into disordered mitosis with accumulation of cells in the G2M phase and blocks cell cycle arrest in the presence of TMZ.

Previously, it was demonstrated that a shellfish toxin (okadaic acid), which inhibits serine/threonine protein phosphatases PP2A and PP1, inhibits the growth and promotes cell differentiation of primary GBM cells (Park et al, 2007; Lu et al, 2008). Small molecules derived from cantharidin (a vesicant originally extracted from beetles) or its demethylated homolog (nor-cantharidin) mimic the effects of okadaic acid and have anti-cancer activity in vitro and in vivo (Hart et al, 2004; Bonness et al, 2006). Reported clinical benefit of cantharidin is modest and constrained by urologic toxicity and nor-cantharidin, while less toxic, has limited effectiveness (Hart et al, 2004). A series of nor-cantharidin derivatives have been synthesized and their anti-phosphatase and anticancer activity characterized in vitro (Kovach and Johnson, 2008).

Figure 1:
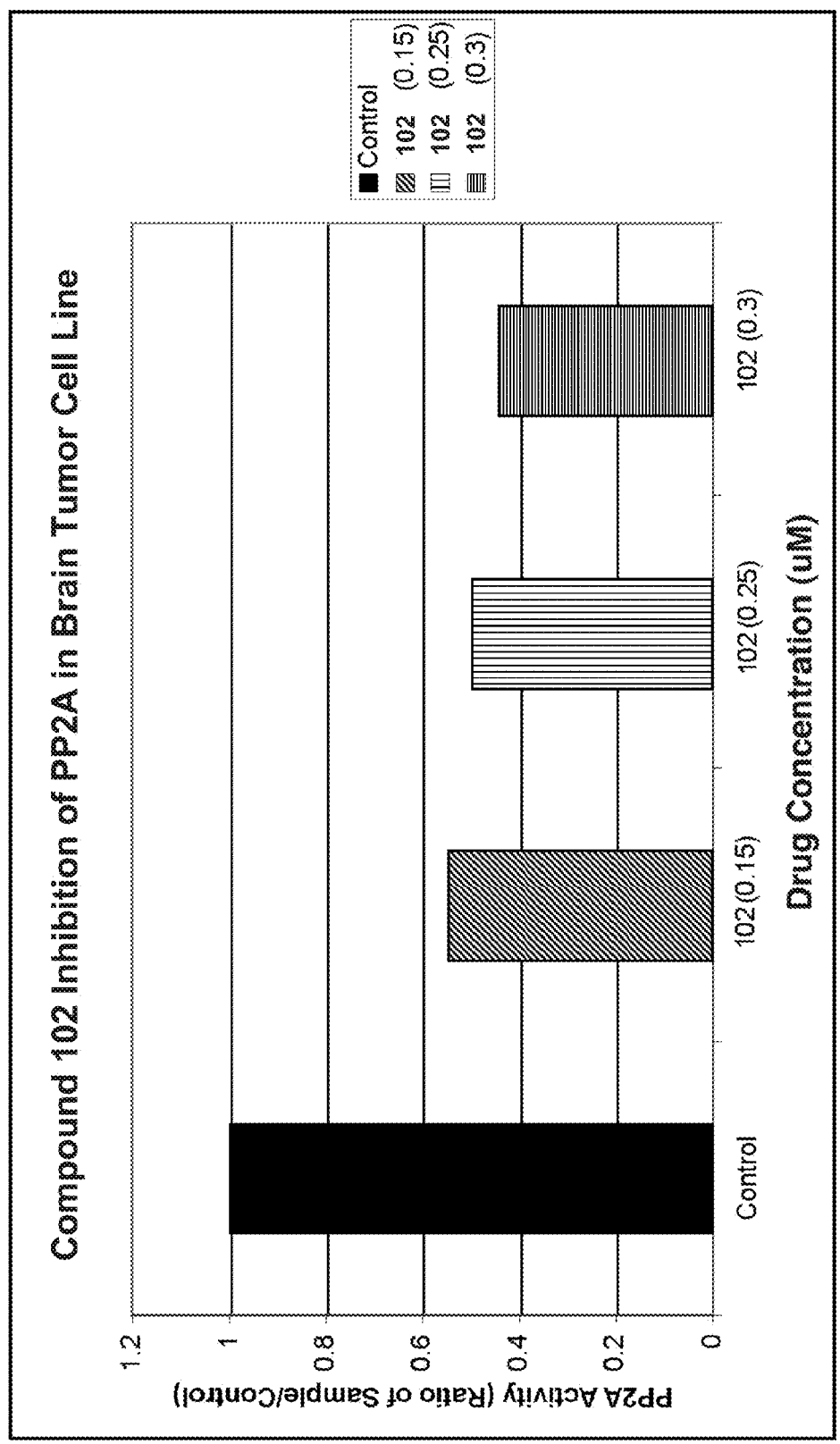
FIG. 1: Inhibition of Protein Phosphatase 2 A (PP2A) in DAOY Cell Line by Compound 102.

Recent work led to the discovery that treatment with the compound, compound 100, and several homologs inhibit the serine/threonine protein phosphatases PP2A (FIG. 1). Compound 102 inhibits PP2A ($IC_{50}$=~0.4 µM) more potently than PP1 ($IC_{50}$=~80 µM) (FIG. 2). Associated with their inhibition of PP2A, Compound 100 and homologs inhibit a variety of human cancer cell types growing in cell culture and growing in vivo as xenografts implanted subcutaneously in SCID mice (FIG. 3 and FIG. 4). Given intraperitoneally (i.p.), a single dose of compound 102 at 1.5 mg/kg inhibits PP2A activity in subcutaneous (s.c.) xenografts of the human GBM cell line, U87 MG, and in normal brain tissue (FIG. 5). In vitro, compound 102 showed dose-dependant inhibition of GBM cell growth ($IC_{50}$=~4 uM) (FIG. 6). Death of these cancer cells is associated with profound disruption of microtubular structures. Such patterns of disordered microtubules during mitosis have been noted after exposure of cancer cells to spindle toxins include such vincristine, vinblastine, taxol, taxotere, ionizing radiation, and DNA damaging agents including anthracyclines and the platinum based compounds. The morphologic appearance of cells displaying these characteristics has been called the mitotic catastrophe phenotype (Castedo et al 2004).

Compound 100 Reduces TCTP Leading to Cancer Cell Death

As shown in the examples that follow, exposure of cancer cells to Compound 100 is associated with increased phosphorylation of several regulatory proteins involved in cell growth and division including Akt-1, Aurora A, N—CoR, Plk-1 and TCTP. In particular, the phosphorylation of the serine/threonine kinase, Plk-1, is associated with the disruption of the homogeneous cytoplasmic distribution of alpha-tubulin (FIG. 7). Surprisingly, we also found that phosphorylation of Plk-1 is associated with a rapid and marked decrease in the amount of TCTP (FIG. 8 and FIG. 9).

TCTP is associated with many functions in the cell and is essential for fetal development (Bommer and Thiele, 2004; Chen et al, 2007B). TCTP is also essential to cancer cell growth but is not critical to the survival of normal adult (untransformed) cells (Chen et al, 2007B). For this reason, TCTP is an attractive target for anti-cancer treatments. Compound 100 and its homologs consistently reduce cellular concentrations of TCTP in cancer cells as early as 4 hours after exposure to the drugs. Even at this early time, loss of TCTP is associated with disruption of microtubular morphology and mitotic disruption (FIG. 7), accompanied subsequently by apoptosis, necrosis, and autophagy. Thus, targeting TCTP with compound 100 is an effective means for inhibiting cancer cell growth and division and therefore for treating cancers.

Compound 100 Preferentially Inhibits Cancer Cells Compared to Normal Cells

The therapeutic benefit of reducing TCTP by treatment with Compound 100 and its homologs is further enhanced by combining treatment with Compound 100 with other anti-cancer treatments including ionizing radiation and agents used for the treatment of cancer that induce abnormalities in DNA and/or that interfere with one or more constituents of the mitotic process. In particular, the anti-cancer activity of X-ray, DNA alkylating agents, DNA intercalating agents, and microtubule stabilizing and disrupting agents is enhanced by treatment with Compound 100. For example, compound 100 enhances cancer cell inhibition by the standard chemotherapeutic agents cisplatin, doxyrubicin and taxol (FIGS. 10A, 10B and 10C).

Most current strategies for pharmacologic treatment of cancers are based on developing drugs or biologicals, primarily antibodies and anti-sense RNAs, that specifically inhibit the activity of an enzyme in a signaling pathway or a gene(s) encoding an enzyme upon which the cancer cell is dependent for growth and survival (Shoshan and Linder 2008). Dependence of a particular type of cancer on excessive activity of a specific signaling pathway has been termed "oncogene addiction" (Lim et al 2008). Interference with the function or abundance of an addicting oncogene may inhibit growth and, in some cases, result in the death of cancer cells that are dependent upon this pathway. Inhibition of a single oncogene, however, is usually insufficient for complete inhibition of a cancer and inhibition is overcome by mutation leading to drug resistance. Older approaches to cancer treatment have involved primarily the use of non-specific agents alone and in combinations of drugs with non-overlapping toxicities to normal tissues to damage DNA or to interfere with cell metabolic pathways including modulation of microtubule stability.

We provide evidence that a more effective means of inhibiting the growth of many, if not all, cancers, is to target master regulatory molecules that affect the function of multiple other regulatory molecules simultaneously. We developed a method to preferentially target cancer cells compared to normal cells by taking advantage of the fact that cancer cells are preparing for or are engaged in active growth and replication.

Coordination and inhibition of molecular events necessary for the survival of the normal cell and the cancer cell are accomplished by counterbalancing chemical activities. Among the most important of these regulatory activities are phosphorylation and de-phosphorylation and acetylation and de-acetylation of proteins controlling many cell functions. By altering the activity of one or a few enzymes controlling phosphorylation and/or acetylation, the activity of complex processes essential to a variety of cell functions can be altered (Johnson et al 2008). Deregulation of systems essential to cell replication should have general applicability for the treatment of multiple types of human cancers, particularly those with a high proportion of cells in active growth and cell division.

PP2A is one of the most abundant and most highly conserved of all proteins, playing a critical role in the life of the cell, primarily during development of the fetus and at times of cell replication in the adult. PP2A modulates the state of phosphorylation of multiple enzymes, some of which are necessary for proper assembly and disassembly of the mitotic machinery (Andrabi et al 2007, van de Weerdt 2005, Westermarck and Hahn 2008, Juntilla et al 2007). When DNA damage occurs during mitosis, PP2A is activated and dephosphorylates the serine/threonine kinase, Plk1. Dephosphorylation of Plk1 in turn halts mitosis providing time for DNA repair before replication is completed. Plk1 has several other activities affecting cell growth and division. It regulates spindle formation and dissolution. An increase in phosphorylation of Plk1 leads to its activation and its phosphorylation of the transcriptionally controlled protein (TCTP), another serine/threonine kinase. Phosphorylation of TCTP leads to a reduction in its abundance and cell death. In the normal cell, upon conclusion of mitosis, Plk1 undergoes dephosphorylation by PP2A that allows the spindle to be disassembled with tubulin undergoing re-polymerization. (Yarm 2002, van Vugt and Medema 2005, Johnson et al 2008). As normal adult cells are not subject to regulation of cell death by the function of TCTP, inhibition of PP2A and destruction of TCTP would preferentially lead to cancer cell death. We developed small molecule inhibitors of PP2A and demonstrated that exposure of cancer cells in vitro and in vivo to a lead compound, compound 100, results in abnormal spindle formation, alteration in cell shape, and incomplete cell division of a variety of human cancer cell types, associated with a decrease in TCTP. Exposure to compound 100 caused dose dependent inhibition of human cancer cell lines derived from the breast, colon, stomach, liver, ovary, prostate, brain, lung, and of leukemias of myeloid and lymphoid lineage and of lymphomas.

The compound 100 series of drugs was developed to target serine threonine protein phosphatase 2A. PP2A regulates the activity of a multitude of cell signaling proteins especially those essential for cell growth, mitosis, and division (Janssens and Goris, 2001). We reasoned that, although PP2A is important to many cell functions (Forester et al, 2007; Westermarck and Hahn 2008), its activity may be particularly important to the cancer cell. Cancer cells (transformed cells) are characterized by alterations in at least some signaling (enzyme) systems that are regulated by phosphorylation and dephosphorylation. Inhibition of PP2A, the major serine threonine phosphatase in the mammalian cell, might disrupt several pathways important to cancer cell survival. The targeting of a multifunctional enzyme such as PP2A that disrupts the function of several (many) pathways important to cancer cell growth and division should be more effective than targeting a single pathway. Thus, inhibition of PP2A will alter many pathways simultaneously rendering the cancer cell less likely to overcome inhibition by bypassing the activity of any one regulatory molecule. Mutational alteration of PP2A itself that bypasses inhibition by compound 100 while maintaining its multiple regulatory capabilities may not be easily accomplished, thereby minimizing the chances of acquired compound 100 resistance.

We found that exposure of cancer cells in vitro and in vivo to a compound 100 results in abnormal spindle formation, alteration in cell shape, and incomplete cell division of a variety of human cancer cell types. This induced deregulation of cell division led to cancer cell death accompanied in some cancers by cell differentiation. Exposure to Compound 100 caused dose dependent inhibition of human cancer cell lines derived from the breast, colon, stomach, liver, ovary, prostate, brain, lung, and of leukemias of myeloid and lymphoid lineage and of lymphomas. We showed that compound 100 treatment of cancer cells induces abnormalities in mitotic spindle structures in a large proportion of the cell mass, and leads to cell death. Thus, the use of compound 100 to decrease TCTP should be effective for the treatment of cancers in general.

In all cell types studied, exposure to compound 100 lead to prompt and marked reduction in TCTP. The mechanism(s) by which compound 100 induces a reduction in TCTP and leads to death of the cancer cell is not known (Gachet et al, 1999: Bommer and Thiele, 2004; Chen et al 2007A). TCTP appears to be critical to the proper functioning of proteins with apoptotic regulatory activity. One such protein is mcl-1, a member of the bcl-2 family (Craig 2002, Warr and Shore, 2008). Mcl-1 is a highly labile molecule important to many developmental processes and is essential for fetal development (Rinkenberger et al 2000; Craig, 2002; Liu et al, 2005). The presence of mcl-1 is also required for the growth and development of T and B lymphocytes (Opfermann et al 2003). The mechanism by which diminished or absent mcl-1 leads to cell death of the embryo is not firmly established. In the absence of mcl-1, however, fetal death occurs at an early stage of development and a variety of cancer cell types undergo apoptosis. Stimulation of cells by cell growth factors is associated with rapid synthesis of mcl-1 and leads to increases in cell survival and/or differentiation. Withdrawal of growth stimuli results in cessation of synthesis and rapid degradation of mcl-1 and cell death (Liu et al 2005).

TCTP binds to mcl-1 and to Bcl-xL, another anti-apoptotic protein (Yang et al 2005). Susini et al (2008) reported that loss of TCTP expression results in a marked increase in cell death during embryogenesis. They suggested that TCTP exerts its anti-apoptotic effect by interfering with Bax dimerization in the mitochondrial membrane. Of crucial importance to TCTP as a target for cancer therapy is the fact that survival of cells of the adult is independent of the abundance of mcl-1 (Liu et al 2005). Thus, loss of TCTP activity induced by compound 100 may be one mechanism by which compound 100 differentially inhibits the cancer cell while sparing damage to the adult (differentiated) normal cell.

Thus, we demonstrated the effectiveness of reducing pharmacologically the abundance of TCTP as a method of cancer treatment. Exposure to compound 100 of glioblastoma, medulloblastoma, B-cell lymphoma, and breast cancer cell lines induced the mitotic phenotype in a large proportion of the cell mass as well as inducing apoptosis and differentiation of other cells. Inhibition of cell growth and cell death by compound 100 was associated with increased phosphorylation of several kinases including Akt and Plk1 as well as reduction of TCTP and mcl-1. The effects of PP2A inhibition on several components of the mitotic machinery have been characterized.

Akt is a kinase target of PI3 kinase that regulates multiple cell functions including the activity of proteins involved in cell cycle progression (Andrabi et al, 2007). Plk1 has multiple activities in cell growth and division and it is critically important for regulating spindle formation and dissolution by regulating the phosphorylation of TCTP (Yarm et al, 2002; van Vugt and Medema 2005). Increased phosphorylation of two specific sites in the Plk1 molecule leads to activation of its serine/threonine kinase activity, causing increased phosphorylation of the kinase, TCTP. These molecular changes are associated with depolymerization of microtubules, a process necessary for rendering tubulin available for spindle formation and the orderly distribution of DNA during mitosis. Upon conclusion of mitosis, Plk1 undergoes dephosphorylation permitting in turn the spindle to be disassembled with tubulin undergoing polymerization. TCTP is associated with microtubule function and has been shown to affect cell-cycle progression among other aspects of cell growth and transformation (Johnson et al, 2008). The Aurora kinases are regulatory proteins demonstrated to have roles in mitosis, affecting centrosome function and bipolar spindle formation (Anand et al, 2003; Jiang et al, 2003; Gautschi et al. 2008). The activity of Cdk1 (Cdc2), a cyclin dependent kinase, is required for cells to exit mitosis (Forester et al 2007). Activation of Cdc2 requires dephosphorylation by the phosphatase Cdc25C, whose activity is dependent upon dephosphorylation by PP2A. Thus, inhibition of PP2A prevents the dephosphorylation of Cdc2, which in turn prevents exit from mitosis (Forester et al 2007).

These and other proteins regulated by serine/threonine phosphorylation mediated by PP2A play critical roles in cell replication, a process essential for development of the fetus and child and maintenance of normal tissue structure and function in the adult but also a process, that when unregulated, underlies the virulent hallmark of the cancer cell, unregulated proliferation (Westermarck and Hahn 2008). Interference with the orderly formation and dissolution of spindle structures by excessive activity of any or all of these molecules results in deregulation of the mitotic process and failure of quantitative apportionment of DNA between daughter cells during cell division.

Compound 100 and its homologs inhibit the action of PP2A allowing excessive phosphorylation of Plk1 and in turn of TCTP leading the formation of spindle structures at inappropriate times with respect to the cell cycle. Interference with the orderly formation and dissolution of spindle structures by excessive activity of any or all of these molecules results in deregulation of the mitotic process and failure of quantitative DNA apportionment between daughter cells during cell division. This deregulation results in an unusual histologic appearance of cancer cells called the mitotic phenotype that is characterized histologically by micronuclei and lobulated nuclei and bizarre abnormal spindle shapes and arrest of cell division. Extreme activation of the mitotic process leads to MC, a state of replicative disorder that has been associated with the death of such affected cells either in mitosis or subsequently in the first or second interphase (Galluzzi et al, 2007). What has not been appreciated is that inhibition of PP2A results in marked diminution of TCTP. It is this event that provides for preferential killing of the cancer cell compared to the normal adult cell.

We also showed that the extent of pharmacological inhibition of PP2A in cancer cells has paradoxical effects of cell growth. At doses of Compound 100 that do not inhibit cancer cell proliferation in cell culture (submicromolar to very low micromolar concentrations), there is slight but clear-cut stimulation of the growth of tumor cells whereas higher doses lead to mitotic catastrophe and cell death. One possible explanation for this phenomenon is that slight inhibition of PP2A increases phosphorylation of molecules regulating entry into mitosis such as Plk1 (Strebhardt and Ullrich, 2007), resulting in an increase in the rate of cells of cells entering mitosis without significantly decreasing the amount of TCTP. Activated Plk1 phosphorylates TCTP leading to a decrease in microtubule stabilization, which normally promotes microtubule reorganization after metaphase (Yarm, 2002; Johnson et al, 2008). At higher doses of Compound 100, however, there is a sharp reduction in TCTP, leading cell death.

Our data are compatible with the idea that many aspects of cell division and cell cycle regulation are not so different between the normal cell and the cancer cell. An intervention such as inhibition of a key regulator of the phosphorylation of multiple enzymes involved in cell division in cell types already prepared for rapid proliferation, such as cancer cells, results in a chaotic mitotic state. Inhibition of PP2A by compound 100 does not force normal cells into excessive replication and, therefore, the normal cell survives compound 100.

Compound 100 Enhances the Activity of Other Anti-Cancer Agents

Mitotic enhancement by treatment with compound 100 not only inhibits the growth and kills cancer cells in and of itself but also renders cancer cells more vulnerable to inhibition and killing by standard modalities of cancer treatment. Abnormal mitotic structures are induced by exposure of cells to X-radiation, to drugs that either interfere with tubulin polymerization or cause hyperpolymerization, and to DNA damaging agents (Ianzini and Mackey, 1998; Morse et al, 2005; Ngan et al, 2008). Despite their significant toxicities, X-ray, spindle poisons, and DNA alkylating agents are among the most widely used and most effective, if not curative, anti-cancer modalities available.

The addition of spindle poisons and/or x-ray during or following exposure of cancers to compound 100 will enhance the extent of cancer cell killing without increasing toxicity to normal cells. Specifically, the combinations of LB-1 combined with ionizing radiation (X-ray therapy), spindle poisons including taxol, vincristine (VCR), vinblastine (VBL), and to DNA damaging agents including anthracyclines, bleomycin, cis-platin, etoposide, temozolomide, and nitrosoureas are more effective anti-cancer regimens than standard regimens of single anti-cancer agents or combinations of agents in the absence of treatment with compound 100. This list of anti-cancer drugs is not meant to be inclusive of all drugs that may be combined to advantage with compound 100. Because the mechanism of action of LB-1 on TCTP and other regulatory molecules is distinct from all other approved anti-cancer regimens, compound 100 may be use to advantage in combination with any of all FDA approved cancer regimens (for list of FDA-approved anti-cancer drugs see: www.accessdata.fda.gov.gov.scripts/cder/onctools/druglist.cfm)

Recently, several investigators have proposed to exploit activation rather than inhibition of PP2A activity as a therapeutic approach to cancers that have impaired PP2A function. Mutationally reduced PP2A activity has been reported in melanomas, cancers of the colon, lung, and breast and certain leukemias (Neviani et al 2007; Perrotti and Neviani 2008). In these cancers, functional inactivation of various subunits of PP2A reduces its phosphatase activity. Certain immunosuppressive drugs, including forskolin and FTY720 enhance PP2A phosphatase activity resulting in inhibition of the growth of these tumors in vitro and in vivo (Perrotti and Neviani 2008). The most striking effect of activation of PP2A phosphatase activity is reported against human blast crisis chronic myelogenous leukemia (CML-BC) and Philadelphia chromosome-positive (phi-positive) acute lymphocytic leukemia (ALL). In a mouse model of disseminated lymphoma-leukemia, Liu et al (2008 showed that treatment with FTY720 daily for two weeks increased survival time. This seemingly paradoxical effect, inhibition of cancer cell growth by enhancement of PP2A activity rather than inhibition of PP2A, underscores the complex concentration dependent effects of modulating the state of phosphorylation of PP2A to reduce oncogenic activity.

Functional impairment of PP2A increases activation of the PKC, PI3 kinase-Akt, and ERK pathway, a mechanism known to contribute to the cancer phenotype through enhanced signaling via this pathway. Partial restoration of PP2A activity in such cells reduces the extent of aberrant signaling leading to inhibition of cell proliferation. In the case of FTY720 there is enhancement of dephosphorylation (reduction of activation) of activated oncogenes and, presumably a reduction of cells entering mitosis. In the case of compound 100 inhibition of PP2A, there is increased phosphorylation (increased activation) of oncogenes driving cells into mitotic chaos and loss of TCTP, leading to cell death.

Tuynder et al (2004) noted that some anti-histaminic and psychoactive drugs are associated with a reduction of TCTP in certain leukemia cell lines and increase the life-span of mice bearing these leukemias. This effect of the anti-histaminic compounds was noted several days after drug exposure. To our knowledge, except for these anti-histaminic and psychoactive drugs and compound 100, no agents have been reported to reduce TCTP activity.

Contrary to the conventional wisdom that inhibition of certain regulatory proteins controlling cell proliferation and division and restoration of acquired defects in DNA-damage defenses are promising approaches to improved cancer treatments, quite the opposite is the case. Namely, accentuation rather than inhibition of cell cycle progression and of defense against DNA-damage enhance the effectiveness of cancer chemotherapy. Global alteration of signal transduction by inhibition of ubitquitous, highly conserved regulatory protein phosphatase, PP2A, accelerates cell cycle progression in cancer cells and blocks defenses against DNA damage imparting curative activity to Temozolomide, a drug with non-curative activity used alone. We also show that the mechanism underlying potentiation of Temozolomide cytotoxicity is a general effect as it applies to the cellular response to one of the most commonly used anti-cancer drugs, doxorubicin.

Because the novel compounds used to inhibit signal transduction pathways affecting cell growth and DNA damage response mechanisms is of a class of pharmacologic agents, PP2A inhibitors, which have been given safely to humans in the past, our approach is successfully applied to the treatment of cancers in humans. The following results demonstrate that, contrary to conventional thinking in drug discovery, simultaneous perturbation of multiple regulatory pathways already disordered in the cancer phenotype differentially affects cancer cells compared to normal cells, preventing recurrence of the cancer after treatment with standard chemotherapeutic agents that are otherwise only partially effective in reducing cancer cell burden.

EXPERIMENTAL DETAILS

Example 1

Reduction of TCTP after Treatment with Compound 100 in U87 and DAOY Cells

Administration compound 100 in U87 glioblastoma multiforme cells grown as subcutaneous xenografts in SCID mice resulted in reduction of TCTP concentration, as detected by 2-dimensional gel electrophoresis. SCID mice were implanted with 5 million U87 cells subcutaneously. On day 26, the mice were administered 1.5 mg/kg of compound 100 by intraperitoneal injection. The animals were sacrificed after 4 hours of treatment and the subcutaneous mass of tumor cells were removed for 2-dimensional gel electrophoretic analysis. A comparable group of mice were exposed to vehicle alone. As shown in FIG. 4, TCTP, subsequently identified by LC-MS-MS, compound 100 treated cells resulted in a diminution in TCTP.

Administration of compound 100 in DAOY medulloblastoma cells in cultures resulted in a reduction in concentration of TCTP and activation of Plk-1, as detected by western blot analysis of cell lystates. DAOY cells in culture were exposed to compound 100 for 4 hours and for 24 hours, and stained for TCTP, p-plk (phosphorylated plk), and total plk on western blots. As early as 4 hours, there is a decrease in the TCTP and an increase of plk-1 phosphorylation, as shown in FIG. 9. In addition, at 24 hours, no TCTP is detectable at loading of comparable concentrations of total cell protein.

Example 2

Inhibition of PP2A Diminishes a Major Defense Against DNA Damage, Cell-Cycle Arrest by p53

Figure 11A:
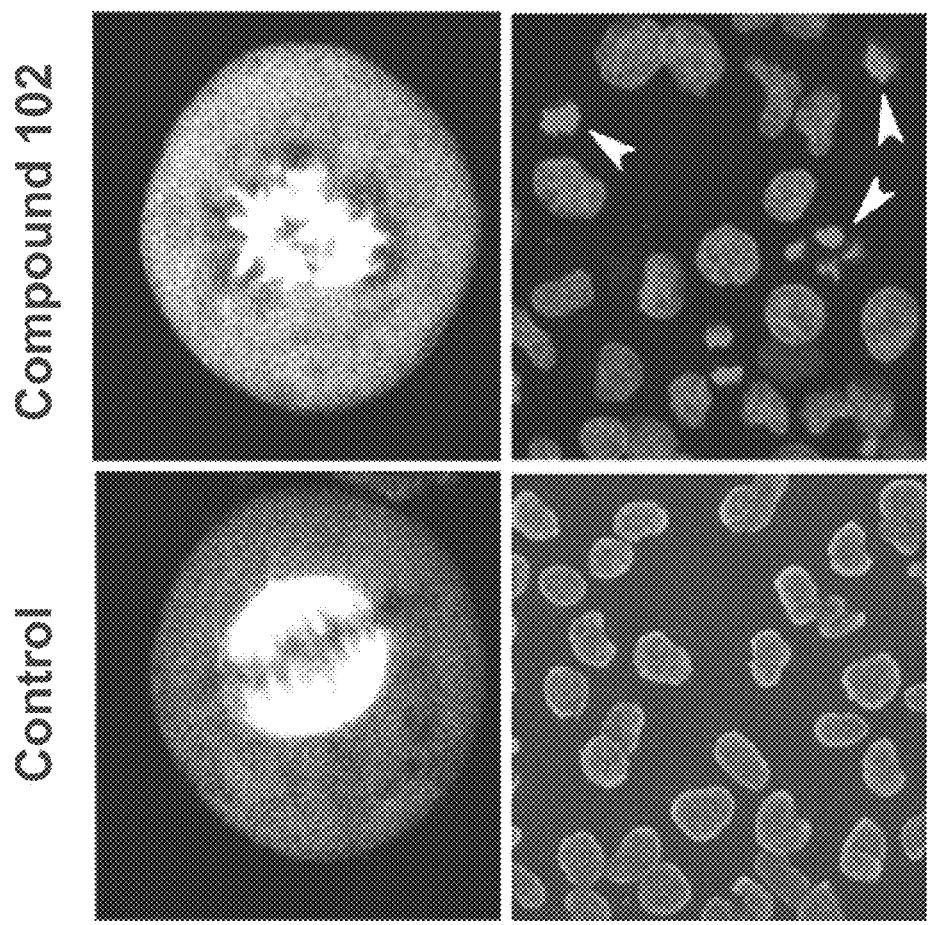
Figure 11B:
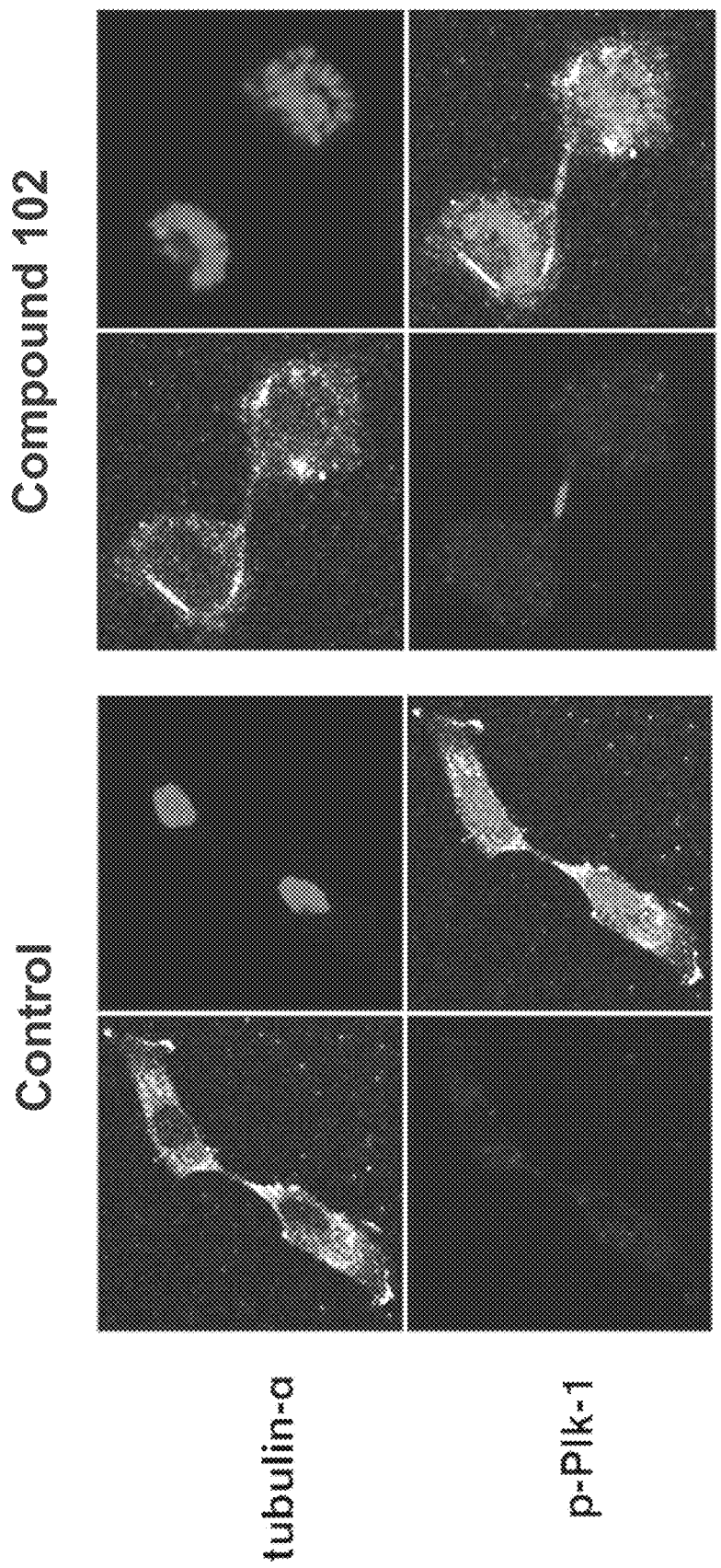
Figure 11D:
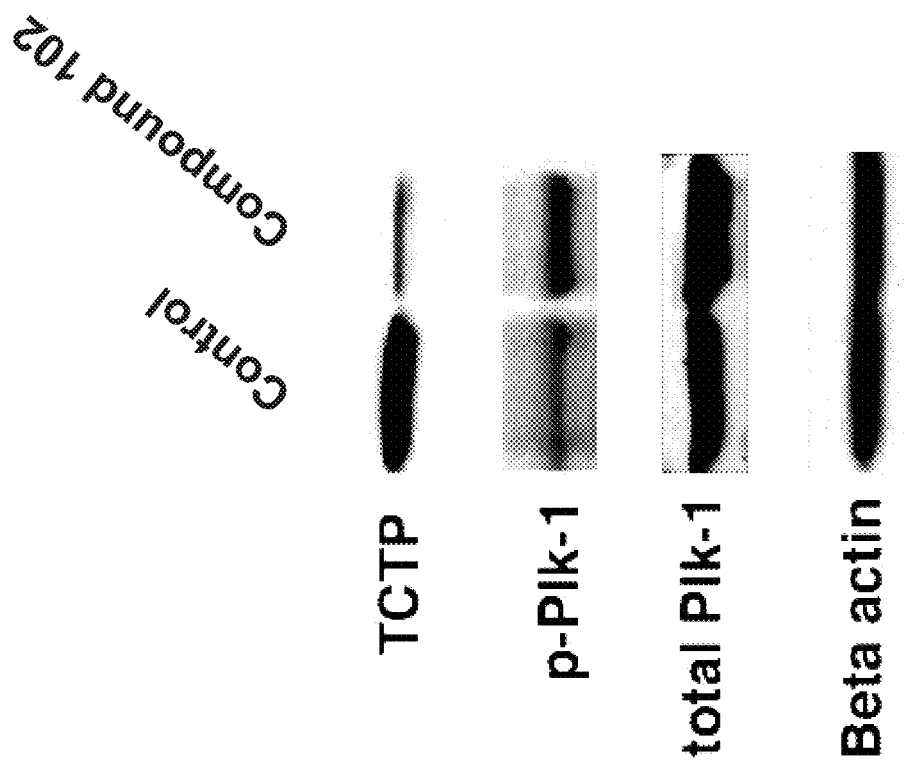
Figure 11C:
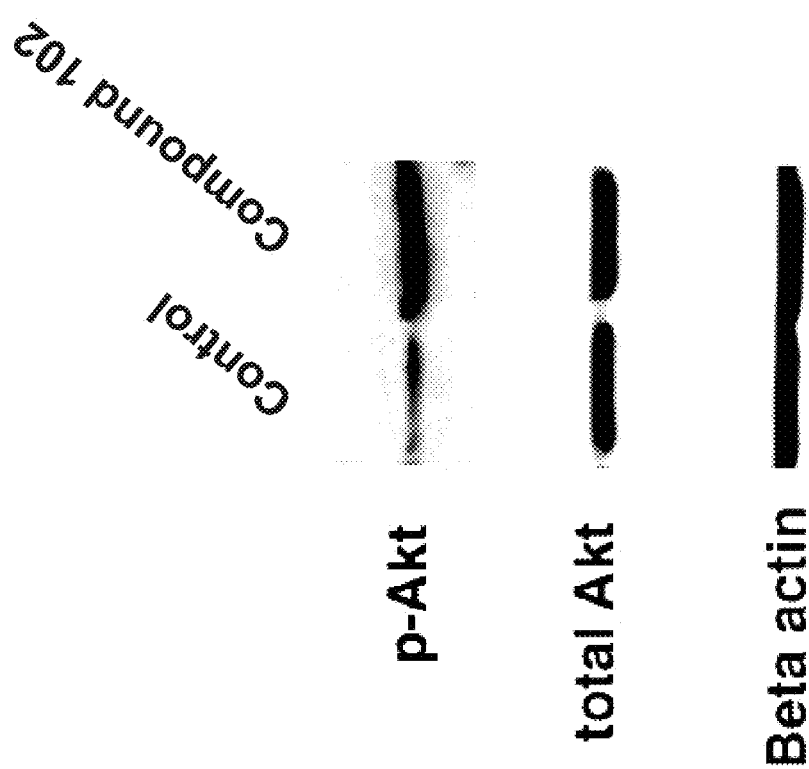
Figure 11E:
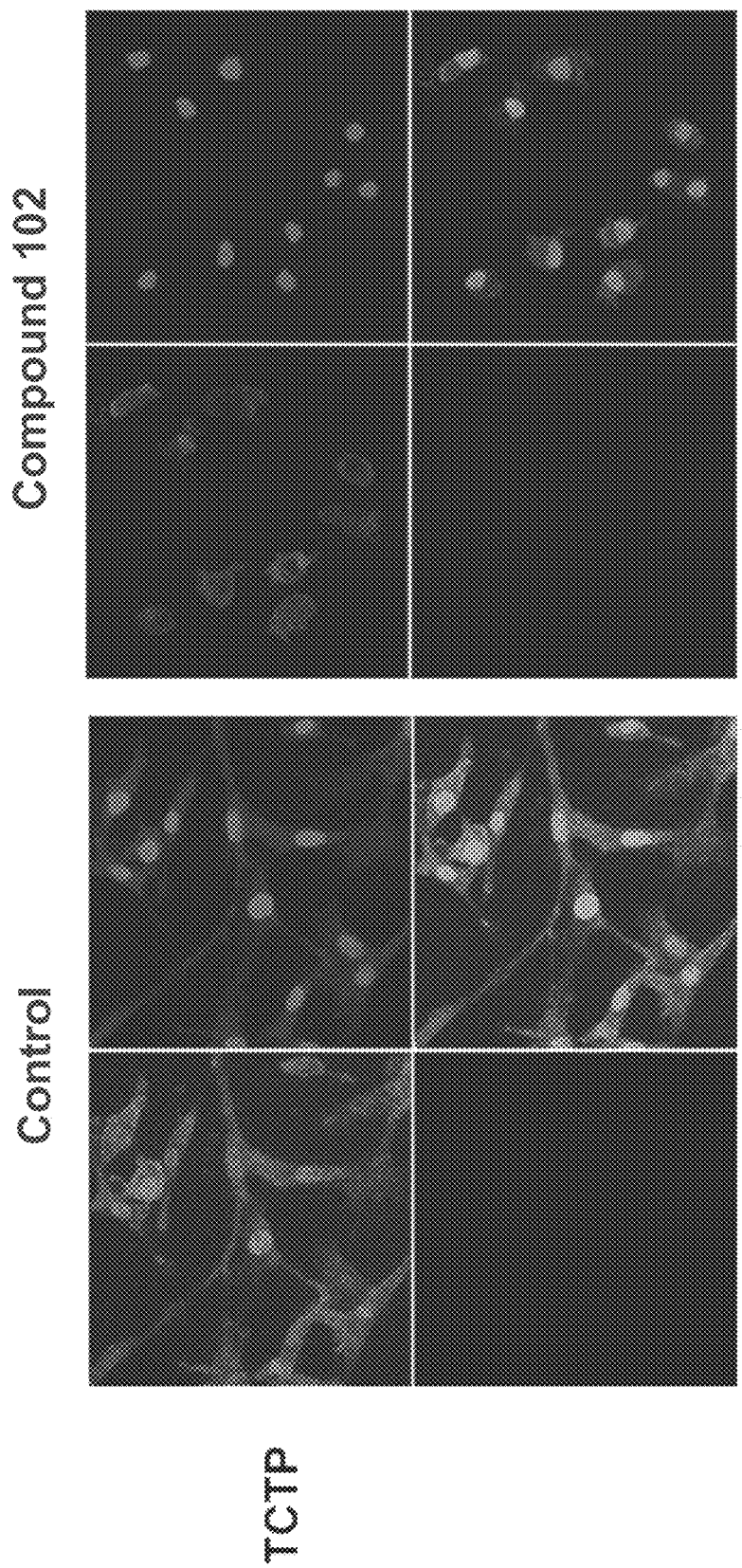
Figure 11F:
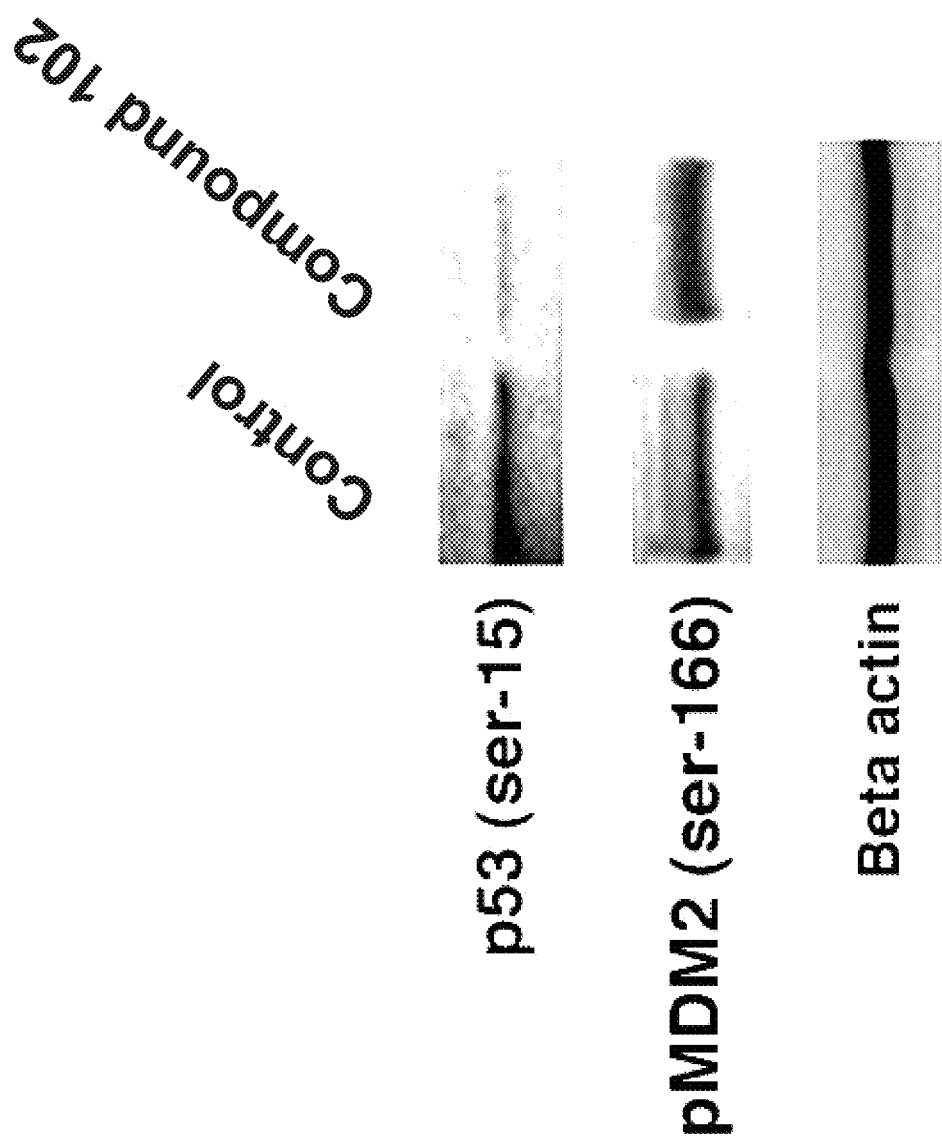
Figure 11G:
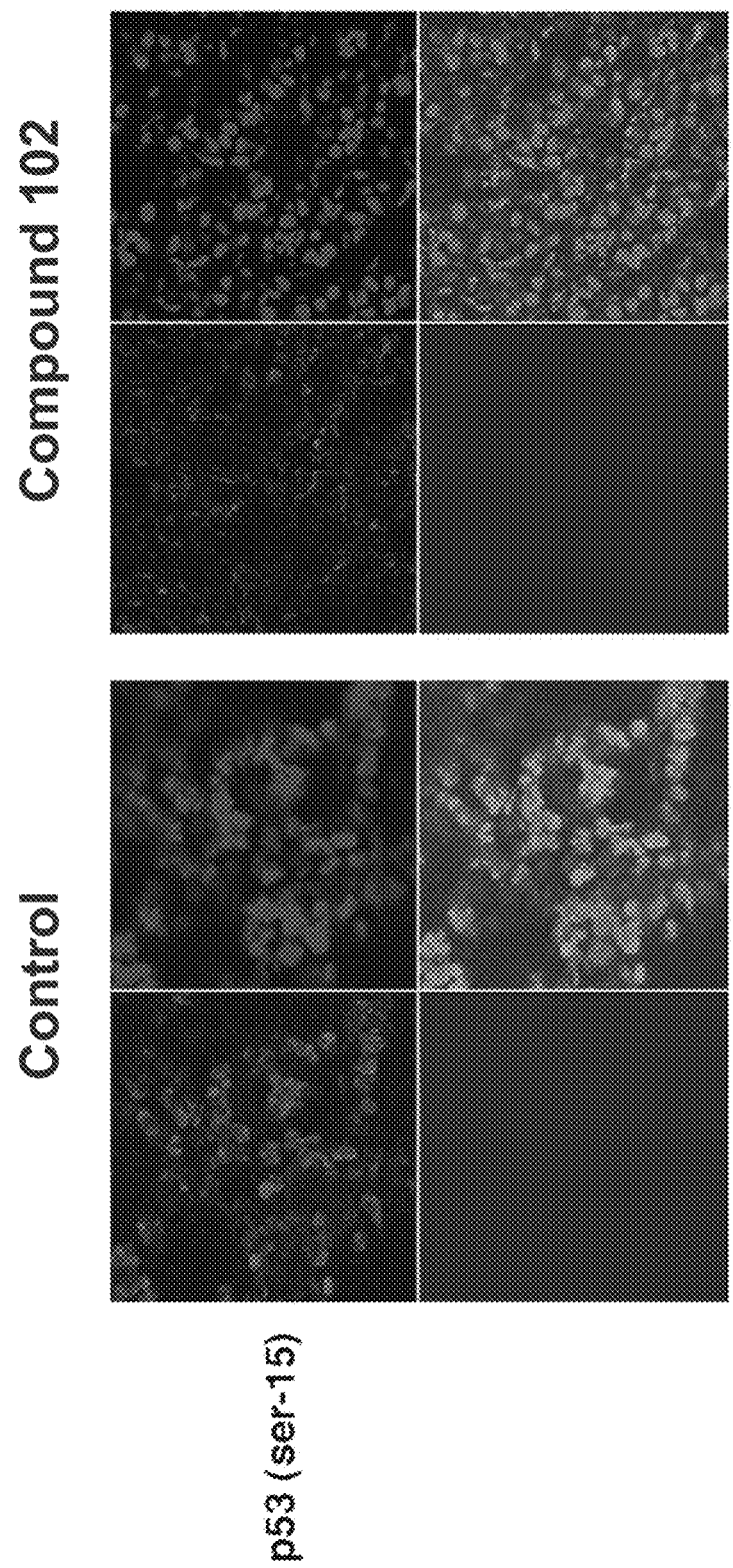

Exposure of U87MG cells in culture to compound 102 resulted in the appearance of disordered microtubules and abnormal mitotic figures that are characteristic of mitotic catastrophe, a form of cell death distinct from apoptosis and cell senescence (Castedo et al, 2004; d'Adda di Fagagna, 2008) (FIG. 11A, 11B). Induction of mitotic catastrophe by compound 102 was associated with increased phosphorylated Akt-1 (pAkt-1, FIG. 11C), increased phosphorylated Plk-1 (pPlk-1) and a marked decrease in translationally controlled tumor protein (TCTP; FIG. 11D). TCTP is an abundant, highly conserved, multifunctional protein that binds to and stabilizes microtubules before and after mitosis and also exerts potent anti-apoptotic activity (Bommer and Thiele, 2004; Yarm, 2002; Susini et al, 2008) (FIG. 11E). Decreasing TCTP with anti-sense TCTPhas been shown by others to enhance tumor reversion of v-src-transformed NIH 3T3 cells and reduction of TCTP is suggested to be the mechanism by which high concentrations of certain anti-histaminics and psychoactive drugs inhibit growth of a human lymphoma cell line (Tuynder et al, 2004).

pAkt-1 phosphorylation at Ser308 indicates downstream activation of the phosphatidylinositol-3-kinase (PI3K) pathway, an event generally considered to be growth-promoting (Brazil et al, 2004). Akt-1 activation, however, may be anti- or proapoptotic depending on the context of cell signaling (Andrabi et al, 2007). Compound 102 inhibition of PP2A increased pAkt-1 and activated Plk-1, a regulator of a mitotic checkpoint and of the activity of TCTP. Compound 102 exposure also increased phosphorylated MDM2, the primary regulator of p53 activity (Vogelstein et al, 2000; Vazquez et al, 2008) and decreased the abundance of p53 (FIG. 11F, 11G.). pAkt-1 can directly phosphorylate MDM2, increasing its stability, and can phosphorylate MDMX, which binds to and further stabilizes MDM2 (Olivier et al, 2008). Thus inhibition of PP2A diminishes a major defense against DNA damage, cell-cycle arrest by p53.

Example 3

Compound 100 Enhances the Cytotoxic Activity of Standard Cytotoxic Chemotherapeutic Drugs Exposure to compound 100 enhanced the inhibition of the human glioblastoma cell line, U373, by cisplatin (FIG. 10A), doxorubicin (FIG. 10B) and Taxol (FIG. 10C), as shown in FIGS. 10A, 10B, and 10C, respectively. Cells were exposed to vehicle alone (control); compound 100 at 2.5 µM, cisplatin at 0.1 µM; doxorubicin at 0.01 µM; or taxol at 0.3 nM alone or to the combination of compound 100 plus each of the standard agents at the same concentrations. In each case, the addition of compound 100 enhanced the effect of the cytotoxic agent at 7 days to an exten greater than that expected from the activity of each agent used alone. The expected percent inhibition from a combination of drugs is calculated by multiplying the actual percent inhibition by each drug alone and comparing that product to the actual percent inhibition caused by the combination of the two drugs (Valeriote, 1975). The expected percent inhibition at 7 days is the product of the inhibition by each agent alone.

For Cisplatin and Compound 100, expected inhibition at 7 days was 66% (93.5 for cisplatin alone×71% for compound 100 alone) versus the actual extent of inhibition by the combination of 50% (FIG. 10A).

For doxorubicin and compound 100, expected inhibition at 7 days was 53% (75.7 5 for doxorubicin alone×71% for compound 100 alone) versus the actual extent of inhibition by the combination of 42.3%. (FIG. 10B)

For taxol and compound 100 expected inhibition at 7 days 80% (114% for Taxol alone×71% for Compound 100 alone) versus the actual extent of inhibition by the combination of 61% (C). (FIG. 10C)

Example 4

The Effects of Compound 102 Combined with Temozolimide (TMZ), a Non-Specific DNA-Methylating Drug To determine the impact of altering DNA-damage defense mechanisms by inhibiting PP2A on the efficacy of cytotoxic chemotherapy, the effects of compound 102 combined with TMZ, a non-specific DNA-methylating drug, routinely used for the palliative treatment of GBM patients (Prados et al, 2008), were studied. SCID mice bearing s.c. xenografts of either the GBM line U87MG or the neuroblastoma line SH-SY5Y were treated with vehicle alone, compound 102 alone, TMZ alone, or both drugs at the same doses and schedules as when given alone. GBM xenografts (one in each flank of five mice) grew rapidly in control animals, requiring sacrifice at 3 weeks. Compound 102 alone minimally delayed growth. TMZ alone caused complete regression for 5 weeks but with regrowth of all xenografts requiring sacrifice of all animals by week 9. The combination of compound 102 and TMZ also caused complete regression of all xenografts but with delayed recurrence and regrowth in 3 animals requiring sacrifice of one mouse at 13 weeks and the other two, at 15 weeks. Two mice, however, had no recurrence in either flank after 7 months, suggesting their cancers had been eliminated. A repeat study confirmed that the 2-drug combination can cause complete regression without recurrence; in this study, three of five animals each implanted with 2 s.c. xenografts remained disease free for over 4 months. No evidence of drug toxicity was noted in either experiment.

Figure 12A:
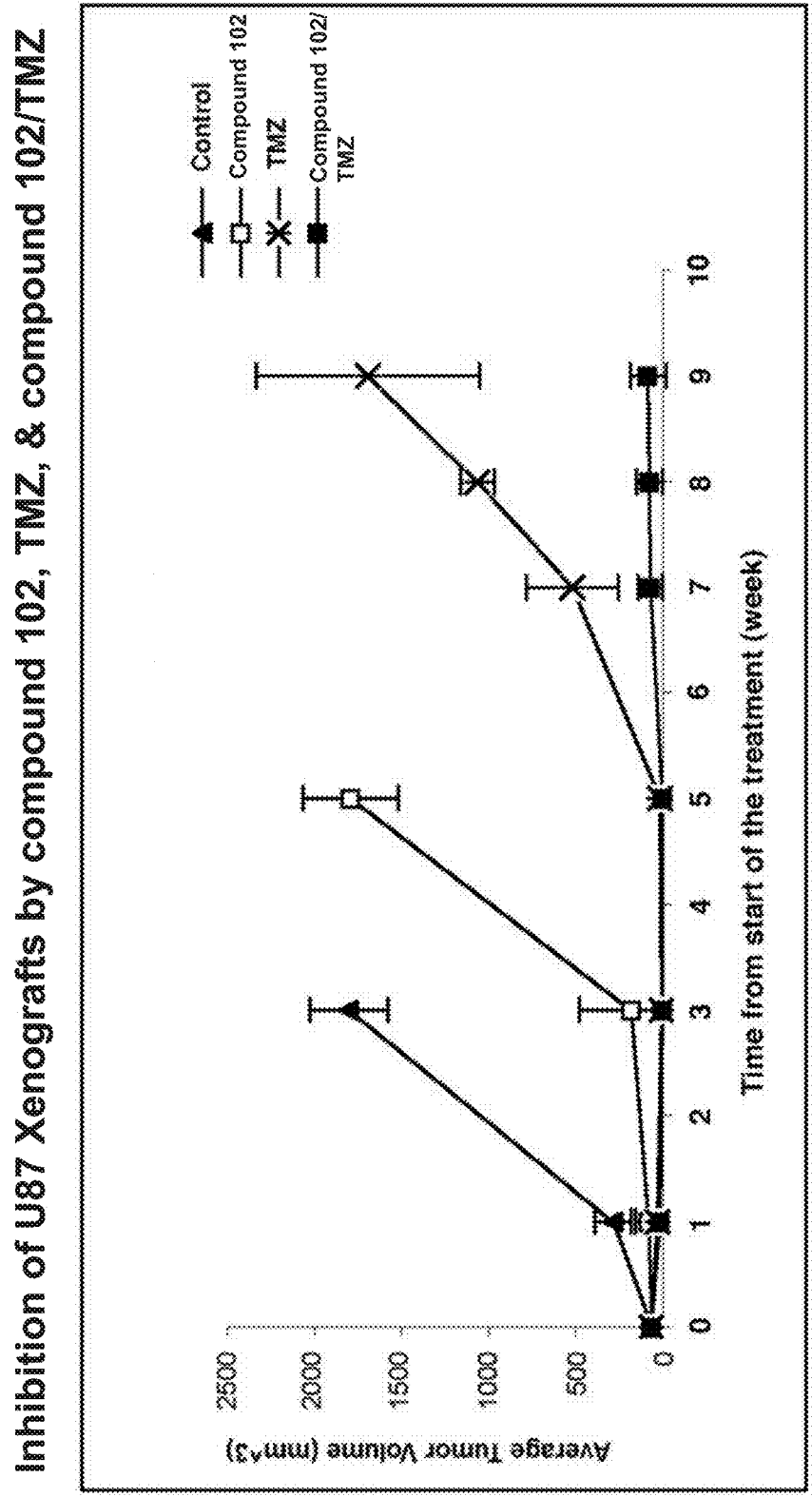
Figure 12B:
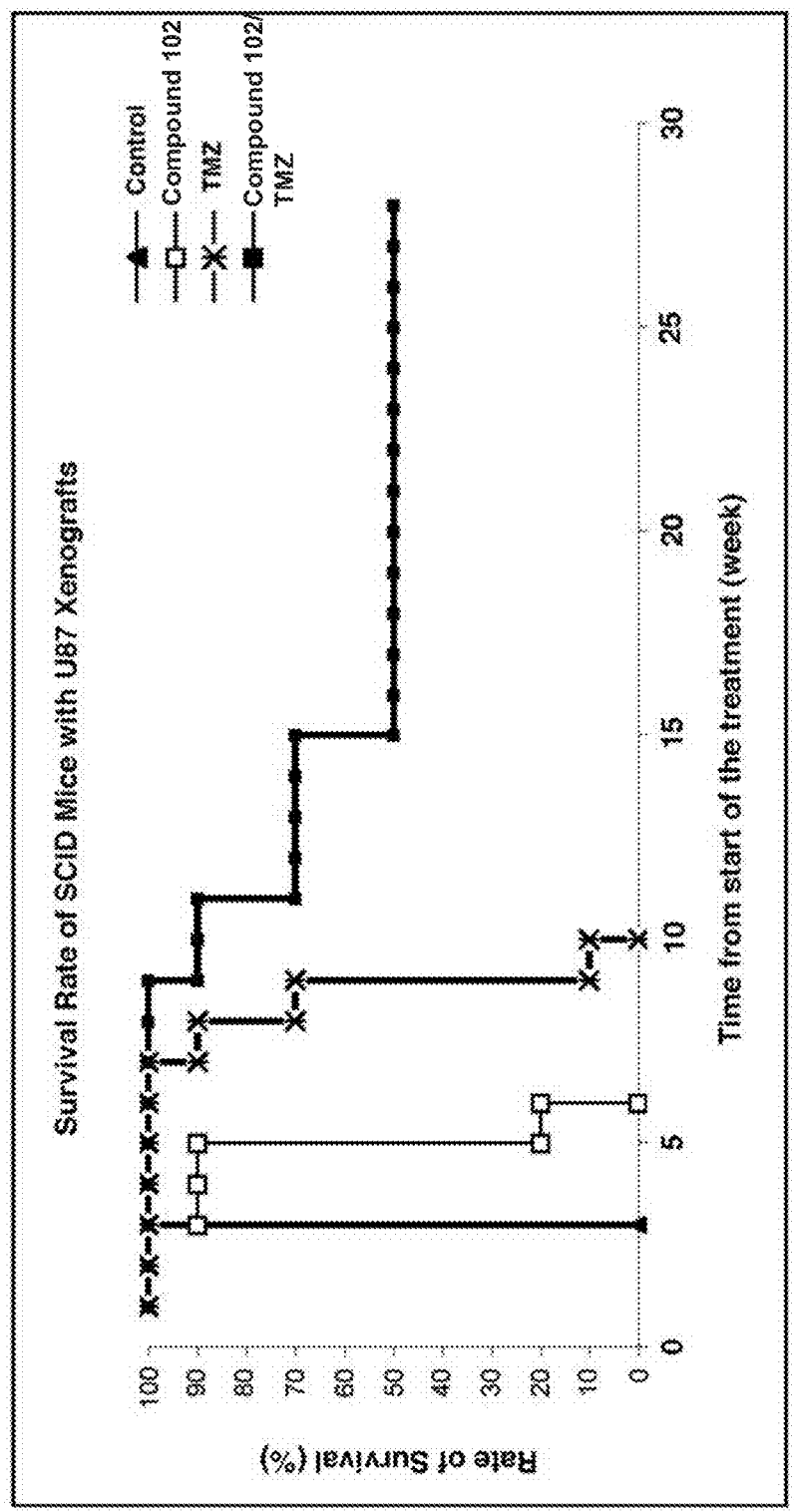
Figure 12C:
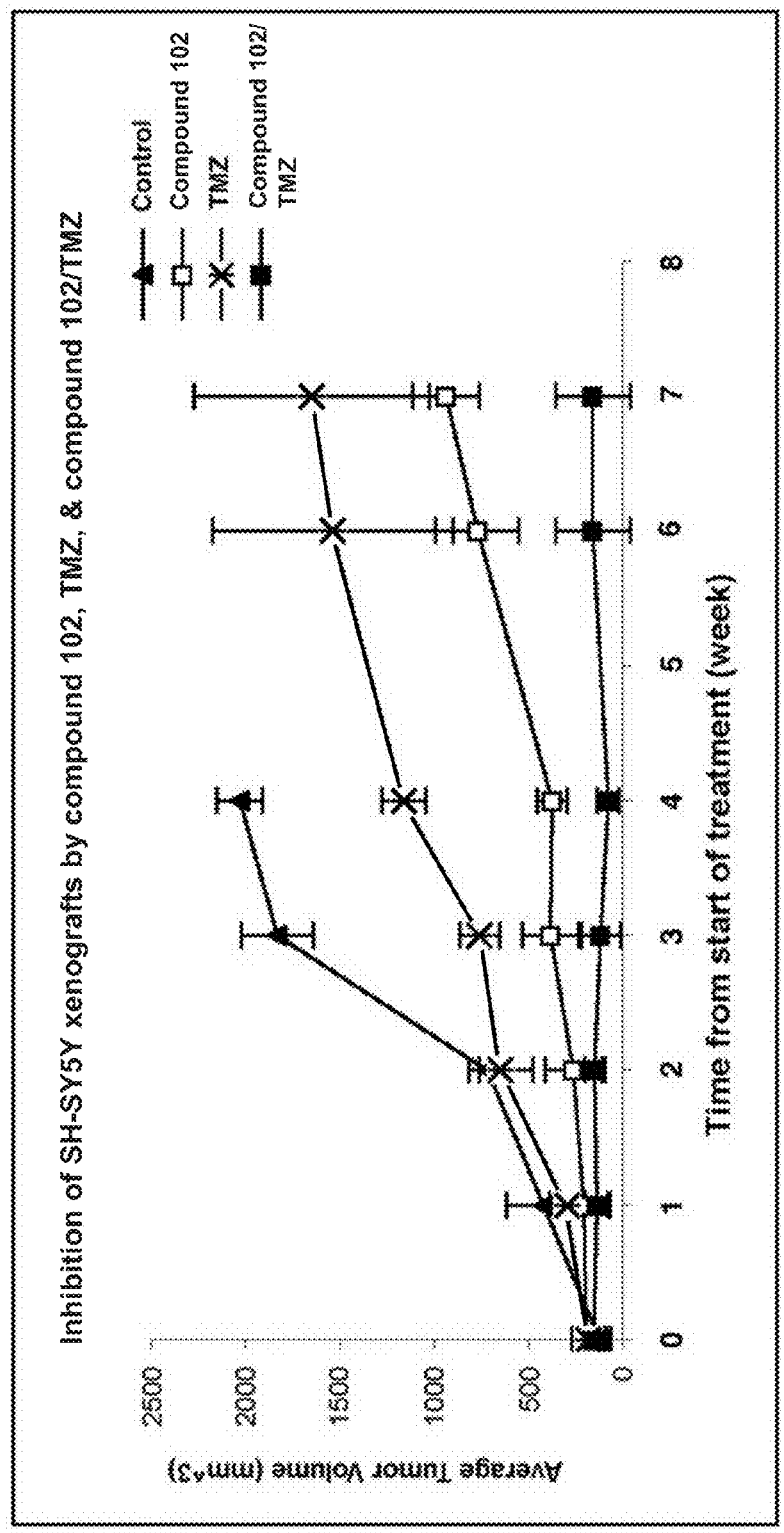
Figure 12D:
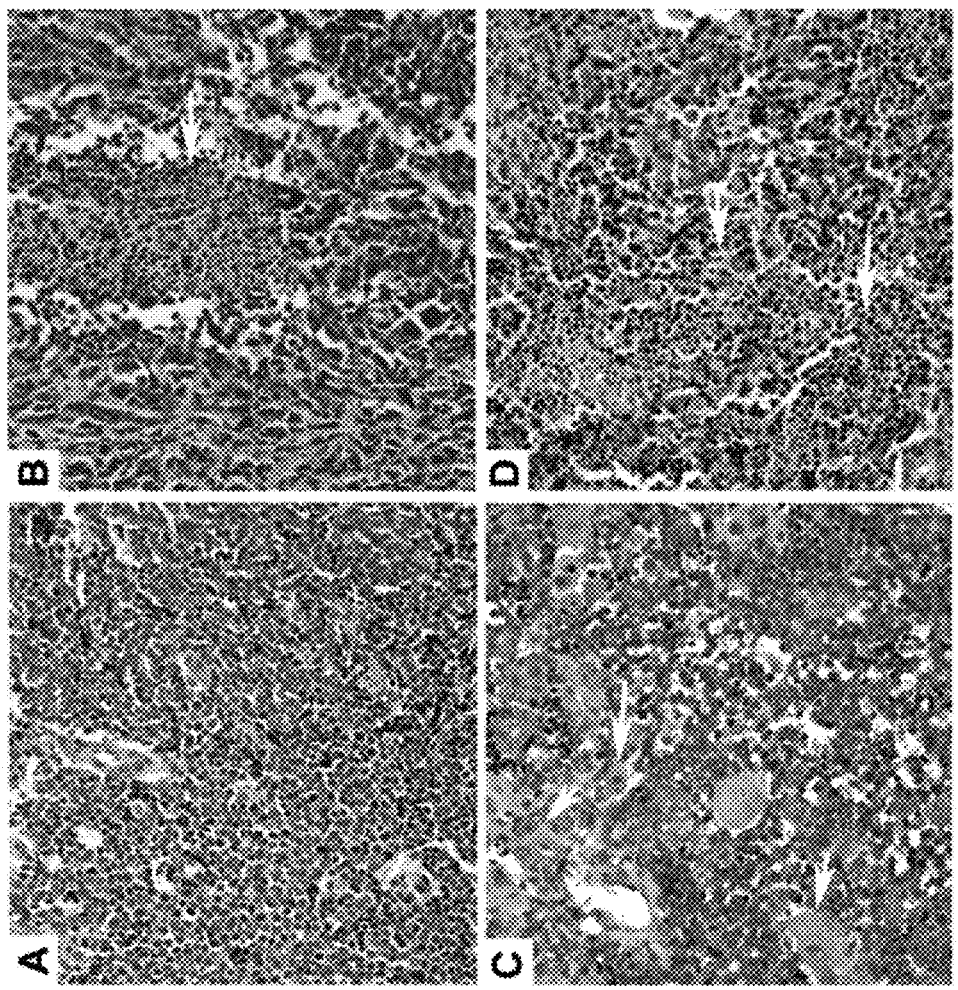
Figure 12E:
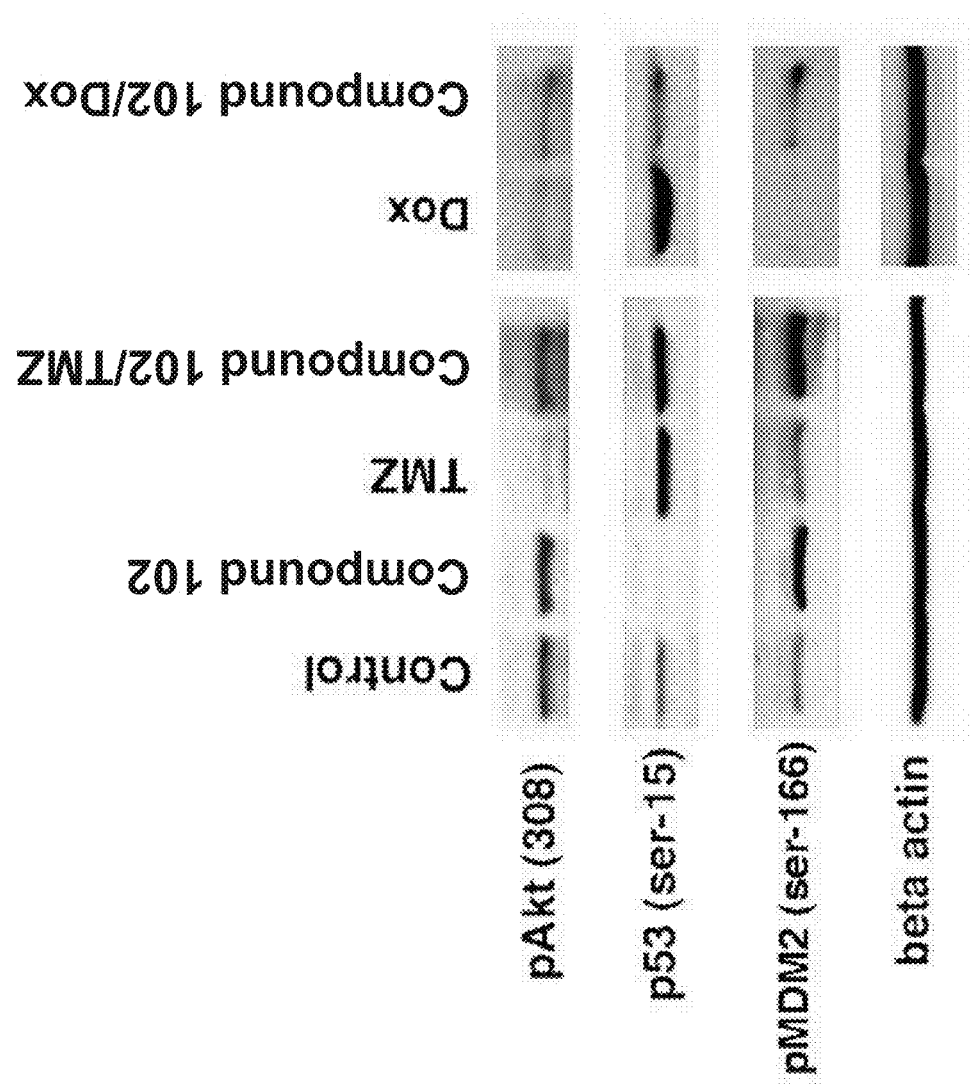

NB xenografts in control animals also grew rapidly, requiring sacrifice at 3 weeks. Compound 102 alone completely suppressed growth for 2 weeks with tumors subsequently growing more slowly than controls, not reaching a size requiring sacrifice by 7 weeks. TMZ alone was less inhibitory than compound 102. The two-drug combination, however, completely inhibited growth, with all xenografts remaining the same size as at the start of treatment for 7 weeks (FIG. 12C). In the three drug treatment arms, some NB xenografts ulcerated by week 4 and all xenografts ulcerated by 7 weeks requiring sacrifice per animal care protocol. None of the xenografts in control animals ulcerated suggesting that tissue breakdown at the xenograft site is an effect of treatment The mechanism responsible for the necrosis, is not known. Histologic examination of NB xenografts 24 hours after exposure to a single i.p. injection of vehicle or drug showed a homogeneous field of healthy appearing tumor cells in vehicle treated animals, whereas compound 102 alone resulted in decreased cell size and pyknotic nuclei in 50% of cells; TMZ alone produced cytoplasmic swelling and vacuolization interspersed with a few (potentially viable) pleomorphic cells in ~50% of cells; and compound 102 plus TMZ resulted in small pyknotic nuclei in more than 90% of cells but without the overt necrosis present after TMZ alone (FIG. 12D.). Thus, the two-drug combination prevented the growth and induced ulceration of the NB xenografts but did not cause complete regression, again without apparent toxicity.

Example 5

Effects of Compound 102 are not Specific to the Type of DNA Damage Caused by TMZ The increase in tumor cell killing by compound 102 plus TMZ raised the possibilities that inhibition of PP2A renders cells more vulnerable to TMZ and/or less efficient in repairing DNA damage because of impaired mitotic and/or DNA damage arrest. The effects of compound 102, TMZ, doxorubicin (DOX), a widely used anti-cancer drug that disrupts DNA replication, compound 102 plus TMZ, and compound 102 plus DOX on the amount of pAkt, p53 and MDM2 in U87MG, a cell line with wild-type p53, and in U373, a cell line with mutant p53 (Short et al, 2007) were assessed by Western blots. Exposure of U87MG cells to compound 102 alone for 24 hours increased both pAkt-1 and MDM2 and eliminated p53; TMZ alone and DOX alone decreased pAkt-1, increased p53, and had little effect on MDM2. Adding compound 102 prevented the decrease in pAkt-1 caused by TMZ alone or DOX alone and increased MDM2 in the face of continued increased expression of p53 (FIG. 12E), indicating that the effects of compound 102 are not specific to the type of DNA damage caused by TMZ.

In vivo, SCID mice implanted with 5 million U87 cells divided into four groups of 10 were treated starting at time 0 when average tumor volume was approximately 60 cubic millimeters by i.p. injection of vehicle alone (100 uL of 50% DMSO in PBS), compound 102 alone, doxorubicin alone, or compound 102 and doxorubicin at various concentrations. Compound 102 in combination with doxorubicin effected the same molecular changes on regulation of cell replication as with TMZ (FIG. 13).

Example 6

Effects of PP2A Inhibition are not Dependent Upon the Presence of Functional p53

Figure 12H:
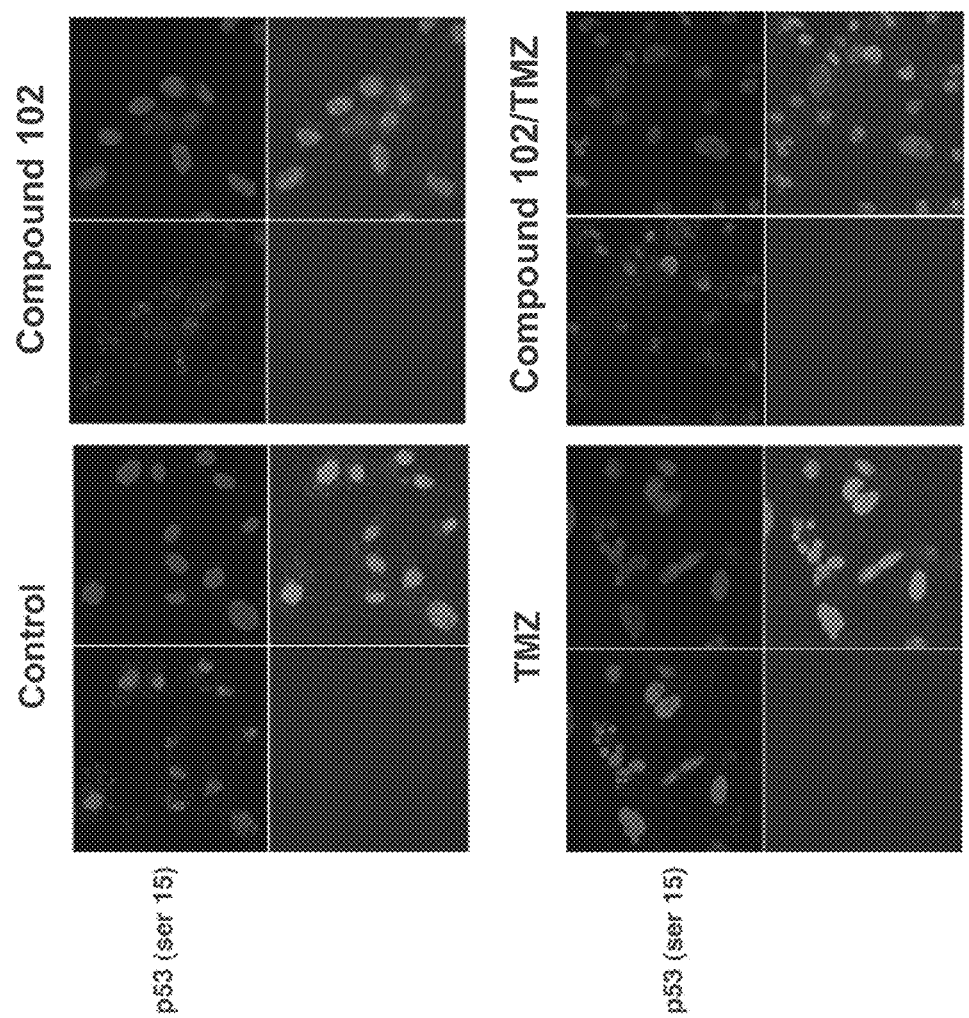

The same molecular changes in pAkt-1, p53, and MDM2 induced by compound 102, TMZ, and compound 102 plus TMZ occurred in U373 cells (FIG. 12F), indicating that the effects of PP2A inhibition are not dependent upon the presence of functional p53. Okadaic acid, at a concentration (2 nM) that is expected to inhibit PP2A and not PP1 (Hart et al, 2004), mimicked the effects of compound 102 on pAkt-1 and on mutant p53 in U373 cells (FIG. 12G), supporting the hypothesis that the effects of compound 102 result from inhibition of PP2A. The reduction of intracellular levels of p53 by exposure to compound 102 alone and in combination with TMZ was confirmed by immunofluorescence staining of U87 cells (FIG. 12H).

Example 7

Changes in Cell Cycle are not Dependent on the Specific Action of the DNA Damaging Agent and/or on the Presence of Functional p53

We analyzed cell cycle patterns of U87MG and U373 cells 48 hours after exposure to TMZ or DOX alone and in combination with compound 102. In U87MG cells, exposure to TMZ alone decreased the number of G1 phase cells, markedly increased S phase cells, and had little effect on G2/M phase cells. Exposure to compound 102 alone also decreased G1, modestly increased S, but prominently increased G2/M. Exposure to either of the two-drug combinations resulted in patterns comparable to compound 102 alone, namely decreased G1 with greatly increased S and G2/M (FIG. 14A). Compared to U87MG cells, control U373 cells had slightly greater G1 and smaller G2/M compartments and a comparable S component. Compound 102 alone had no effect on this profile. Exposure to TMZ or DOX alone reduced G1 and G2/M and greatly increased S. Exposure to either of the two-drug combinations markedly decreased G1 and increased G2/M. (FIG. 14B). There were some quantitative differences but the primary effects of compound 102 combined with TMZ or with DOX were similar in both cells lines, indicating that the changes in cell cycle are not dependent on the specific action of the DNA damaging agent and/or on the presence of functional p53.

Inhibition of PP2A by compound 102 triggers a chain of alterations in cancer cell signaling that accelerates inappropriate entry of cells into mitosis and, at the same time, impairs arrest of cell cycle at G1 and G2M (FIG. 14C.). In the face of chemotherapy-induced DNA damage and disordered cell replication, compound 102 up-regulates Akt-1, which has the potential to stimulate cell growth, and, at the same time, interferes with p53-mediated cell cycle arrest by stabilizing MDM2 (Lopez-Pajares et al, 2008). An increase in pAkt-1 activates Plk-1, interfering with activation of a checkpoint at G2/M (Lei and Erikson, 2008; Garcia-Echeverria and Sellers, 2008) and activating TCTP by phosphorylation (Bommer and Thiele, 2004). Phosphorylation of TCTP decreases the stabilization of microtubules (Bommer and Thiele, 2004; Yarm, 2002), which may contribute to the development of mitotic catastrophe after exposure of cancer cells to compound 102. It has been found, however, that in the cancer cell lines and xenografts studied, pPlk-1 phosphorylation of TCTP results in a marked reduction in TCTP abundance. Loss of TCTP expression during embryogenesis increases cell death (Chen et al, 2007), presumably by reduction of TCTP anti-apoptotic activity that is mediated by interference with Bax dimerization in the mitochondrial membrane (Susini et al, 2008). Loss of TCTP induced by inhibition of PP2A may enhance cancer cell killing by the same mechanism.

The foregoing results indicate that inhibition of PP2A increases the anti-cancer activity of TMZ to the level of cure in up to 50% of animals implanted with GBM xenografts and completely suppresses the growth of NB xenografts. When toxicity is not limiting in humans, inhibition of PP2A in cancers is a general method for improving the effectiveness of anti-cancer regimens that target DNA and/or components of the mitotic process. The forgoing results indicate that pharmacologic inhibition of PP2A enhances the effectiveness of cancer treatments that damage DNA or disrupt components of cell replication by interfering with multiple DNA-damage defense mechanisms.

REFERENCES

1. Andrabi, S., Gjoerup, O. V., Kean, J. A., Roberts, T. M. & Schaffhausen, B. Protein phosphatase 2A regulates life and death decisions via Akt in a context-dependent manner. *Proc. Natl. Acad. Sci. USA* 104, 19011-19016 (2007).
2. Bommer, U A, and Thiele, B J (2004), "The translationally controlled tumor protein (TCTP)," International Journal of Biochemistry & Cell Biology, Vol. 36 pp. 379-385.
3. Bonness, K. et al. Cantharidin-induced mitotic arrest is associated with the formation of aberrant mitotic spindles and lagging chromosomes resulting, In part, from the suppression of PP2Aα. *Mol. Cancer. Ther.* 5, 2727-2736 (2006).
4. Brazil, D. P., Yang, Z.-Z. & Hemmings, B. Advances in protein kinase B signalling: AKTion on multiple fronts. *Trends in Biochemical Sciences* 29, 233-242 (2004).
5. Casteda, M et al. (2004), "Cell death by mitotic catastrophe: a molecular definition," Oncogene, Vol. 23, pp. 825-2837.
6. Chen, S et al. (2007A). "Mcl-1 Down-regulation Potentiates ABT-737 Lethality by Cooperatively Inducing Bak Activation and Bax Translocation," American Association for Cancer Research, Vol. 6, pp. 782-791.
7. Chen, S H et al. (2007B). "A Knockout Mouse Approach Reveals that TCTP Functions as an Essential Factor for Cell Proliferation and Survival in a Tissue- or Cell Type-specific Manner." Molecular Biology of the Cell. Vol. 18, pp. 2525-2532.
8. Craig, R W (2002). "MCL1 provides a window on the role of the BCL2 family in cell proliferation, differentiation and tumorigenesis." Leukemia, Vol. 16, pp. 444-454.
9. D'Adda di Fagagna, F. Living on a break: cellular senescence as a DNA damage response. Nature Reviews Cancer 8, 512-522 (2008).
10. Forester C M et al. (2007) "Control of mitotic exit by PP2A regulation of Cdc25C and Cdk1." Proc. Natl. Acad. Sci., Vol. 112, pp. 1257-1271.
11. Gachet Y et al. (1999). "The growth-related, translationally controlled protein P23 has properties of a tubulin binding protein and associates transiently with microtubules during the cell cycle." Journal of Cell Science, Vol. 112, pp. 1257-1271.

12. Garcia-Echeverria, C. & Sellers, W. A. Drug discovery approaches targeting the P13K/Akt pathway in cancer. *Oncogene* 27, 5511-5526 (2008).
13. Hart, M. E., Chamberidis, A. A., Walkom, C., Sakoff, J. A. & McCluskey, A. Modified nor-cantharidins: synthesis, protein phosphatases 1 and 2A inhibition, and anti-cancer activity. *Bioorg. Med. Chem. Letters.* 14, 1969-1973 (2004).
14. Hirose, Y., Katayama, M., Mirzoeva, O. K., Berger, M. & Pieper, A. O. Akt activation suppresses Chk2-mediated, methylating agent-induced G2 and protects from temozolomide-induced mitotic catastrophe and cellular senescence. *Cancer Res.* 65, 4861-4869 (2005).
15. Ianzini, F and Mackey, M A ((1998). "Delayed DNA damage associated with mitotic catastrophe following X-irradiation of HeLa S3 cells." Mutagenesis, Vol. 13, No. 4 pp. 337-344.
16. Janssens, V and Goris, J (2001). "Protein phosphatase 2A: a highly regulated family of serine/threonine phosphatases implicated in cell growth and signaling." Biochemistry, Vol. 353, pp. 417-439.
17. Johnson, T M, et al. (2008). "Plk1 Activation of Step 20-like Kinase (Slk) Phosphorylation and Polo-Box Phosphopeptide Binding Assayed with the Substrate Translationally Controlled Tumor Protein (TCTP)". Biochemistry, Vol. 47, pp. 3688-3696.
18. Kovach, J. S. & Johnson, F. Patent Application: WO 2008/097561.
19. Lei, M. & Erikson, A. L. Plk1 depletion in nontransformed diploid cells activates the DNA-damage checkpoint. *Oncogene* 27, 3935-3943 (2008).
20. Lim, K H et al. (2008). "Tumor maintenance is mediated by eNOS." Nature 452 (7187, pp. 646-9.
21. Liu, H et al. (2005). "Stabilization and Enhancement of the Antiapoptic Activity of Mcl-1 by TCTP." Molecular and Cellular Biology, Vol. 25, pp. 3117-3126.
22. Liu, X., Lei, M. & Erikson, A. L. Normal cells, but not cancer cells, survive severe Plk1 depletion. Mol. & Cell. Biol. 26, 2093-2108 (2006).
23. Lopez-Pajares, V., Kim, M. M. & Yuan, Z-M. Phosphorylation of MDMX mediated by Akt leads to stabilization and induces 14-3-3 binding. *J. Biol. Chem.* 283, 13707-13713 (2008).
24. Lu, J. et al. LB-1 an inhibitor of serine-threonine protein phosphatase PP2A, suppresses the growth of glioblastoma cells in vitro and in vivo. *99h AACR annual meeting*, Abstract #5693, (2008).
25. Morse, D L et al. (2005). "Docetaxel induces cell death through mitotic catastrophe in human breast cancer cells." Mol. Cancer. Ther, Vol 4(10), pp. 1495-1504.
26. Neviani P et al. (2007). "FTY720, a new alternative for treating blast crisis chronic myelogenous leukemia and Philadelphia chromosome-positive acute lymphocytic leukemia." The Journal of Clinical Investigation, Vol. 117, Number 9, pp. 2408-2421.
27. Ngan, C Y et al. (2007). "Oxaliplatin induces mitotic catastrophe and apoptosis in esophageal cancer cells." Cancer Sci., Vol. 99, no. 1, pp. 129-139.
28. Olivier, M. et al. Recent advances in p53 research: an interdisciplinary perspective. *Cancer Gene Therapy* 19 Sep. 2008; doi:10.1038/cgt.2008.69, pages 1-12 (2008).
29. Olmos, D., Swanton, C. & de Bono, J. Targeting polo-like kinase: learning too little too late? *J. Clin. Oncology* 27, 5497-5499 (2008).
30. Park, D. M. et al. N—CoR pathway targeting induces glioblastoma derived cancer stem cell differentiation. *Cell Cycle* 6, 467-70 (2007).
31. Perrotti, D and Neviani, P (2008). "Protein phosphatase 2A (PP2A), a drugable tumor suppressor in Phl(+) leukemias." Cancer Metastasis, Rev. DOI 10.1007/S10555-008-9119-x.
32. Prados, M. D. et al. Phase II study of Erlotinib plus Temozolomide during and after radiation therapy in patients with newly diagnoses glioblastoma multiforme or gliosarcoma. *J. Clin. Oncology.* Dec. 15, 2008. as 10.1200/JCO.2008.18.9639, 1-6 (2008).
33. Rinkenberger. J et al. (1999). "Mcl-1 deficiency results in peri-implantation embryonic lethality." Genes and Development, Vol. 14, pp. 23-27.
34. Rubie, H. et al. Phase II study of temozolomide in relapsed or refractory high-risk neuroblastoma: a joint Societe Française des Cancers de l'Enfant and United Kingdom Children Cancer Study Group-New Agents Group Study. *J. Clin. Oncol.* 24, 5259-5264 (2006).
35. Short, S. C. et al. DNA repair after irradiation in glioma cells and normal human astrocytes. *Neuro-Oncology* 9, 404-411 (2007).
36. Shoshan, M C (2008). "Target specificity and off-target effects as determinants of cancer drug efficacy." Expert Opin Drug Metab Toxicol, Vol. 4 No. 3, pp. 273-80.
37. Susini, L et al. (2008). "TCTP protects from apoptotic cell death by antagonizing bax function." Cell Death and Differentiation, 15 Feb. 2008:DOI:10.1038/cdd.2008.18.
38. Strebhardt, K and Ullrich, A (2006). "Targeting polo-like kinase 1 for cancer therapy." Nature Reviews, Vol. 6, pp. 321-330.
39. Valeriote, F., (1975) Cancer Chemother. Rep., Vol 59, pp. 895-900.
40. Vazquez, A., Bond, E E, Levine, A. J. & Bond, G. L. The genetics of the p53 pathway, apoptosis and cancer therapy. *Nature Rev. Cancer* 7, 979-987 (2008).
41. Vogelstein, B., Lane D. & Levine, A. J. Surfing the p53 network. *Nature* 408, 307-310 (2000).
42. Warr, M. and Shore, G C. (2008). "Unique Biology of Mcl-1: Therapeutic Opportunities in Cancer." Current Molecular Medicine, Vol. 8, No. 2, pp. 138-147.
43. Westermarck, J. and Hahn, W C. (2008). "Multiple pathways regulated by the tumor suppressor PP2A in transformation." Trends in Molcular Medcine, DOI: 10.1016/1.molmed.2008.02.001.
44. Yarm, F R, (2002). "Plk Phosphorylation Regulates the Microtubule-Stabilizing Protein TCTP." Molecular and Cellular Biology, Vol. 22, pp. 6209-6621.
45. Yang, Y et al. (2005). "An N-terminal region of translationally controlled tumor protein is required for its antiapoptotic activity." Oncogene Vol. 24, pp. 4778-4788.
46. Tuynder, M. et al. (2002). "Biological models and genes of tumor reversion: Cellular reprogramming through tpt1/TCTP and SIAH-1." PNAS, Vol. 99, pp. 14967-14981.
47. Tuynder, M. et al. (2004). "Translationally controlled tumor protein is a target of tumor reversion." PNAS, Vol. 101, pp. 15364-15369.

What is claimed is:

1. A method of inhibiting proliferation or inducing apoptosis of a cancer cell in a human subject which overexpresses TCTP comprising administering to the subject a) a compound, wherein the compound has the structure

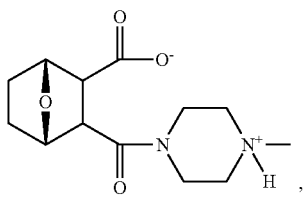 [SMILES: C[NH+]1CCN(C(=O)C2C(C(=O)[O-])[C@H]3CC[C@@H]2O3)CC1]

or a salt, enantiomer or zwitterion of the compound, in an amount effective to inhibit the proliferation or to induce apoptosis of the cancer cell, and b) an anti-cancer agent in an amount effective to inhibit the proliferation or to induce apoptosis of the cancer cell, wherein the cancer is selected from adrenocortical cancer, bladder cancer, osteosarcoma, cervical cancer, esophageal, gallbladder, head and neck cancer, Hodgkin lymphoma, non-Hodgkin lymphoma, renal cancer, melanoma, pancreatic cancer, rectal cancer, thyroid cancer, throat cancer, breast cancer, lung cancer and prostate cancer.

2. The method of claim 1, wherein the cancer is selected from breast cancer, lung cancer, prostate cancer, and head and neck cancer.

3. The method of claim 2, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, alitretinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovrin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide, VM-26, testolactone, thalidomide, thioguanine, 6-TG, thiotepa, topotecan, toremifene, tositumomab, trastuzumab, tretinoin ATRA, uracil mustard, valrubicin, vinblastine, vincristine, vinorelbine, vorinostat, zoledronate, and zoledronic acid.

4. The method of claim 2, wherein the anti-cancer agent is ionizing radiation.

5. The method of claim 2, wherein the anti-cancer agent is x-radiation.

6. The method of claim 2, wherein the anti-cancer agent is docetaxel.

7. The method of claim 1, wherein the cancer is selected from adrenocortical cancer, bladder cancer, osteosarcoma, cervical cancer, esophageal, gallbladder, head and neck cancer, Hodgkin lymphoma, non-Hodgkin lymphoma, renal cancer, melanoma, pancreatic cancer, rectal cancer, thyroid cancer, and throat cancer.

8. The method of claim 7, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, alitretinoin, allopurinol, altretamine, amifostin, anakinra, anastrozole, arsenic trioxide, asparaginase, azacitidine, bevacizumab, bexarotene, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovrin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide, VM-26, testolactone, thalidomide, thioguanine, 6-TG, thiotepa, topotecan, toremifene, tositumomab, trastuzumab, tretinoin ATRA, uracil mustard, valrubicin, vinblastine, vincristine, vinorelbine, vorinostat, zoledronate, and zoledronic acid.

9. The method of claim 7, wherein the anti-cancer agent is ionizing radiation.

10. The method of claim 7, wherein the anti-cancer agent is x-radiation.

11. The method of claim 7, wherein the anti-cancer agent is docetaxel.

12. The method of claim 7, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, allopurinol, altretamine, amifostin, anakinra, anastrozole, arsenic trioxide, asparaginase, azacitidine, bevacizumab, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovorin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide, VM-26, testolactone, thalidomide, thioguanine, 6-TG, thiotepa, topotecan, toremifene, tositumomab, trastuzumab, uracil mustard, valrubicin, vinblastine, vincristine, vinorelbine, zoledronate, and zoledronic acid.

13. The method of claim 1, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, allopurinol, altretamine, amifostin, anakinra, anastrozole, arsenic trioxide, asparaginase, azacitidine, bevacizumab, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovorin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide, VM-26, testolactone, thalidomide, thioguanine, 6-TG, thiotepa, topotecan, toremifene, tositumomab, trastuzumab, uracil mustard, valrubicin, vinblastine, vincristine, vinorelbine, zoledronate, and zoledronic acid.

14. A method of enhancing the cytotoxic activity of an anti-cancer agent in a subject afflicted with a cancer which overexpresses TCTP comprising administering to the subject an anti-cancer agent and a compound, wherein the compound has the structure,

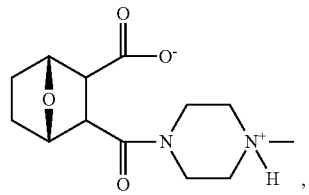 [SMILES: C[NH+]1CCN(C(=O)C2C(C(=O)[O-])[C@H]3CC[C@@H]2O3)CC1]

or a salt, enantiomer or zwitterion of the compound, in an amount effective to enhance the anti-cancer activity of the anti-cancer agent,
wherein the cancer is selected from adrenocortical cancer, bladder cancer, osteosarcoma, cervical cancer, esophageal, gallbladder, head and neck cancer, Hodgkin lymphoma, non-Hodgkin lymphoma, renal cancer, melanoma, pancreatic cancer, rectal cancer, thyroid cancer, throat cancer, breast cancer, lung cancer and prostate cancer.

15. The method of claim 14, wherein the cancer is selected from adrenocortical cancer, bladder cancer, osteosarcoma, cervical cancer, esophageal, gallbladder, head and neck cancer, Hodgkin lymphoma, non-Hodgkin lymphoma, renal cancer, melanoma, pancreatic cancer, rectal cancer, thyroid cancer and throat cancer.

16. The method of claim 15, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, allopurinol, altretamine, amifostin, anakinra, anastrozole, arsenic trioxide, asparaginase, azacitidine, bevacizumab, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, exemestane, fentanyl citrate, filgrastim, floxuridine, fludarabine, fluorouracil, fulvestrant, gefitinib, gemcitabine, gosereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovorin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide, VM-26, testolactone, thalidomide, thioguanine, 6-TG, thiotepa, topotecan, toremifene, tositumomab, trastuzumab, uracil mustard, valrubicin, vinblastine, vincristine, vinorelbine, zoledronate, and zoledronic acid.

17. The method of claim 15, wherein the anti-cancer agent is ionizing radiation.

18. The method of claim 15, wherein the anti-cancer agent is x-radiation.

19. The method of claim 15, wherein the anti-cancer agent is docetaxel.

20. The method of claim 14, wherein the cancer is selected from breast cancer, lung cancer, prostate cancer, and head and neck cancer.

21. The method of claim 20, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, allopurinol, altretamine, amifostin, anakinra, anastrozole, arsenic trioxide, asparaginase, azacitidine, bevacizumab, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, exemestane, fentanyl citrate, filgrastim, floxuridine, fludarabine, fluorouracil, fulvestrant, gefitinib, gemcitabine, goshereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovorin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide, VM-26, testolactone, thalidomide, thioguanine, 6-TG, thiotepa, topotecan, toremifene, tositumomab, trastuzumab, uracil mustard, valrubicin, vinblastine, vincristine, vinorelbine, zoledronate, and zoledronic acid.

22. The method of claim 20, wherein the anti-cancer agent is ionizing radiation.

23. The method of claim 20, wherein the anti-cancer agent is x-radiation.

24. The method of claim 20, wherein the anti-cancer agent is docetaxel.

25. The method of claim 14, wherein the anti-cancer agent is selected from x-radiation, ionizing radiation, a DNA damaging agent, a DNA intercalating agent, a microtubule stabilizing agent, a microtubule destabilizing agent, a spindle toxin, abarelix, aldesleukin, alemtuzumab, allopurinol, altretamine, amifostin, anakinra, anastrozole, arsenic trioxide, asparaginase, azacitidine, bevacizumab, bleomycin, bortezomib, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin sodium, darbepoetin alfa, dasatinib, daunorubicin, daunomycin, decitabine, denileukin, dexrazoxane, docetaxel, doxorubicin, dromostanolone propionate, exulizumab, epirubicin, epoetin alfa, erlotinib, estramustine, etoposide phosphate, etoposide, exemestane, fentanyl citrate, filgrastim, floxuridine, fludarabine, fluorouracil, fulvestrant, gefitinib, gemcitabine, goshereline acetate, histrelin acetate, hydroxyurea, ibritumomab tiuxetan, idarubicin, ifosfamide, imatinib mesylate, interferon alfa 2a, interferon alfa 2b, irinotecan, lapatinib ditosylate, lenalidomide, letrozole, leucovorin, leuprolide acetate, levamisole, lomustine, meclorethamine, megestrol acetate, melphalan, mercaptopurine, mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa 2b, pemetrexed disodium, pentostatin, pipobroman, plicamycin, mithramycin, porfimer sodium, procarbazine, quinacrine, rasburicase, rituximab, sargramostim, sorafenib, streptozocin, sunitinib, sunitinib maleate, talc, tamoxifen, temozolomide, teniposide, VM-26, testolactone, thalidomide, thioguanine, 6-TG, thiotepa, topotecan, toremifene, tositumomab, trastuzumab, uracil mustard, valrubicin, vinblastine, vincristine, vinorelbine, zoledronate, and zoledronic acid.

\* \* \* \* \*